(12) United States Patent
Anderson et al.

(10) Patent No.: US 7,001,729 B2
(45) Date of Patent: Feb. 21, 2006

(54) PRODUCTION OF ADENINE NUCLEOTIDE TRANSLOCATOR (ANT), NOVEL ANT LIGANDS AND SCREENING ASSAYS THEREFOR

(75) Inventors: Christen M. Anderson, Encinitas, CA (US); Robert E. Davis, San Diego, CA (US); William Clevenger, Oceanside, CA (US); Sandra Eileen Wiley, San Diego, CA (US); Scott W. Miller, San Marcos, CA (US); Tomas R. Szabo, San Diego, CA (US); Soumitra S. Ghosh, San Diego, CA (US); Walter H. Moos, Oakland, CA (US); Yazhong Pei, San Diego, CA (US)

(73) Assignee: Migenix Corp., San Diego, CA (US)

( * ) Notice: Subject to any disclaimer, the term of this patent is extended or adjusted under 35 U.S.C. 154(b) by 610 days.

(21) Appl. No.: 09/811,131

(22) Filed: Mar. 14, 2001

(65) Prior Publication Data

US 2005/0019835 A1 Jan. 27, 2005

Related U.S. Application Data

(60) Division of application No. 09/393,441, filed on Sep. 8, 1999, which is a continuation-in-part of application No. 09/185,904, filed on Nov. 3, 1998.

(51) Int. Cl.
G01N 29/00 (2006.01)
G01N 33/573 (2006.01)
C12N 11/00 (2006.01)

(52) U.S. Cl. ...................... 435/7.1; 435/69.1; 435/69.7; 435/7.93; 435/174; 530/350; 530/412; 536/23.1; 536/23.4; 536/23.5; 930/10

(58) Field of Classification Search ................ 435/69.1, 435/69.7, 7.1, 7.93, 174; 530/350, 412; 536/23.1, 536/23.4, 23.5; 930/10
See application file for complete search history.

(56) References Cited

FOREIGN PATENT DOCUMENTS

| EP | 0 130 074 A | 1/1985 |
|---|---|---|
| EP | 0 477 961 A | 4/1992 |
| EP | 0 770 610 A | 5/1997 |
| WO | WO 98/19714 | 5/1998 |
| WO | WO 98/28415 | 7/1998 |
| WO | WO 99/07845 | 2/1999 |

OTHER PUBLICATIONS

Hatanaka et al. Significant Expression of Functional Human Type 1 Mitochondrial ADP/ATP Carrier in Yeast Mitochondria. (2001) Biol. Pharm. Bull. 24(6) 595–599.*
Heimpel et al. Expression of Mitochondrial ADP/ATP Carrier in *Escherichia coli*. (2001) J. Biol. Chem. 276(15): 11499–11506.*
Miroux et al. Over–production of Proteins in *Escherichia coli*: Mutant Hosts that Allow Synthesis of some Membrane Proteins and Globular Proteins at High Levels. (1996) J. Mol. Biol. 260: 289–298.*
Fiermonte et al. Abundant bacterial expression and reconstitution of an intrinsic membrane–transport protein from bovine mitochondria. (1993) Biochem. J. 294: 293–299.*
Neumann et al. Induction of Multiple Heart Autoantibodies in Mice with Coxsackievirus B3– and Cardiac Myosin–Induced Autoimmune Myocarditis. J. Immunol. (1994) 152: 343–350.*
Adrian et al., "Sequences Required for Delivery and Localization of the ADP/ATP Translocator to the Mitochondrial Inner Membrane," *Molecular and Cellular Biology* 6(2):626–634, 1986.
Aquila et al., "Complete Amino Acid Sequence of the ADP/ATP Carrier from Beef Heart Mitochondria," *Hoppe-Seyler's Z. Physiol. Chem.* 363:345–349, 1982.
Block et al., "Atractyloside and Bongkrekic Acid Sites in the Mitochondrial ADP/ATP Carrier Protein," *FEBS Letters* 131(2):213–218, 1981.
Block et al., "Chemical Modifications and Active Site Labeling of the Mitochondrial ADP/ATP Carrier," *Methods in Enzymology* 125:658–670, 1986.
Block et al., "Fluorescent Probes of the Mitochondrial ADP/ATP Carrier Protein," *Methods in Enzymology* 125: 639–649, 1986.
Bojanovski et al., "Studies on the Adenine Nucleotide Translocase from Rat Liver Mitochondria," *Eur. J. Biochem.* 71:539–548, 1976.
Boulay et al., "Photolabeling Approach to the Study of the Topography of the Atractyloside Binding Site in Mitochondrial Adenosine 5'-Diphosphate/Adenosine 5'-Triphosphate Carrier Protein," *Biochemistry* 22: 477–484, 1983.
Boulay et al., "Synthesis and Properties of Fluorescent Derivatives of Atractyloside as Potential Probes on the Mitochondrial ADP/ATP Carrier Protein," *Analytical Biochemistry* 128:323–330, 1983.
Brandolin et al, "Partial Purification of an Atractyloside-Binding Protein from Mitochondria," *FEBS Letters* 46(1):149–153, 1974.
Brandolin et al., "Substrate–Induced Modifications of the Intrinsic Fluorescence of the Isolated Adenine Nucleotide Carrier Protein: Demonstration of Distinct Conformational States," *Biochemistry* 24:1991–1997, 1985.

(Continued)

Primary Examiner—Jon Weber
Assistant Examiner—Holly Schnizer
(74) Attorney, Agent, or Firm—Seed IP Law Group PLLC

(57) ABSTRACT

Compositions and methods are provided for producing adenine nucleotide translocator (ANT) polypeptides and fusion proteins, including the production and use of recombinant expression constructs having a regulated promoter. ANT ligands and compositions and methods for identifying ANT ligands, agents that bind ANT and agents that interact with ANT are also disclosed.

22 Claims, 14 Drawing Sheets

OTHER PUBLICATIONS

Brunelli and Pall, "A Series of Yeast Shuttle Vectors for Expression of cDNAs and Other DNA Sequences," *Yeast* 9:1299–1309, 1993.

Cozens et al., "DNA Sequences of Two Expressed Nuclear Genes for Human Mitochondrial ADP/ATP Translocase," *J. Mol. Biol.* 206:261–280, 1989.

Fiore et al., "The Mitochondrial ADP/ATP Carrier: Structural, Physiological and Pathological Aspects," *Biochimie* 80:137–150, 1998.

Giraud et al., "Expression of Human *ANT2* Gene in Highly Proliferative Cells: GRBOX, a New Transcriptional Element, Is Involved in the Regulation of Glycolytic ATP Import into Mitochondria," *J. Mol. Biol.* 281:409–418, 1998.

Green and Reed, "Mitochondria and Apoptosis," *Science* 281:1309–1312, Aug. 28, 1998.

Klingenberg et al., "Isolation of the ADP, ATP Carrier as the Carboxyatractylate Protein Complex from Mitochondria," *Biochimica et Biophysica Acta* 503:193–210, 1978.

Klingenberg, "The ADP–ATP Translocation in Mitochondria, a Membrane Potential Controlled Transport," *J. Membrane Biol.* 56:97–105, 1980.

Klingenberg, M., "Principles of Carrier Catalysis Elucidated by Comparing Two Similar Membrane Translocators from Mitochondria, the ADP/ATP Carrier and the Uncoupling Protein," *Annals New York Academy of Sciences* 456:279–288, 1985.

Ku et al., "The Human Fibroblast Adenine Nucleotide Translocator Gene," *Journal of Biological Chemistry* 265(27): 16060–16063, 1990.

Lauquin and Vignais, "Interaction of [$^3$H]Bongkrekic Acid with the Mitochondrial Adenine Nucleotide Translocator," *Biochemistry* 15(11):2316–2322, 1976.

Lauquin et al., "Isobongkrekic Acid, a New Inhibitor of Mitochondrial ADP–ATP Transport: Radioactive Labeling and Chemical and Biological Properties," *Biochemistry* 15(11):2323–2327, 1976.

Li et al., "A Human Muscle Adenine Nucleotide Translocator Gene Has Four Exons, is Located on Chromosome 4, and is Differentially Expressed," *Journal of Biological Chemistry* 264(24): 13998–14004, 1989.

Li et al., "OXBOX, a Positive Transcriptional Element of the Heart–Skeletal Muscle ADP/ATP Translocator Gene," *Journal of Biological Chemistry* 265(33): 20585–20588, 1990.

Marzo et al., "Bax and Adenine Nucleotide Translocator Cooperate in the Mitochondrial Control of Apoptosis," *Science* 281:2027–2031, Sep. 25, 1998.

Murdock et al., "Up–Regulation of Nuclear and Mitochondrial Genes in the Skeletal Muscle of Mice Lacking the Heart/Muscle Isoform of the Adenine Nucleotide Translocator," *The Journal of Biological Chemistry* 274(20):14429–14433, May 14, 1999.

Piozzi et al., "Structure of Atroctyloside," Chemical Abstracts Acc. No. 67:117201, 1967.

Piozzi et al., "Struttura dell'attrattiloside," *Gazzetta Chimica Italiana* 97(6): 935–954, 1967. (English summary on p. 936).

Plano et al., "Rickettsia Prowazekii and ATP/ADP Translocase," *Annals of the New York Academy of Sciences* 590: 397–407, 1990.

Rosenberg, *Protein Analysis and Purification: Benchtop Techniques*, Birkhauser, Boston, pp. 335–347, 1996.

Roux et al., "Fluorometric Titration of the Mitochondrial ADP/ATP Carrier Protein in Muscle Homogenate with Atractyloside Derivatives," *Analytical Biochemistry* 234:31–37, 1996.

Santi and Luciani (eds.), *Atractyloside: Chemistry, Biochemistry and Toxicology*, Piccin Medical Books, Padova, Italy, 1978.

Smagula and Douglas, "Mitochondrial Import of the ADP/ADP Carrier Protein in *Saccharomyces cerevisiae*," *Journal of Biological Chemistry* 263(14): 6783–6790, 1988.

Sterling, "Direct Thyroid Hormone Activation of Mitochondria: The Role of Adenine Nucleotide Translocase," *Endocrinology* 119(1):292–295, 1986.

Stubbs, "Inhibitors of the Adenine Nucleotide Translocase," *Pharmac. Ther.* 7:329–349, 1979.

Tjaden et al. "Expression of a Plastidic ATP/ADP Transporter Gene in *Escherichia coli* Leads to a Functional Adenine Nucleotide Transport System in the Bacterial Cytoplasmic Membrane," *Journal of Biological Chemistry* 273(16): 9630–9636, 1998.

Vignais et al., "[60] $^3$H– or $^{35}$S–Labeled Atractyloside and Carboxyatractyloside, Atractyloside Derivatives Used for Affinity Chromatography, Photoaffinity Labeling, and Spin Labeling, and $^3$H– or $^{14}$C–Labeled Bongkrekic Acid," *Methods in Enzymology* 55:518–533, 1979.

Vignais et al., "Adenosine Diphospahte Translocation in Mitochondria. Nature of the Receptor Site for Carboxyatractyloside (Gummiferin)," *Biochemistry* 12(8): 1508–1519, 1973.

Yan and Sohal, "Mitochondrial Adenine Nucleotide Translocase is Modified Oxidatively During Aging," *Proc. Natl. Acad. Sci. USA* 95:12896–12901, Oct. 1998.

\* cited by examiner

```
ANT1m  ATGGGTGATCACGCTTGGAGCTTCCTAAAGGACTTCCTGGCCGGGGCGGTCGCCGCTGCCGTCTCCAAGACGGCGGTCGC  80
ANT2m  ATGACAGATGCCGCTGTGTCCTTCGCCAAGGACTTCCTGGCAGGTGGAGTGGCCGCAGCCATCTCCAAGACGGCGGTAGC  80
ANT3m  ATGACGGAACAGGCCATGTCCTTCGCCAAAGACTTCTTGGCCGGAGGCATCGCCGCGGCCATCTCCAAGACGGCCGTGGC  80

ANT1m  CCCCATCGAGAGGGTCAAACTGCTGCTGCAGGTCCAGCATGCCAGCAAACAGATCAGTGCTGAGAAGCAGTACAAAGGGA  160
ANT2m  GCCCATCGAGCGGGTCAAGCTGCTGCTGCAGGTGCAGCATGCCAGCAAGCAGATCACTGCAGATAAGCAATACAAAGGCA  160
ANT3m  TCCGATCGAGCGGGTCAAGCTGCTGCTGCAGGTCCAGCACGCCAGCAAGCAGATCGCCGCCGACAAGCAGTACAAAGGGCA  160

ANT1m  TCATTGATTGTGTGGTGAGAATCCCTAAGGAGCAGGGCTTCCTGTCCTTCTGGAGGGGTAACCTGGCCAACGTGATCCGT  240
ANT2m  TTATAGACTGCGTGGTCCGTATTCCCAAGGAGCAGGAAGTTTCTGTCCTTCTGGCGCGGGTAACCTGGCCAATGTCATCAGA  240
ANT3m  TCGTGGACTGCATTGTCCGCATCCCCAAGGAGCAGGGCGTGCTGTCCTTCTGGAGGGGCAACCTTGCCAACGTCATTCGC  240

ANT1m  TACTTCCCCACCCAAGCTCTCAACTTCGCCTTCAAGGACAAGTACAAGCAGTCTTCTTAGGGGGTGTGGATCGGCATAA  320
ANT2m  TACTTCCCCACCCAGGCTCTTAACTTCGCCTTCAAAGATAAATACAAGCAGATCTTCCTGGGTGGTGTGGACAAGAGAAC  320
ANT3m  TACTTCCCCACTCAAGCGCTCAACTTCGCCTTCAAGGATAAGTACAAGCAGATCTTCCTGGGGGGCGTGGACAAGCCACAC  320

ANT1m  GCAGTTCTGGCGCTACTTTGCTGTAACCTGGCGTCCGGTGGGGCCGCTGGGGCCACCTCCCTTTGCTTTGTGTACCCGC  400
ANT2m  CCAGTTTTGGCTCTACTTTGCAGGGAATCTGGCATGGGTGGTGCCGCAGGGGCCACATCCCTGTGTTTGTGTACCCTC  400
ANT3m  GCAGTTCTGGAGGTACTTTGCGGGCAACCTGGCCTCCGGCGGTGCGGCCGGCGACCTCCCTCTGCTTGTGTACCCGC  400

ANT1m  TGGACTTTGCTAGGACCAGGTTGGCTGCTGATGTGGGCAGGC---GCGCCCAGCGTGAGTTCCATGGTCTGGGCGACTGT  477
ANT2m  TTGATTTTGCCCGGTACCCGTCTAGCAGCTGATGTGGGTAAAGCTGGAGCTGAAAGGGAATTCCGAGGCCTCGGTGACTGC  480
ANT3m  TGGATTTTGCCAGAACCCGGCTGGCAGCGGACGTGGGAAAGTCAGGCACAGAGCGCGAGTTCCGAGGCCTGGGAGACTGC  480
```

*Fig. 1A*

```
ANT1m  ATCATCAAGATCTTCAAGTCTGATGGCCTGAGGGGGCTCTACCAGGGTTTCAACGTCTCTGTCCAAGGCATCATTATCTA  557
ANT2m  CTGGTTAAGATCTACAAATCTGATGGGATTAAGGGCCTGTACCAAGGCTTTAACGTGTCTGTGCAGGGTATTATCATCTA  560
ANT3m  CTGGTGAAGATCACCAAGTCCGACGGCATCCGGGGCCTGTACCAGGGCTTCAGTGTCTCCGTGCAGGGCATCATCATCTA  560

ANT1m  TAGAGCTGCCTACTTCGGAGTCTATGATACTGCCAAGGGGATGCTGCCTGACCCCAAGAACGTGCACATTTTTGTGAGCT  637
ANT2m  CCGAGCCGCCTACTTCGGTATCTATGACACTGCAAAGGGAATGCTTCCGGATCCCAAGAACACTCACATCGTCATCAGCT  640
ANT3m  CCGGGCGGCCTACTTCGGCGTGTACGATACGGCCAAGGGCATGCTCCCCGACCCCAAGAACACGCACATCGTGGTGAGCT  640

ANT1m  GGATGATTGCCCAGAGTGTGACGGCAGTCGCAGGGCTGCTGTCCTACCCCTTTGACACTGTTCGTCGTACAATGATGATG  717
ANT2m  GGATGATCGCACAGACTGTCACTGCTGTTGCCGGGTTTGACTTCCTATCCATTTGACACTGTTCGCCGCCGCATGATGATG  720
ANT3m  GGATGATCGCGCAGACCGTGACGGCCGTGGCCGGCGTGGTGTCCTACCCCTTCGACACCGTGCGGCGGCGCATGATGATG  720

ANT1m  CAGTCCGGCCGAAAGGGGGCCGATATTATGTACACGGGGACAGTTGACTGCTGGAGGAAGATTGCAAAAGACGAAGGAGC  797
ANT2m  CAGTCAGGGCGCAAAGGAACTGACATCATGTACACAGGCACGGCTTGACTGCTGGCGGAAGATTGCTCGTGATGAAGGAGG  800
ANT3m  CAGTCCGGGCGCAAAGGAGCTGACATCATGTACACGGGCACCGTGGACTGTTGGAGGAAGATCTTCAGAGATGAGGGCGG  800

ANT1m  CAAGGCCTTCTTCAAAGGTGCCTGGTCCAATGTGCTGAGAGGCATGGGCGGTGCTTTTGTATTGGTGTTGTATGATGAGA  877
ANT2m  CAAAGCTTTTTTCAAGGGTGCATGGTCCAATGTTTCTCAGAGGCATGGGTGGTGCTTTTGTGCTTGTCTTGTATGATGAAA  880
ANT3m  CAAGGCCTTCTTCAAGGGTGCGTGGTCCAACGTCCTCCGGGGCATGGGCGGCGCGTTCGTGCTGGTCCTGTACGACGAGC  880

ANT1m  TCAAAAAATATGTCTAA  894
ANT2m  TCAAGAAGTACACATAA  897
ANT3m  TCAAGAAGGTGATCTAA  897
```

*Fig. 1B*

```
HANT1p  MGDHAWSFLKDFLAGAVAAAVSKTAVAPIERVKLLLQVQHASKQISAEKQ  50
HANT2p  MTDAAWSFAKDFLAGGVAAAISKTAVAPIERVKLLLQVQHASKQITADKQ  50
HANT3p  MTEQAISFAKDFLAGGIAAAISKTAVAPIERVKLLLQVQHASKQIAADKQ  50

HANT1p  YKGIIDCVVRIPKEQGFLSFWRGNLANVIRYFPTQALNFAFKDKYKQLFL  100
HANT2p  YKGIIDCVVRIPKEQEVLSFWRGNLANVIRYFPTQALNFAFKDKYKQIFL  100
HANT3p  YKGIVDQIVRIPKEQGVLSFWRGNLANVIRYFPTQALNFAFKDKYKQIFL  100

HANT1p  GGVDRHKQFWRYFAGNLASGGAAGATSLCFVYPLDFARTRLAADVGRR-A  149
HANT2p  GGVDKRTQFWLYFAGNLASGGAAGATSLCFVYPLDFARTRLAADVGKAGA  150
HANT3p  GGVDKHTQFWRYFAGNLASGGAAGATSLCFVYPLDFARTRLAADVGKSGT  150

HANT1p  QREFHGLGDQIKIFKSDGLRGLYQGFNVSVQGIIIYRAAYFGVYDTAKG  199
HANT2p  EREFRGLGDCLVKIYKSDGIKGLYQGFNVSVQGIIIYRAAYFGIYDTAKG  200
HANT3p  EREFRGLGDCLVKITKSDGIRGLYQGFSVSVQGIIIYRAAYFGVYDTAKG  200

HANT1p  MLPDPKNVHIFVSWMIAQSVTAVAGLLSYPFDTVRRRMMMQSGRKGADIM  249
HANT2p  MLPDPKNTHIVISWMIAQTVTAVAGLTSYPFDTVRRRMMMQSGRKGTDIM  250
HANT3p  MLPDPKNTHIVVSWMIAQTVTAVAGVVSYPFDTVRRRMMMQSGRKGADIM  250

HANT1p  YTGTVDCWRKIAKDEGAKAFFKGAWSNVLRGMGGAFVLVLYDEIKKYV.  298
HANT2p  YTGTLDCWRKIARDEGGKAFFKGAWSNVLRGMGGAFVLVLYDEIKKYT.  299
HANT3p  YTGTVDCWRKIFRDEGGKAFFKGAWSNVLRGMGGAFVLVLYDELKKVI.  299
```

*Fig. 2*

[cpd 24] nM

SEQUENCE LISTING

<160> NUMBER OF SEQ ID NOS: 37

<210> SEQ ID NO 1
<211> LENGTH: 894
<212> TYPE: DNA
<213> ORGANISM: Homo sapien

<400> SEQUENCE: 1

```
atgggtgatc acgcttggag cttcctaaag gacttcctgg ccggggcggt cgccgctgcc      60
gtctccaaga ccgcggtcgc ccccatcgag agggtcaaac tgctgctgca ggtccagcat     120
```

```
gccagcaaac agatcagtgc tgagaagcag tacaaaggga tcattgattg tgtggtgaga      180
atccctaagg agcagggctt cctctccttc tggagg ggta acctggccaa cgtgatccgt     240
tacttcccca cccaagctct caacttcgcc ttcaaggaca agtacaagca gctcttctta     300
gggggtgtgg atcggcataa gcagttctgg cgctactttg ctggtaacct ggcgtccggt     360
ggggccgctg gggccacctc cctttgcttt gtctacccgc tggactttgc taggaccagg     420
ttggctgctg atgtgggcag gcgcgcccag cgtgagttcc atggtctggg cgactgtatc     480
atcaagatct tcaagtctga tggcctgagg gggctctacc agggtttcaa cgtctctgtc     540
caaggcatca ttatctatag agctgcctac ttcggagtct atgatactgc caaggggatg     600
ctgcctgacc ccaagaacgt gcacattttt gtgagctgga tgattgccca gagtgtgacg     660
gcagtcgcag gctgctgtc ctacccctt gacactgttc gtcgtagaat gatgatgcag       720
tccggccgga aggggccgga tattatgtac acggggacag ttgactgctg gaggaagatt     780
gcaaaagacg aaggagccaa ggccttcttc aaaggtgcct ggtccaatgt gctgagaggc     840
atgggcggtg cttttgtatt ggtgttgtat gatgagatca aaaaatatgt ctaa           894
```

<210> SEQ ID NO 2
<211> LENGTH: 897
<212> TYPE: DNA
<213> ORGANISM: Homo sapien

<400> SEQUENCE: 2

```
atgacagatg ccgcattgtc cttcgccaag gacttcctgg caggtggagt ggccgcagcc      60
atctccaaga cggcggtagc gcccatcgag cgggtcaagc tgctgctgca ggtgcagcat     120
gccagcaagc agatcactgc agataagcaa tacaaaggct tatagactg cgtggtccgt      180 attcccaagg agcaggaagt tctgtccttc tggcgcggta acctggccaa tgtcatcaga     240
tacttcccca cccaggctct taacttcgcc ttcaaagata aatacaagca gatcttcctg     300
ggtggtgtgg acaagagaac ccagtttttgg cgctactttg cagggaatct ggcatcgggt    360
ggtgccgcag gggccacatc cctgtgtttt gtgtaccctc ttgattttgc ccgtacccgt    420
ctagcagctg atgtgggtaa agctggagct gaaagggaat tccgaggcct cggtgactgc     480
ctggttaaga tctacaaatc tgatgggatt aagggcctgt accaaggctt taacgtgtct    540
gtgcagggta ttatcatcta ccgagccgcc tacttcggta tctatgacac tgcaagggga    600
atgcttccgg atcccaagaa cactcacatc gtcatcagct ggatgatcgc acagactgtc     660
actgctgttg ccgggttgac ttcctatcca tttgacaccg ttcgccgccg catgatgatg     720
cagtcagggc gcaaaggaac tgacatcatg tacacaggca cgcttgactg ctggcggaag    780
attgctcgtg atgaaggagg caaagctttt ttcaagggtg catggtccaa tgttctcaga    840
ggcatgggtg gtgcttttgt gcttgtcttg tatgatgaaa tcaagaagta cacataa       897
```

<210> SEQ ID NO 3
<211> LENGTH: 897
<212> TYPE: DNA
<213> ORGANISM: Homo sapien

<400> SEQUENCE: 3

```
atgacggaac aggccatctc cttcgccaaa gacttcttgg ccggaggcat cgccgccgcc     60
atctccaaga cggccgtggc tccgatcgag cgggtcaagc tgctgctgca ggtccagcac    120
gccagcaagc agatcgccgc cgacaagcag tacaagggca tcgtggactg cattgtccgc    180
```

```
atccccaagg agcagggcgt gctgtccttc tggagggca accttgccaa cgtcattcgc      240
tacttcccca ctcaagccct caacttcgcc ttcaaggata agtacaagca gatcttcctg      300
gggggcgtgg acaagcacac gcagttctgg aggtactttg cgggcaacct ggcctccggc      360
ggtgcggccg gcgcgacctc cctctgcttc gtgtacccgc tggattttgc cagaacccgc      420
ctggcagcgg acgtgggaaa gtcaggcaca gagcgcgagt tccgaggcct gggagactgc      480
ctggtgaaga tcaccaagtc cgacggcatc cggggcctgt accagggctt cagtgtctcc      540
gtgcagggca tcatcatcta ccgggcggcc tacttcggcg tgtacgatac ggccaagggc      600
atgctccccg accccaagaa cacgcacatc gtggtgagct ggatgatcgc gcagaccgtg      660
acggccgtgg ccggcgtggt gtcctacccc ttcgacacgg tgcggcggcg catgatgatg      720
cagtccgggc gcaaaggagc tgacatcatg tacacgggca ccgtcgactg ttggaggaag      780
atcttcagag atgagggggg caaggccttc ttcaagggtg cgtggtccaa cgtcctgcgg      840
ggcatggggg cgccttcgt gctggtcctg tacgacgagc tcaagaaggt gatctaa      897
```

<210> SEQ ID NO 4
<211> LENGTH: 43
<212> TYPE: DNA
<213> ORGANISM: Artificial Sequence
<220> FEATURE:
<223> OTHER INFORMATION: PCR Primer

<400> SEQUENCE: 4

```
ttatatctcg agtatgggtg atcacgcttg gagcttccta aag                        43
```

<210> SEQ ID NO 5
<211> LENGTH: 43
<212> TYPE: DNA
<213> ORGANISM: Artificial Sequence
<220> FEATURE:
<223> OTHER INFORMATION: PCR Primer

<400> SEQUENCE: 5

```
tatataggta ccttagacat attttttgat ctcatcatac aac                        43
```

<210> SEQ ID NO 6
<211> LENGTH: 43
<212> TYPE: DNA
<213> ORGANISM: Artificial Sequence
<220> FEATURE:
<223> OTHER INFORMATION: PCR Primer

<400> SEQUENCE: 6

```
ttatatctcg agtatgacag atgccgctgt gtccttcgcc aag                        43
```

<210> SEQ ID NO 7
<211> LENGTH: 43
<212> TYPE: DNA
<213> ORGANISM: Artificial Sequence
<220> FEATURE:
<223> OTHER INFORMATION: PCR Primer

<400> SEQUENCE: 7

```
tatataggta ccttatgtgt acttcttgat ttcatcatac aag                        43
```

<210> SEQ ID NO 8
<211> LENGTH: 43
<212> TYPE: DNA
<213> ORGANISM: Artificial Sequence
<220> FEATURE:
<223> OTHER INFORMATION: PCR Primer

```
<400> SEQUENCE: 8
ttatatctcg agtatgacgg aacaggccat ctccttcgcc aaa                43

<210> SEQ ID NO 9
<211> LENGTH: 44
<212> TYPE: DNA
<213> ORGANISM: Artificial Sequence
<220> FEATURE:
<223> OTHER INFORMATION: PCR Primer

<400> SEQUENCE: 9
tatataggta ccttagagtc accttcttga gctcgtcgta cagg               44

<210> SEQ ID NO 10
<211> LENGTH: 21
<212> TYPE: DNA
<213> ORGANISM: Artificial Sequence
<220> FEATURE:
<223> OTHER INFORMATION: Sequence primer

<400> SEQUENCE: 10
tatgccatag cattttatc c                                         21

<210> SEQ ID NO 11
<211> LENGTH: 18
<212> TYPE: DNA
<213> ORGANISM: Artificial Sequence
<220> FEATURE:
<223> OTHER INFORMATION: Sequence primer

<400> SEQUENCE: 11
cgccaaaaca gccaagct                                            18

<210> SEQ ID NO 12
<211> LENGTH: 45
<212> TYPE: DNA
<213> ORGANISM: Artificial Sequence
<220> FEATURE:
<223> OTHER INFORMATION: Mutagenic oligonucleotide primer

<400> SEQUENCE: 12
ggagatggcc tgttccgtca tcttatcgtc atcgtcgtac agatc              45

<210> SEQ ID NO 13
<211> LENGTH: 45
<212> TYPE: DNA
<213> ORGANISM: Artificial Sequence
<220> FEATURE:
<223> OTHER INFORMATION: Mutagenic oligonucleotide primer

<400> SEQUENCE: 13
gatctgtacg acgatgacga taagatgacg aacaggcca tctcc               45

<210> SEQ ID NO 14
<211> LENGTH: 35
<212> TYPE: DNA
<213> ORGANISM: Artificial Sequence
<220> FEATURE:
<223> OTHER INFORMATION: PCR primer

<400> SEQUENCE: 14
cccggggaat tctgatgacg gaacaggcca tctcc                         35

<210> SEQ ID NO 15
```

```
<211> LENGTH: 34
<212> TYPE: DNA
<213> ORGANISM: Artificial Sequence
<220> FEATURE:
<223> OTHER INFORMATION: PCR primer

<400> SEQUENCE: 15
cccgggctcg agttagagtc accttcttga gctc                            34

<210> SEQ ID NO 16
<211> LENGTH: 41
<212> TYPE: DNA
<213> ORGANISM: Artificial Sequence
<220> FEATURE:
<223> OTHER INFORMATION: PCR primer

<400> SEQUENCE: 16
ttataggatc catgacggaa caggccatct ccttcgccaa a                    41

<210> SEQ ID NO 17
<211> LENGTH: 41
<212> TYPE: DNA
<213> ORGANISM: Artificial Sequence
<220> FEATURE:
<223> OTHER INFORMATION: PCR primer

<400> SEQUENCE: 17
ttaaagaatt cttagatcac cttcttgagc tcgtcgtaca g                    41

<210> SEQ ID NO 18
<211> LENGTH: 18
<212> TYPE: DNA
<213> ORGANISM: Artificial Sequence
<220> FEATURE:
<223> OTHER INFORMATION: Sequencing primer

<400> SEQUENCE: 18
aaatgataac catctcgc                                              18

<210> SEQ ID NO 19
<211> LENGTH: 18
<212> TYPE: DNA
<213> ORGANISM: Artificial Sequence
<220> FEATURE:
<223> OTHER INFORMATION: Sequencing primer

<400> SEQUENCE: 19
acttcaagga gaatttcc                                              18

<210> SEQ ID NO 20
<211> LENGTH: 18
<212> TYPE: DNA
<213> ORGANISM: Artificial Sequence
<220> FEATURE:
<223> OTHER INFORMATION: Sequencing primer

<400> SEQUENCE: 20
acttcgcctt cacggata                                              18

<210> SEQ ID NO 21
<211> LENGTH: 18
<212> TYPE: DNA
<213> ORGANISM: Artificial Sequence
<220> FEATURE:
<223> OTHER INFORMATION: Sequencing primer

<400> SEQUENCE: 21
```
tacggccaag ggcattct                                                 18

<210> SEQ ID NO 22
<211> LENGTH: 18
<212> TYPE: DNA
<213> ORGANISM: Artificial Sequence
<220> FEATURE:
<223> OTHER INFORMATION: Sequencing primer

<400> SEQUENCE: 22
tgaagcggaa gttcctat                                                 18

<210> SEQ ID NO 23
<211> LENGTH: 18
<212> TYPE: DNA
<213> ORGANISM: Artificial Sequence
<220> FEATURE:
<223> OTHER INFORMATION: Sequencing primer

<400> SEQUENCE: 23
atgccggttc ccgtacga                                                 18

<210> SEQ ID NO 24
<211> LENGTH: 31
<212> TYPE: DNA
<213> ORGANISM: Artificial Sequence
<220> FEATURE:
<223> OTHER INFORMATION: Mutagenic oligonucleotide primer

<400> SEQUENCE: 24
ggcctgttcc gtcatcttat cgtcatcgtc g                                  31

<210> SEQ ID NO 25
<211> LENGTH: 31
<212> TYPE: DNA
<213> ORGANISM: Artificial Sequence
<220> FEATURE:
<223> OTHER INFORMATION: Mutagenic oligonucleotide primer

<400> SEQUENCE: 25
cgacgatgac gataagatga cggaacaggc c                                  31

<210> SEQ ID NO 26
<211> LENGTH: 41
<212> TYPE: DNA
<213> ORGANISM: Artificial Sequence
<220> FEATURE:
<223> OTHER INFORMATION: PCR primer

<400> SEQUENCE: 26
ttaaagaatt catgacggaa caggccatct ccttcgccaa a                       41

<210> SEQ ID NO 27
<211> LENGTH: 41
<212> TYPE: DNA
<213> ORGANISM: Artificial Sequence
<220> FEATURE:
<223> OTHER INFORMATION: PCR primer

<400> SEQUENCE: 27
ttataggatc cttagatcac cttcttgagc tcgtcgtaca g                       41

<210> SEQ ID NO 28
<211> LENGTH: 42
<212> TYPE: DNA

```
<213> ORGANISM: Artificial Sequence
<220> FEATURE:
<223> OTHER INFORMATION: PCR primer

<400> SEQUENCE: 28
ttaatgggta ccatgacgga acaggccatc tccttcgcca aa                          42

<210> SEQ ID NO 29
<211> LENGTH: 42
<212> TYPE: DNA
<213> ORGANISM: Artificial Sequence
<220> FEATURE:
<223> OTHER INFORMATION: PCR primer

<400> SEQUENCE: 29
ttatactcga gttagatcac cttcttgagc tcgtcgtaca gg                          42

<210> SEQ ID NO 30
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 30

Cys Trp Arg Lys Ile Phe Arg Asp Glu Gly Gly Lys Ala Phe Phe
1               5                   10                  15

<210> SEQ ID NO 31
<211> LENGTH: 297
<212> TYPE: PRT
<213> ORGANISM: Homo sapien

<400> SEQUENCE: 31

Met Gly Asp His Ala Trp Ser Phe Leu Lys Asp Phe Leu Ala Gly Ala
1               5                   10                  15

Val Ala Ala Ala Val Ser Lys Thr Ala Val Ala Pro Ile Glu Arg Val
                20                  25                  30

Lys Leu Leu Leu Gln Val Gln His Ala Ser Lys Gln Ile Ser Ala Glu
            35                  40                  45

Lys Gln Tyr Lys Gly Ile Ile Asp Cys Val Val Arg Ile Pro Lys Glu
        50                  55                  60

Gln Gly Phe Leu Ser Phe Trp Arg Gly Asn Leu Ala Asn Val Ile Arg
65                  70                  75                  80

Tyr Phe Pro Thr Gln Ala Leu Asn Phe Ala Phe Lys Asp Lys Tyr Lys
                85                  90                  95

Gln Leu Phe Leu Gly Gly Val Asp Arg His Lys Gln Phe Trp Arg Tyr
            100                 105                 110

Phe Ala Gly Asn Leu Ala Ser Gly Gly Ala Ala Gly Ala Thr Ser Leu
        115                 120                 125

Cys Phe Val Tyr Pro Leu Asp Phe Ala Arg Thr Arg Leu Ala Ala Asp
    130                 135                 140

Val Gly Arg Arg Ala Gln Arg Glu Phe His Gly Leu Gly Asp Cys Ile
145                 150                 155                 160

Ile Lys Ile Phe Lys Ser Asp Gly Leu Arg Gly Leu Tyr Gln Gly Phe
                165                 170                 175

Asn Val Ser Val Gln Gly Ile Ile Ile Tyr Arg Ala Ala Tyr Phe Gly
            180                 185                 190

Val Tyr Asp Thr Ala Lys Gly Met Leu Pro Asp Pro Lys Asn Val His
        195                 200                 205
```

-continued

```
Ile Phe Val Ser Trp Met Ile Ala Gln Ser Val Thr Ala Val Ala Gly
    210                 215                 220

Leu Leu Ser Tyr Pro Phe Asp Thr Val Arg Arg Met Met Met Gln
225                 230                 235                 240

Ser Gly Arg Lys Gly Ala Asp Ile Met Tyr Thr Gly Thr Val Asp Cys
                245                 250                 255

Trp Arg Lys Ile Ala Lys Asp Glu Gly Ala Lys Ala Phe Phe Lys Gly
                260                 265                 270

Ala Trp Ser Asn Val Leu Arg Gly Met Gly Gly Ala Phe Val Leu Val
            275                 280                 285

Leu Tyr Asp Glu Ile Lys Lys Tyr Val
290                 295

<210> SEQ ID NO 32
<211> LENGTH: 298
<212> TYPE: PRT
<213> ORGANISM: Homo sapien

<400> SEQUENCE: 32

Met Thr Asp Ala Ala Leu Ser Phe Ala Lys Asp Phe Leu Ala Gly Gly
1               5                   10                  15

Val Ala Ala Ile Ser Lys Thr Ala Val Ala Pro Ile Glu Arg Val
            20                  25                  30

Lys Leu Leu Leu Gln Val Gln His Ala Ser Lys Gln Ile Thr Ala Asp
            35                  40                  45

Lys Gln Tyr Lys Gly Ile Ile Asp Cys Val Val Arg Ile Pro Lys Glu
        50                  55                  60

Gln Glu Val Leu Ser Phe Trp Arg Gly Asn Leu Ala Asn Val Ile Arg
65                  70                  75                  80

Tyr Phe Pro Thr Gln Ala Leu Asn Phe Ala Phe Lys Asp Lys Tyr Lys
                85                  90                  95

Gln Ile Phe Leu Gly Gly Val Asp Lys Arg Thr Gln Phe Trp Arg Tyr
            100                 105                 110

Phe Ala Gly Asn Leu Ala Ser Gly Gly Ala Ala Gly Ala Thr Ser Leu
        115                 120                 125

Cys Phe Val Tyr Pro Leu Asp Phe Ala Arg Thr Arg Leu Ala Ala Asp
130                 135                 140

Val Gly Lys Ala Gly Ala Glu Arg Glu Phe Arg Gly Leu Gly Asp Cys
145                 150                 155                 160

Leu Val Lys Ile Tyr Lys Ser Asp Gly Ile Lys Gly Leu Tyr Gln Gly
                165                 170                 175

Phe Asn Val Ser Val Gln Gly Ile Ile Ile Tyr Arg Ala Ala Tyr Phe
            180                 185                 190

Gly Ile Tyr Asp Thr Ala Lys Gly Met Leu Pro Asp Pro Lys Asn Thr
        195                 200                 205

His Ile Val Ile Ser Trp Met Ile Ala Gln Thr Val Thr Ala Val Ala
210                 215                 220

Gly Leu Thr Ser Tyr Pro Phe Asp Thr Val Arg Arg Met Met Met
225                 230                 235                 240

Gln Ser Gly Arg Lys Gly Thr Asp Ile Met Tyr Thr Gly Thr Leu Asp
                245                 250                 255

Cys Trp Arg Lys Ile Ala Arg Asp Glu Gly Lys Ala Phe Phe Lys
                260                 265                 270

Gly Ala Trp Ser Asn Val Leu Arg Gly Met Gly Gly Ala Phe Val Leu
```

```
                    275                 280                 285

Val Leu Tyr Asp Glu Ile Lys Lys Tyr Thr
    290                 295

<210> SEQ ID NO 33
<211> LENGTH: 298
<212> TYPE: PRT
<213> ORGANISM: Homo sapien

<400> SEQUENCE: 33

Met Thr Glu Gln Ala Ile Ser Phe Ala Lys Asp Phe Leu Ala Gly Gly
  1               5                  10                  15

Ile Ala Ala Ile Ser Lys Thr Ala Val Ala Pro Ile Glu Arg Val
             20                  25                  30

Lys Leu Leu Leu Gln Val Gln His Ala Ser Lys Gln Ile Ala Ala Asp
             35                  40                  45

Lys Gln Tyr Lys Gly Ile Val Asp Cys Ile Val Arg Ile Pro Lys Glu
     50                  55                  60

Gln Gly Val Leu Ser Phe Trp Arg Gly Asn Leu Ala Asn Val Ile Arg
 65                  70                  75                  80

Tyr Phe Pro Thr Gln Ala Leu Asn Phe Ala Phe Lys Asp Lys Tyr Lys
                 85                  90                  95

Gln Ile Phe Leu Gly Gly Val Asp Lys His Thr Gln Phe Trp Arg Tyr
            100                 105                 110

Phe Ala Gly Asn Leu Ala Ser Gly Gly Ala Ala Gly Ala Thr Ser Leu
            115                 120                 125

Cys Phe Val Tyr Pro Leu Asp Phe Ala Arg Thr Arg Leu Ala Ala Asp
    130                 135                 140

Val Gly Lys Ser Gly Thr Glu Arg Glu Phe Arg Gly Leu Gly Asp Cys
145                 150                 155                 160

Leu Val Lys Ile Thr Lys Ser Asp Gly Ile Arg Gly Leu Tyr Gln Gly
                165                 170                 175

Phe Ser Val Ser Val Gln Gly Ile Ile Ile Tyr Arg Ala Ala Tyr Phe
            180                 185                 190

Gly Val Tyr Asp Thr Ala Lys Gly Met Leu Pro Asp Pro Lys Asn Thr
        195                 200                 205

His Ile Val Val Ser Trp Met Ile Ala Gln Thr Val Thr Ala Val Ala
    210                 215                 220

Gly Val Val Ser Tyr Pro Phe Asp Thr Val Arg Arg Arg Met Met Met
225                 230                 235                 240

Gln Ser Gly Arg Lys Gly Ala Asp Ile Met Tyr Thr Gly Thr Val Asp
                245                 250                 255

Cys Trp Arg Lys Ile Phe Arg Asp Glu Gly Gly Lys Ala Phe Phe Lys
            260                 265                 270

Gly Ala Trp Ser Asn Val Leu Arg Gly Met Gly Gly Ala Phe Val Leu
        275                 280                 285

Val Leu Tyr Asp Glu Leu Lys Lys Val Ile
    290                 295

<210> SEQ ID NO 34
<211> LENGTH: 41
<212> TYPE: DNA
<213> ORGANISM: Artificial Sequence
<220> FEATURE:
<223> OTHER INFORMATION: Primer for PCR amplification of human ANT3 for
      expression construct
```

```
-continued

<400> SEQUENCE: 34
ttaatggtac catgacggaa caggccatct ccttcgccaa a                    41

<210> SEQ ID NO 35
<211> LENGTH: 42
<212> TYPE: DNA
<213> ORGANISM: Artificial Sequence
<220> FEATURE:
<223> OTHER INFORMATION: Primer for PCR amplification of human ANT3 for
      expression construct

<400> SEQUENCE: 35
ttatactcga gttagatcac cttcttgagc tcgtcgtaca gg                   42

<210> SEQ ID NO 36
<211> LENGTH: 30
<212> TYPE: DNA
<213> ORGANISM: Artificial Sequence
<220> FEATURE:
<223> OTHER INFORMATION: Primer for PCR amplification of EYFP

<400> SEQUENCE: 36
gggcccctcg agatggtgag caagggcgag                                 30

<210> SEQ ID NO 37
<211> LENGTH: 33
<212> TYPE: DNA
<213> ORGANISM: Artificial Sequence
<220> FEATURE:
<223> OTHER INFORMATION: Primer for PCR amplification of EYFP

<400> SEQUENCE: 37
gggccctcta gactacttgt acagctcgtc cat                             33
```

PRODUCTION OF ADENINE NUCLEOTIDE TRANSLOCATOR (ANT), NOVEL ANT LIGANDS AND SCREENING ASSAYS THEREFOR

CROSS-REFERENCES TO RELATED APPLICATIONS

This application is a divisional of pending U.S. patent application Ser. No. 09/393,441, filed Sep. 8, 1999, which application is a continuation-in-part of U.S. patent application Ser. No. 09/185,904, filed Nov. 3, 1998, and which applications are incorporated herein by reference in their entirety.

FIELD OF THE INVENTION

The invention relates to the adenine nucleotide translocator (ANT) protein that is found in mitochondria of eukaryotic cells. More particularly, the invention relates to the production of ANT polypeptides and ANT fusion proteins using recombinant DNA technology; to novel labeled ligands for ANT proteins; and to assays useful for identifying and isolating ANT proteins and for screening compounds that interact with ANT, including high throughput screening.

BACKGROUND OF THE INVENTION

Mitochondria are the main energy source in cells of higher organisms, and these organelles provide direct and indirect biochemical regulation of a wide array of cellular respiratory, oxidative and metabolic processes. These include electron transport chain (ETC) activity, which drives oxidative phosphorylation to produce metabolic energy in the form of adenosine triphosphate (ATP), and which also underlies a central mitochondrial role in intracellular calcium homeostasis.

Mitochondrial ultrastructural characterization reveals the presence of an outer mitochondrial membrane that serves as an interface between the organelle and the cytosol, a highly folded inner mitochondrial membrane that appears to form attachments to the outer membrane at multiple sites, and an intermembrane space between the two mitochondrial membranes. The subcompartment within the inner mitochondrial membrane is commonly referred to as the mitochondrial matrix. (For a review, see, e.g., Ernster et al., 1981 *J. Cell Biol.* 91:227s.) The cristae, originally postulated to occur as infoldings of the inner mitochondrial membrane, have recently been characterized using three-dimensional electron tomography as also including tube-like conduits that may form networks, and that can be connected to the inner membrane by open, circular (30 nm diameter) junctions (Perkins et al., 1997, *Journal of Structural Biology* 119:260). While the outer membrane is freely permeable to ionic and non-ionic solutes having molecular weights less than about ten kilodaltons, the inner mitochondrial membrane exhibits selective and regulated permeability for many small molecules, including certain cations, and is impermeable to large (>~10 kDa) molecules.

Altered or defective mitochondrial activity, including but not limited to failure at any step of the ETC, may result in catastrophic mitochondrial collapse that has been termed "permeability transition" (PT) or "mitochondrial permeability transition" (MPT). According to generally accepted theories of mitochondrial function, proper ETC respiratory activity requires maintenance of an electrochemical potential ($\Delta\psi m$) in the inner mitochondrial membrane by a coupled chemiosmotic mechanism. Altered or defective mitochondrial activity may dissipate this membrane potential, thereby preventing ATP biosynthesis and halting the production of a vital biochemical energy source. In addition, mitochondrial proteins such as cytochrome c may leak out of the mitochondria after permeability transition and may induce the genetically programmed cell suicide sequence known as apoptosis or programmed cell death (PCD).

MPT may result from direct or indirect effects of mitochondrial genes, gene products or related downstream mediator molecules and/or extramitochondrial genes, gene products or related downstream mediators, or from other known or unknown causes. Loss of mitochondrial potential therefore may be a critical event in the progression of diseases associated with altered mitochondrial function, including degenerative diseases.

Mitochondrial defects, which may include defects related to the discrete mitochondrial genome that resides in mitochondrial DNA and/or to the extramitochondrial genome, which includes nuclear chromosomal DNA and other extramitochondrial DNA, may contribute significantly to the pathogenesis of diseases associated with altered mitochondrial function. For example, alterations in the structural and/or functional properties of mitochondrial components comprised of subunits encoded directly or indirectly by mitochondrial and/or extramitochondrial DNA, including alterations deriving from genetic and/or environmental factors or alterations derived from cellular compensatory mechanisms, may play a role in the pathogenesis of any disease associated with altered mitochondrial function. A number of degenerative diseases are thought to be caused by, or to be associated with, alterations in mitochondrial function. These include Alzheimer's Disease (AD), diabetes mellitus, Parkinson's Disease; Huntington's disease; dystonia, Leber's hereditary optic neuropathy; schizophrenia; mitochondrial encephalopathy, lactic acidosis, and stroke (MELAS); cancer; psoriasis; hyperproliferative disorders; mitochondrial diabetes and deafness (MIDD) and myoclonic epilepsy ragged red fiber syndrome. The extensive list of additional diseases associated with altered mitochondrial function continues to expand as aberrant mitochondrial or mitonuclear activities are implicated in particular disease processes.

A hallmark pathology of AD and potentially other diseases associated with altered mitochondrial function is the death of selected cellular populations in particular affected tissues, which results from apoptosis (also referred to as "programmed cell death" or PCD) according to a growing body of evidence. Mitochondrial dysfunction is thought to be critical in the cascade of events leading to apoptosis in various cell types (Kroemer et al., *FASEB J.* 9:1277–87, 1995), and may be a cause of apoptotic cell death in neurons of the AD brain. Altered mitochondrial physiology may be among the earliest events in PCD (Zamzami et al., *J. Exp. Med.* 182:367–77, 1995; Zanizami et al., *J. Exp. Med.* 181:1661–72, 1995) and elevated reactive oxygen species (ROS) levels that result from such altered mitochondrial function may initiate the apoptotic cascade (Ausserer et al., *Mol. Cell. Biol.* 14:5032–42, 1994).

Thus, in addition to their role in energy production in growing cells, mitochondria (or, at least, mitochondrial components) participate in apoptosis (Newmeyer et al., 1994, *Cell* 79:353–364; Liu et al., 1996, *Cell* 86:147–157). Apoptosis is apparently also required for, inter alia, normal development of the nervous system and proper functioning of the immune system. Moreover, some disease states are thought to be associated with either insufficient (e.g., cancer, autoimmune diseases) or excessive (e.g., stroke damage, AD-associated neurodegeneration) levels of apoptosis. For general reviews of apoptosis, and the role of mitochondria therein, see Green and Reed (1998, *Science* 281:1309–1312), Green (1998, *Cell* 94:695–698) and Kromer (1997, *Nature Medicine* 3:614–620). Hence, agents that effect apoptotic events, including those associated with mitochondrial components, might have a variety of palliative, prophylactic and therapeutic uses.

The adenine nucleotide translocator (ANT), a nuclear encoded polypeptide that is a major component of the inner mitochondrial membrane, is responsible for mediating transport of ADP and ATP across the mitochondrial inner membrane. For example, ANT is believed to mediate stoichiometric ATP/proton exchange across the inner mitochondrial membrane, and ANT inhibitors (such as atractyloside or bongkrekic acid) induce MPT under certain conditions. Three human ANT isoforms have been described that differ in their tissue expression patterns and other mammalian ANT homologues have been described. (See, e.g., Wallace et al., 1998 in *Mitochondria & Free Radicals in Neurodegenerative Diseases*, Beal, Howell and Bodis-Wollner, Eds., Wiley-Liss, New York, pp. 283–307, and references cited therein.) ANT has also been implicated as an important molecular component of the mitochondrial permeability transition pore, a $Ca^{2+}$-regulated inner membrane channel that, as described above, plays an important modulating role in apoptotic processes.

As inner mitochondrial membrane proteins are believed to possess multiple hydrophobic membrane spanning domains, ANT polypeptides may exhibit, inter alia, poor intracellular solubility, toxic accumulations and/or the formation of inclusion bodies and other deleterious effects on respiratory homeostasis within a host cell due to ANT biological activity. Consequently, those having ordinary skill in the art have heretofore been unable to produce ANT reliably or in sufficient quantities for a variety of uses, such as those provided herein. Because of the significance of mitochondria to respiratory, metabolic and apoptotic processes, and in view of the prominent role played by ANT in these and other mitochondrial activities, there is clearly a need for compositions and methods that permit the production of ANT proteins, including ANT fusion proteins; for novel ANT ligands; for methods to identify and isolate ANT proteins; and for methods of identifying and isolating agents that interact with ANT.

The present invention fulfills these needs and provides other related advantages. These and other aspects of the present invention will become evident upon reference to the following detailed description and attached drawings. In addition, various references are set forth below which describe in more detail certain procedures or compositions (e.g., plasmids, vectors, etc.), and are therefore incorporated by reference in their entireties.

SUMMARY OF THE INVENTION

In its various aspects and embodiments the invention is directed to:

A recombinant expression construct comprising at least one regulated promoter operably linked to a first nucleic acid encoding an adenine nucleotide translocator polypeptide; further comprising at least one additional nucleic acid sequence that regulates transcription; wherein the additional nucleic acid sequence that regulates transcription encodes a repressor of said regulated promoter; wherein the adenine nucleotide translocator polypeptide comprises a human adenine nucleotide translocator polypeptide; wherein the human adenine nucleotide translocator polypeptide is ANT1; wherein the human adenine nucleotide translocator polypeptide is ANT2; wherein the human adenine nucleotide translocator polypeptide is ANT3; wherein the adenine nucleotide translocator polypeptide is expressed as a fusion protein with a polypeptide product of a second nucleic acid sequence; wherein the polypeptide product of said second nucleic acid sequence is an enzyme; wherein said fusion protein localizes to membranes; wherein said membranes are mitochondrial membranes; wherein the adenine nucleotide translocator polypeptide is expressed as a fusion protein with at least one product of a second nucleic acid sequence encoding a polypeptide cleavable by a protease, said adenine nucleotide translocator polypeptide being separable from the fusion protein by cleavage with the protease. A host cell comprising a recombinant expression construct as provided wherein the host cell is a prokaryotic cell; wherein the host cell is a eukaryotic cell; wherein the eukaryotic cell is selected from the group consisting of a yeast cell, an insect cell and a mammalian cell; wherein the insect cell is an Sf9 cell or a *Trichoplusia ni* cell; at lacks at least one isoform of an endogenous adenine nucleotide translocator; in which expression of at least one gene encoding an endogenous adenine nucleotide translocator isoform is substantially impaired.

A recombinant expression construct comprising at least one promoter operably linked to a nucleic acid molecule comprising a first nucleic acid sequence and a second nucleic acid sequence, said first nucleic acid sequence encoding an animal adenine nucleotide translocator polypeptide wherein the adenine nucleotide translocator polypeptide is expressed as a fusion protein with a polypeptide product of said second nucleic acid sequence; wherein the polypeptide product of said second nucleic acid sequence is an enzyme; wherein said fusion protein localizes to membranes; wherein said membranes are mitochondrial membranes; further comprising at least one additional nucleic acid sequence that regulates transcription; wherein the additional nucleic acid sequence that regulates transcription encodes a repressor of said promoter; wherein the adenine nucleotide translocator polypeptide comprises a human adenine nucleotide translocator polypeptide; wherein the human adenine nucleotide translocator polypeptide is ANT1; wherein the human adenine nucleotide translocator polypeptide is ANT2; wherein the human adenine nucleotide translocator polypeptide is ANT3; wherein the adenine nucleotide translocator polypeptide is expressed as a fusion protein with at least one product of a second nucleic acid sequence encoding a polypeptide cleavable by a protease, said adenine nucleotide translocator polypeptide being separable from the fusion protein by cleavage with the protease; a host cell comprising a recombinant expression construct as just described; wherein the host cell is a prokaryotic cell; wherein the host cell is a eukaryotic cell, wherein the eukaryotic cell is selected from the group consisting of a yeast cell, an insect cell and a mammalian cell; wherein the insect cell is an Sf9 cell or a *Trichoplusia ni* cell, that lacks at least one isoform of an endogenous adenine nucleotide translocator; in which expression of at least one gene encoding an endogenous adenine nucleotide translocator isoform is substantially impaired; wherein the expression construct is a recombinant viral expression construct.

A method of producing a recombinant adenine nucleotide translocator polypeptide, comprising; culturing a host cell comprising a recombinant expression construct comprising at least one regulated promoter operably linked to a first nucleic acid encoding an adenine nucleotide translocator polypeptide.

A method of producing a recombinant adenine nucleotide translocator polypeptide, comprising culturing a host cell comprising a recombinant expression construct comprising at least one promoter operably linked to a nucleic acid molecule comprising a first nucleic acid sequence and a second nucleic acid sequence, said first nucleic acid sequence encoding an animal adenine nucleotide translocator polypeptide wherein the adenine nucleotide translocator polypeptide is expressed as a fusion protein with a polypeptide product of said second nucleic acid sequence.

A method of producing a recombinant adenine nucleotide translocator polypeptide, comprising culturing a host cell infected with the recombinant viral expression construct as provided above.

An ANT polypeptide produced by the methods just described.

An isolated human adenine nucleotide translocator polypeptide; wherein the human adenine nucleotide translocator polypeptide is recombinant ANT1 or a variant or fragment thereof, wherein the human adenine nucleotide translocator polypeptide is recombinant ANT2 or a variant or fragment thereof, wherein the human adenine nucleotide translocator polypeptide is recombinant ANT3 or a variant or fragment thereof.

An isolated human adenine nucleotide translocator fusion protein comprising an adenine translocator polypeptide fused to at least one additional polypeptide sequence; wherein said one additional polypeptide sequence is an enzyme sequence or a variant or fragment thereof; wherein said fusion protein localizes to membranes; wherein said membranes are mitochondrial membranes.

An isolated human adenine nucleotide translocator fusion protein comprising an adenine translocator polypeptide fused to at least one additional polypeptide sequence cleavable by a protease, said adenine nucleotide translocator polypeptide being separable from the fusion protein by cleavage with the protease.

An isolated adenine nucleotide translocator fusion protein comprising a first polypeptide that is an animal adenine translocator polypeptide fused to at least one additional polypeptide sequence; wherein said one additional polypeptide sequence is an enzyme sequence or a variant or fragment thereof; that localizes to membranes; wherein said membranes are mitochondrial membranes.

An isolated recombinant animal adenine nucleotide translocator fusion protein comprising an adenine translocator polypeptide fused to at least one additional polypeptide sequence cleavable by a protease, said adenine nucleotide translocator polypeptide being separable from the fusion protein by cleavage with the protease; wherein the additional polypeptide sequence is a polypeptide having affinity for a ligand.

A method for determining the presence of an ANT polypeptide in a biological sample comprising contacting a biological sample suspected of containing an ANT polypeptide with an ANT ligand under conditions and for a time sufficient to allow binding of the ANT ligand to an ANT polypeptide; and detecting the binding of the ANT ligand to an ANT polypeptide, and therefrom determining the presence of an ANT polypeptide in said biological sample, wherein the adenine nucleotide translocator polypeptide comprises a human adenine nucleotide translocator polypeptide; wherein the human adenine nucleotide translocator polypeptide is ANT1, wherein the human adenine nucleotide translocator polypeptide is ANT2, wherein the human adenine nucleotide translocator polypeptide is ANT3; wherein the ANT ligand comprises atractyloside substituted at 6' hydroxyl to form an atractyloside derivative wherein the atractyloside is detectably substituted at the 6' hydroxyl to form a detectable atractyloside derivative; wherein the detectable atractyloside derivative comprises a radiolabeled substituent; wherein the radiolabeled substituent is selected from the group consisting of $^{125}$I, $^{131}$I, $^{3}$H, $^{14}$H, $^{14}$C and $^{35}$S; wherein the detectable atractyloside derivative comprises a fluorescent substituent; wherein the ANT ligand further comprises a Eu$^{3+}$ atom complexed to the atractyloside derivative; wherein the detectable atractyloside derivative comprises covalently bound biotin; wherein the atractyloside molecule is substituted at 6' hydroxyl with an amine or an amine containing functionality to form an amine modified atractyloside derivative; wherein the atractyloside molecule is a carboxyatractyloside molecule that is substituted at 6' hydroxyl to form an atractyloside derivative that is a carboxyatractyloside derivative.

A method for isolating ANT from a biological sample, comprising contacting a biological sample suspected of containing an ANT polypeptide with an ANT ligand under conditions and for a time sufficient to allow binding of the ANT ligand to an ANT polypeptide; and recovering the ANT polypeptide, and thereby isolating ANT from a biological sample; wherein the ANT ligand is covalently bound to a solid phase; wherein the ANT ligand is non-covalently bound to a solid phase.

A method for identifying an agent that binds to an ANT polypeptide, comprising contacting a candidate agent with a host cell expressing at least one recombinant ANT polypeptide under conditions and for a time sufficient to permit binding of the agent to said recombinant ANT polypeptide; and detecting binding of said agent to the recombinant ANT; wherein the host cell is a prokaryotic cell; wherein the prokaryotic cell is an *E. coli* cell, wherein the host cell is a eukaryotic cell; wherein the eukaryotic cell is selected from the group consisting of a yeast cell, an insect cell and a mammalian cell, wherein the insect cell is an Sf9 cell or a *Trichoplusia ni* cell; wherein the host cell lacks at least one isoform of an endogenous adenine nucleotide translocator; wherein host cell expression of at least one gene encoding an endogenous adenine nucleotide translocator isoform is substantially impaired.

A method for identifying an agent that binds to an ANT polypeptide, comprising contacting a candidate agent with a biological sample containing at least one recombinant ANT polypeptide under conditions and for a time sufficient to permit binding of the agent to said ANT polypeptide; and detecting binding of said agent to the recombinant ANT polypeptide.

A method for identifying an agent that interacts with an ANT polypeptide comprising contacting a biological sample containing recombinant ANT with a detectable ANT ligand in the presence of a candidate agent; and comparing binding of the detectable ANT ligand to recombinant ANT in the absence of said agent to binding of the detectable ANT ligand to recombinant ANT in the presence of said agent, and therefrom identifying an agent that interacts with an ANT polypeptide.

An ANT ligand comprising atractyloside substituted at the 6' hydroxyl to form an atractyloside derivative; wherein the atractyloside is detectably substituted at the 6' hydroxyl to form a detectable atractyloside derivative; wherein the detectable atractyloside derivative comprises a radiolabeled substituent; wherein the radiolabeled substituent is selected from the group consisting of $^{125}$I, $^{131}$I, $^{3}$H, $^{14}$C and $^{35}$S; wherein the detectable atractyloside derivative comprises a fluorescent substituent; further comprising a Eu$^{3+}$ atom complexed to the atractyloside derivative; wherein the detectable atractyloside derivative comprises covalently bound biotin; wherein the atractyloside molecule is substituted at 6' hydroxyl with an amine or an amine containing functionality to form an amine modified atractyloside derivative; wherein the atractyloside molecule is a carboxyatractyloside molecule that is substituted at 6' hydroxyl to form an atractyloside derivative that is a carboxyatractyloside derivative.

An ANT ligand having the following structure (I):

$$(I)$$

including stereoisomers and pharmaceutically acceptable salts thereof, wherein $R_1$, $R_2$ and $R_3$ are as identified below.

An assay plate for high throughput screening of candidate agents that bind to at least one ANT polypeptide, comprising an assay plate having a plurality of wells, each of said wells further comprising at least one immobilized recombinant ANT polypeptide or a variant or fragment thereof.

A method of targeting a polypeptide of interest to a mitochondrial membrane, comprising expressing a recombinant expression construct encoding a fusion protein in a host cell, said construct comprising at least one regulated promoter operably linked to a nucleic acid molecule comprising a first nucleic acid sequence and a second nucleic acid sequence, said first nucleic acid sequence encoding an adenine nucleotide translocator polypeptide that is expressed as a fusion protein with a polypeptide product of said second nucleic acid sequence, wherein said second nucleic acid sequence encodes the polypeptide of interest.

A method of targeting a polypeptide of interest to a mitochondrial membrane, comprising expressing a recombinant expression construct encoding a fusion protein in a host cell, said construct comprising at least one promoter operably linked to a nucleic acid molecule comprising a first nucleic acid sequence and a second nucleic acid sequence, said first nucleic acid sequence encoding an animal adenine nucleotide translocator polypeptide that is expressed as a fusion protein with a polypeptide product of said second nucleic acid sequence, wherein said second nucleic acid sequence encodes the polypeptide of interest; a pharmaceutical composition comprising an ANT ligand as just described.

A pharmaceutical composition comprising an agent that binds to an ANT polypeptide identified as just described. A pharmaceutical composition comprising an agent that binds to an ANT polypeptide identified as described above. A pharmaceutical composition comprising an agent that interacts with an ANT polypeptide identified above. A method of treatment comprising administering to a subject any one of the just described the pharmaceutical compositions.

BRIEF DESCRIPTION OF THE DRAWINGS

FIG. 1 shows the nucleotide sequences of the coding regions of human ANT1 ("ANT1m"), human ANT2 ("ANT2m") and human ANT3 ("ANT3m"). These sequences are provided in SEQ ID NOs:1, 2 and 3, respectively. FIG. 1A shows the nucleotide sequences of residues 1–477 of ANT1m, residues 1–480 of ANT2m and residues 1480 of ANT3m. FIG. 1B shows the nucleotide sequences of residues 478–894 of ANT1m, residues 481–897 of ANT2m and residues 481–897 of ANT3m.

FIG. 2 shows the polypeptide sequences of human ANT1 ("ANT1p"), human ANT2 ("ANT2p") and human ANT3 ("ANT3p"). These sequences are provided in SEQ ID NOs:31, 32 and 33, respectively.

DETAILED DESCRIPTION OF THE INVENTION

Figure 3:
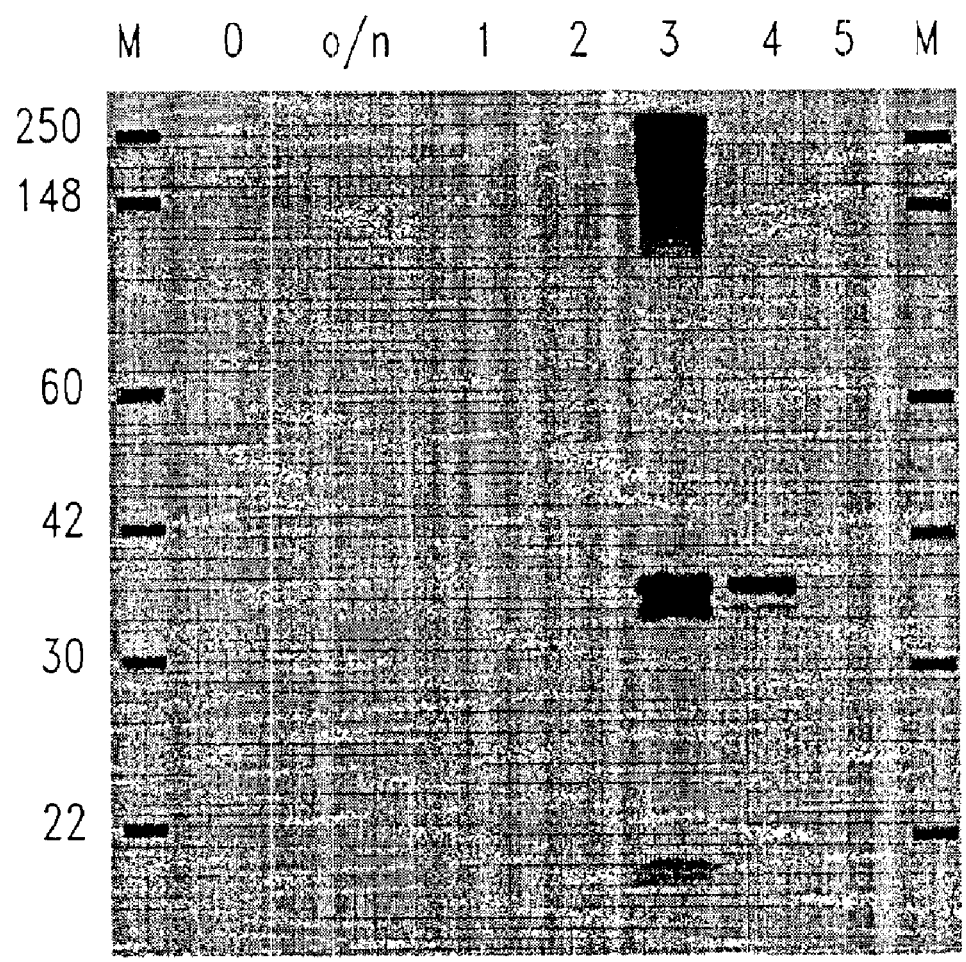
FIG. 3 shows induction of His-Tagged, XPRESS™-epitope containg huANT3 protein in *E. coli* as determined by Western analysis.

The present invention is directed generally toward adenine nucleotide translocator (ANT) polypeptides, which as provided herein may refer to any ANT isoform; to expression constructs containing nucleic acids encoding ANT and to natural and synthetic small molecules that interact with ANT, including ANT binding ligands. The present invention relates in part to the unexpected findings that bacterial, insect, yeast or mammalian expression systems can be designed for reliable production of recombinant human ANT polypeptides in significant quantities. In certain aspects the invention provides compositions and methods for producing recombinant ANT polypeptides that employ regulated promoters, and in certain of these and other aspects the invention provides compositions and methods for producing recombinant ANT polypeptides that are ANT fusion proteins. In certain preferred embodiments, the design of such expression systems includes the use of a host cell that lacks endogenous ANT or in which endogenous ANT gene expression is substantially impaired, as provided herein.

The present invention thus also pertains in part to methods for producing and isolating recombinant ANT polypeptides, including human ANT polypeptides and in preferred embodiments human ANT3 polypeptides, that may then be used in various binding assays and screening assays and the like. In view of the surprising observation that expression of recombinant human ANT polypeptides can be achieved at levels enabling such uses of these ANT polypeptide products, the present invention provides assays (including high throughput assays) for identifying agents that bind to recombinant human ANT. Accordingly, the present invention further relates in part to novel human ANT ligands, the synthesis, selection and characterization of which would heretofore have not been possible given the need for expressed recombinant ANT polypeptides to use in binding assays. The invention also pertains to agents that interact with ANT, including agents that enhance or impair any ANT functions known to the art, including but not limited to those described herein, and to incorporation of such agents into pharmaceutical compositions and their use in therapeutic methods.

As dicussed above, the present invention relates in part to the unexpected finding that recombinant adenine nucleotide translocator (ANT) polypeptides, which includes full length ANT proteins and polypeptides, fragments and variants thereof, and further includes ANT fusion proteins as provided herein, can be produced in useful amounts by using a recombinant expression vector having a regulatory nucleic acid operably linked to a nucleic acid encoding ANT. In particular, the invention provides compositions and methods for producing recombinant ANT polypeptides through the use of a regulated promoter; the invention also provides recombinant ANT polypeptides that are ANT fusion proteins.

The invention also pertains to compositions and methods to identify the presence of ANT polypeptides and to isolate recombinant ANT, and in addition to screening assays for compounds that interact with ANT. Accordingly, the invention provides certain advantages with regard to regulation of mitochondrial function, and in particular regulation of the mitochondrial permeability "pore". By way of background, four of the five multisubunit protein complexes (Complexes I, III, IV and V) that mediate ETC activity are localized to the inner mitochondrial membrane, which is the most protein rich of biological membranes in cells (75% by weight); the remaining ETC complex (Complex II) is situated in the matrix. ANT represents the most abundant of the inner mitochondrial membrane proteins. In at least three distinct chemical reactions known to take place within the ETC, positively-charged protons are moved from the mitochondrial matrix, across the inner membrane, to the intermembrane space. This disequilibrium of charged species creates an electrochemical potential of approximately 220 mV referred to as the "protonmotive force" (PMF), which is often represented by the notation $\Delta\psi$ or $\Delta\psi m$ and represents the sum of the electric potential and the pH differential across the inner mitochondrial membrane (see, e.g., Ernster et al., 1981 *J. Cell Biol.* 91:227s and references cited therein).

This membrane potential drives ANT-mediated stoichiometric exchange of adenosine triphosphate (ATP) and adenosine diphosphate (ADP) across the inner mitochondrial membrane, and provides the energy contributed to the phosphate bond created when ADP is phosphorylated to yield ATP by ETC Complex V, a process that is "coupled" stoichiometrically with transport of a proton into the matrix. Mitochondrial membrane potential, $\Delta\psi m$, is also the driving force for the influx of cytosolic $Ca^{2+}$ into the mitochondrion. Under normal metabolic conditions, the inner membrane is impermeable to proton movement from the intermembrane space into the matrix, leaving ETC Complex V as the sole means whereby protons can return to the matrix. When, however, the integrity of the inner mitochondrial membrane is compromised, as occurs during MPT that may accompany a disease associated with altered mitochondrial function, protons are able to bypass the conduit of Complex V without generating ATP, thereby "uncoupling" respiration because electron transfer and associated proton pumping yields no ATP. Thus, mitochondrial permeability transition involves the opening of a mitochondrial membrane "pore", a process by which, inter alia, the ETC and ATP synthesis are uncoupled, $\Delta\psi m$ collapses and mitochondrial membranes lose the ability to selectively regulate permeability to solutes both small (e.g., ionic $Ca^{2+}$, $Na^+$, $K^+$, $H^+$) and large (e.g., proteins).

Without wishing to be bound by theory, it is unresolved whether this pore is a physically discrete conduit that is formed in mitochondrial membranes, for example by assembly or aggregation of particular mitochondrial and/or cytosolic proteins and possibly other molecular species, or whether the opening of the "pore" may simply represent a general increase in the porosity of the mitochondrial membrane.

MPT may also be induced by compounds that bind one or more mitochondrial molecular components. Such compounds include, but are not limited to, atractyloside and bongkrekic acid, which are known to bind to ANT. Methods of determining appropriate amounts of such compounds to induce MPT are known in the art (see, e.g., Beutner et al., 1998 *Biochim. Biophys. Acta* 1368:7; Obatomi and Bach, 1996 *Toxicol. Lett.* 89:155; Green and Reed, 1998 *Science* 281:1309; Kroemer et al., 1998 Annu. Rev. Physiol. 60:619, and references cited therein). Thus certain mitochondrial molecular components, such as ANT, may contribute to the MPT mechanism. As noted above, it is believed that adenine nucleotide translocator (ANT) mediates ATP/proton exchange across the inner mitochondrial membrane, and that ANT inhibitors such as atractyloside or bongkrekic acid induce MPT under certain conditions. Hence, it is desirable to obtain ANT in sufficient quantities for structural and functional assays that provide, for example, ANT ligands and other agents that interact with ANT, which will be useful for therapeutic management of mitochondrial pore activity. See also U.S. Ser. No. 09/161,172, entitled "Compositions and Methods for Identifying Agents that Alter Mitochondrial Permeability Transition Pores", which is hereby incorporated by reference.

The compositions and methods of the present invention can be adapted to any prokaryotic or eukaryotic ANT, including plant and animal ANTs, which may further include, for example, yeast, vertebrate, mammalian, rodent, primate and human ANTs, for which amino acid sequences and/or encoding nucleic acids will be known to those familiar with the art. Three human ANT isoforms have been described that differ in their tissue expression patterns. (Stepien et al., 1992 *J. Biol. Chem.* 267:14592; see also Wallace et al., 1998 in *Mitochondria & Free Radicals in Neurodegenerative Diseases*, Beal, Howell and Bodis-Wollner, Eds., Wiley-Liss, New York, pp. 283–307, and references cited therein.) Nucleic acid sequences for cDNAs encoding these three human ANT isoforms have been reported (FIG. 1; See Neckelmann et al., *Proc. Nat'l. Acad. Sci. U.S.A.* 84:7580–7584 (1987) for huANT1 cDNA [SEQ ID NO:1], Battini et al., *J. Biol. Chem.* 262:4355–4359 (1987) for huANT2 cDNA [SEQ ID NO:2], and Cozens et al., *J. Mol. Biol.* 206:261–280 (1989) for huANT3 cDNA [SEQ ID NO:3]; see FIG. 2 for amino acid sequences of huANT1 [SEQ ID NO:31] huANT2 [SEQ ID NO:32] and huANT3 [SEQ ID NO:33].), and ANT gene sequences have been determined for a number of species (See, e.g., Li et al., 1989 *J. Biol. Chem.* 264:13998 for huANT1 genomic DNA; Liew et al. GenBank Acc. #N86710 for huANT2; Shinohara et al., 1993 *Biochim. Biophys. Acta* 1152:192 for rat ANT gene; for others see also, e.g., Ku et al., 1990 *J. Biol. Chem.* 265:16060; Adams et al., 1991 Science 252:1651; and WO 98/19714.). ANT sequences among mammalian species are highly conserved; for example, at the amino acid level murine ANT1 and ANT2 exhibit 98% sequence identity with human ANT2. Full length amino acid sequences of at least 29 ANT proteins have been reported to date from a variety of animal and plant species, with most of these deduced from nucleic acid sequences. (Fiore et al., 1998 *Biochimie* 80:137–150).

The present invention further relates to nucleic acids which hybridize to ANT encoding polynucleotide sequences as provided herein, as incorporated by reference or as will be readily apparent to those familiar with the art, if there is at least 70%, preferably at least 90%, and more preferably at least 95% identity between the sequences. The present invention particularly relates to nucleic acids which hybridize under stringent conditions to the ANT encoding nucleic acids referred to herein. As used herein, the term "stringent conditions" means hybridization will occur only if there is at least 95% and preferably at least 97% identity between the sequences. The nucleic acids which hybridize to ANT encoding nucleic acids referred to herein, in preferred embodiments, encode polypeptides which either retain substantially the same biological function or activity as the ANT polypeptides encoded by the cDNAs of FIG. 1 [SEQ ID NOS:1, 2 and 3], or the deposited expression constructs.

As used herein, to "hybridize" under conditions of a specified stringency is used to describe the stability of hybrids formed between two single-stranded nucleic acid molecules. Stringency of hybridization is typically expressed in conditions of ionic strength and temperature at which such hybrids are annealed and washed. Typically "high", "medium" and "low" stringency encompass the following conditions or equivalent conditions thereto: high stringency: 0.1× SSPE or SSC, 0.1% SDS, 65° C., medium stringency: 0.2× SSPE or SSC, 0.1% SDS, 50° C.; and low stringency: 1.0× SSPE or SSC, 0.1% SDS, 50° C.

The deposits referred to herein will be maintained under the terms of the Budapest Treaty on the International Recognition of the Deposit of Micro-organisms for purposes of Patent Procedure. These deposits are provided merely as convenience to those of skill in the art and are not an admission that a deposit is required under 35 U.S.C. § 112. The sequences of the nucleic acids contained in the deposited materials, as well as the amino acid sequences of the polypeptides encoded thereby, are incorporated herein by reference and are controlling in the event of any conflict with any description of sequences herein. A licensee may be required to make, use or sell the deposited materials, and no such license is hereby granted.

Nucleic Acids

The nucleic acids of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. A coding sequence which encodes an ANT polypeptide for use according to the invention may be identical to the coding sequence known in the art for any given ANT, as described above and, for example, as shown for human ANT1 [SEQ ID NO:1], human ANT2 [SEQ ID NO:2] and human ANT3 [SEQ ID NO:3] in FIG. 1, or to that of any deposited clone, or may be a different coding sequence, which, as a result of the redundancy or degeneracy of the genetic code, encodes the same ANT polypeptide as, for example, the cDNAs of FIG. 1 or the deposited expression constructs.

The nucleic acids which encode ANT polypeptides, for example the human ANT polypeptides having the amino acid sequences of FIG. 2 [SEQ ID NOS:31–33] or any other ANT polypeptides for use according to the invention, or for the ANT polypeptides encoded by the deposited constructs may include, but are not limited to: only the coding sequence for the ANT polypeptide; the coding sequence for the ANT polypeptide and additional coding sequence; the coding sequence for the ANT polypeptide (and optionally additional coding sequence) and non-coding sequence, such as introns or non-coding sequences 5' and/or 3' of the coding sequence for the ANT polypeptide, which for example may further include but need not be limited to one or more regulatory nucleic acid sequences that may be a regulated or regulatable promoter, enhancer, other transcription regulatory sequence, repressor binding sequence, translation regulatory sequence or any other regulatory nucleic acid sequence. Thus, the term "nucleic acid encoding an ANT polypeptide" encompasses a nucleic acid which includes only coding sequence for the polypeptide as well as a nucleic acid which includes additional coding and/or non-coding sequence(s).

The present invention further relates to variants of the herein described nucleic acids which encode for fragments, analogs and derivatives of an ANT polypeptide, for example the human ANT1, ANT2 and ANT3 polypeptides having the deduced amino acid sequences of FIG. 2 [SEQ ID NOS:31–33] or any ANT polypeptide, including ANT polypeptides encoded by the cDNAs of the deposited expression constructs. The variants of the nucleic acids encoding ANTs may be naturally occurring allelic variants of the nucleic acids or non-naturally occurring variants. As is known in the art, an allelic variant is an alternate form of a nucleic acid sequence which may have at least one of a substitution, a deletion or an addition of one or more nucleotides, any of which does not substantially alter the function of the encoded ANT polypeptide. Thus, for example, the present invention includes nucleic acids encoding the same ANT polypeptides as shown in FIG. 2 [SEQ ID NOS:31–33], or the same ANT polypeptides encoded by the cDNAs of the deposited expression constructs, as well as variants of such nucleic acids, which variants encode a fragment, derivative or analog of any of the polypeptides of FIG. 2 (SEQ ID NO:2) or the polypeptides encoded by the cDNAs of the deposited expression constructs.

Variants and derivatives of ANT may be obtained by mutations of nucleotide sequences encoding ANT polypeptides. Alterations of the native amino acid sequence may be accomplished by any of a number of conventional methods. Mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures can be employed to provide an altered gene wherein predetermined codons can be altered by substitution, deletion or insertion. Exemplary methods of making such alterations are disclosed by Walder et al. (*Gene* 42:133, 1986); Bauer et al. (*Gene* 37:73, 1985); Craik (*BioTechniques, January* 1985, 12–19), Smith et al. (*Genetic Engineering: Principles and Methods*, Plenum Press, 1981); Kunkel (*Proc. Natl. Acad. Sci. USA* 82:488, 1985); Kunkel et al. (*Methods in Enzymol.* 154:367, 1987); and U.S. Pat. Nos. 4,518,584 and 4,737,462.

Equivalent DNA constructs that encode various additions or substitutions of amino acid residues or sequences, or deletions of terminal or internal residues or sequences not needed for biological activity are also encompassed by the invention. For example, sequences encoding Cys residues that are not essential for biological activity can be altered to cause the Cys residues to be deleted or replaced with other amino acids, preventing formation of incorrect intramolecular disulfide bridges upon renaturation. Other equivalents can be prepared by modification of adjacent dibasic amino acid residues to enhance expression in yeast systems in which KEX2 protease activity is present. EP 212,914 discloses the use of site-specific mutagenesis to inactivate KEX2 protease processing sites in a protein. KEX2 protease processing sites are inactivated by deleting, adding or substituting residues to alter Arg-Arg, Arg-Lys, and Lys-Arg pairs to eliminate the occurrence of these adjacent basic residues. Lys-Lys pairings are considerably less susceptible to KEX2 cleavage, and conversion of Arg-Lys or Lys-Arg to Lys-Lys represents a conservative and preferred approach to inactivating KEX2 sites.

Polypeptides and Fusion Proteins

The present invention further relates to ANT polypeptides, and in particular to methods for producing recombinant ANT polypeptides by culturing host cells containing ANT expression constructs, and to isolated recombinant human ANT polypeptides, including, for example, the human ANT1, ANT2 and ANT3 polypeptides which have the deduced amino acid sequence of FIG. 2 [SEQ ID NOS:31–33] or which have the amino acid sequence encoded by the deposited recombinant expression constructs, as well as fragments, analogs and derivatives of such polypeptides. The polypeptides and nucleic acids of the present invention are preferably provided in an isolated form, and in certain preferred embodiments are purified to homogeneity.

The terms "fragment," "derivative" and "analog" when referring to ANT polypeptides or fusion proteins, or to ANT polypeptides or fusion proteins encoded by the deposited recombinant expression constructs, refers to any ANT polypeptide or fusion protein that retains essentially the same biological function or activity as such polypeptide. Thus, an analog includes a proprotein which can be activated by cleavage of the proprotein portion to produce an active ANT polypeptide. The polypeptide of the present invention may be a recombinant polypeptide or a synthetic polypeptide, and is preferably a recombinant polypeptide.

A fragment, derivative or analog of an ANT polypeptide or fusion protein, including ANT polypeptides or fusion proteins encoded by the cDNAs of the deposited constructs, may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the ANT polypeptide is fused with another compound, such as a compound to increase the half-life of the polypeptide (for example, polyethylene glycol), or (iv) one in which additional amino acids are fused to the ANT polypeptide, including amino acids that are employed for purification of the ANT polypeptide or a proprotein sequence. Such fragments, derivatives and analogs are deemed to be within the scope of those skilled in the art from the teachings herein.

The polypeptides of the present invention include ANT polypeptides and fusion proteins having amino acid sequences that are identical or similar to sequences known in the art. For example by way of illustration and not limitation, the human ANT ("huANT") polypeptides of FIG. 2 [SEQ ID NOS:31–33] are contemplated for use according to the instant invention, as are polypeptides having at least 70% similarity (preferably a 70% identity) to the polypeptides of FIG. 2 [SEQ ID NOS:31–33] and more preferably 90% similarity (more preferably a 90% identity) to the polypeptides of FIG. 2 [SEQ ID NOS: 31–33] and still more preferably a 95% similarity (still more preferably a 95% identity) to the polypeptides of FIG. 2 [SEQ ID NOS:31–33] and to portions of such polypeptides, wherein such portions of an ANT polypeptide generally contain at least 30 amino acids and more preferably at least 50 amino acids.

As known in the art "similarity" between two polypeptides is determined by comparing the amino acid sequence and conserved amino acid substitutes thereto of the polypeptide to the sequence of a second polypeptide. Fragments or portions of the polypeptides of the present invention may be employed for producing the corresponding full-length polypeptide by peptide synthesis; therefore, the fragments may be employed as intermediates for producing the full-length polypeptides. Fragments or portions of the nucleic acids of the present invention may be used to synthesize full-length nucleic acids of the present invention.

The term "isolated" means that the material is removed from its original environment (e.g., the natural environment if it is naturally occurring). For example, a naturally occurring nucleic acid or polypeptide present in a living animal is not isolated, but the same nucleic acid or polypeptide, separated from some or all of the co-existing materials in the natural system, is isolated. Such nucleic acids could be part of a vector and/or such nucleic acids or polypeptides could be part of a composition, and still be isolated in that such vector or composition is not part of its natural environment.

The term "gene" means the segment of DNA involved in producing a polypeptide chain; it includes regions preceding and following the coding region "leader and trailer" as well as intervening sequences (introns) between individual coding segments (exons).

As described herein, the invention provides ANT fusion proteins encoded by nucleic acids that have the ANT coding sequence fused in frame to an additional coding sequence to provide for expression of an ANT polypeptide sequence fused to an additional functional or non-functional polypeptide sequence that permits, for example by way of illustration and not limitation, detection, isolation and/or purification of the ANT fusion protein. Such ANT fusion proteins may permit detection, isolation and/or purification of the ANT fusion protein by protein—protein affinity, metal affinity or charge affinity-based polypeptide purification, or by specific protease cleavage of a fusion protein containing a fusion sequence that is cleavable by a protease such that the ANT polypeptide is separable from the fusion protein.

Thus ANT fusion proteins may comprise polypeptide sequences added to ANT to facilitate detection and isolation of ANT. Such peptides include, for example, poly-His or the antigenic identification peptides described in U.S. Pat. No. 5,011,912 and in Hopp et al., (1988 *Bio/Technology* 6:1204), or the XPRESS™ epitope tag (Invitrogen, Carlsbad, Calif.). The affinity sequence may be a hexa-histidine tag as supplied, for example, by a pBAD/His (Invitrogen) or a pQE-9 vector to provide for purification of the mature polypeptide fused to the marker in the case of a bacterial host, or, for example, the affinity sequence may be a hemagglutinin (HA) tag when a mammalian host, e.g., COS-7 cells, is used. The HA tag corresponds to an antibody defined epitope derived from the influenza hemagglutinin protein (Wilson et al., *Cell* 37:767 (1984)).

ANT fusion proteins may further comprise immunoglobulin constant region polypeptides added to ANT to facilitate detection, isolation and/or localization of ANT. The immunoglobulin constant region polypeptide preferably is fused to the C-terminus of an ANT polypeptide. General preparation of fusion proteins comprising heterologous polypeptides fused to various portions of antibody-derived polypeptides (including the Fc domain) has been described, e.g., by Ashkenazi et al. (PNAS USA 88:10535, 1991) and Byrn et al. (Nature 344:677, 1990). A gene fusion encoding the ANT:Fc fusion protein is inserted into an appropriate expression vector. In certain embodiments of the invention, ANT:Fc fusion proteins may be allowed to assemble much like antibody molecules, whereupon interchain disulfide bonds form between Fc polypeptides, yielding dimeric ANT fusion proteins.

ANT fusion proteins having specific binding affinities for pre-selected antigens by virtue of fusion polypeptides comprising immunoglobulin V-region domains encoded by DNA sequences linked in-frame to sequences encoding ANT are also within the scope of the invention, including variants and fragments thereof as provided herein. General strategies for the construction of fusion proteins having immunoglobulin V-region fusion polypeptides are disclosed, for example, in EP 0318554, U.S. Pat. No. 5,132,405; U.S. Pat. No. 5,091,513; and U.S. Pat. No. 5,476,786.

The nucleic acid of the present invention may also encode a fusion protein comprising an ANT polypeptide fused to other polypeptides having desirable affinity properties, for example an enzyme such as glutathione-S-transferase. As another example, ANT fusion proteins may also comprise an ANT polypeptide fused to a *Staphylococcus aureus* protein A polypeptide; protein A encoding nucleic acids and their use in constructing fusion proteins having affinity for immunoglobulin constant regions are disclosed generally, for example, in U.S. Pat. No. 5,100,788. Other useful affinity polypeptides for construction of ANT fusion proteins may include streptavidin fusion proteins, as disclosed, for example, in WO 89/03422; U.S. Pat. No. 5,489,528; U.S. Pat. No. 5,672,691; WO 93/24631; U.S. Pat. No. 5,168,049, U.S. Pat. No. 5,272,254 and elsewhere, and avidin fusion proteins (see, e.g., EP 511,747). As provided herein and in the cited references, ANT polypeptide seqences may be fused to fusion polypeptide sequences that may be full length fusion polypeptides and that may alternatively be variants or fragments thereof.

The present invention also provides a method of targeting a polypeptide of interest to a membrane, and in particular embodiments to a cellular membrane, and in further embodiments to a mitochondrial membrane. This aspect of the invention is based on the unexpected observation that certain recombinant expression constructs as provided herein, which constructs include a nucleic acid encoding a first polypeptide that is an ANT polypeptide, and that is expressed as a fusion protein with a second polypeptide sequence, provide recombinant ANT fusion proteins capable of preferentially localizing to cell membranes. In certain embodiments the cell membrane is a prokaryotic cell membrane such as a bacterial cell membrane, for example an *E. coli* membrane. In other embodiments the cell membrane is a eukaryotic cell membrane such as a yeast or a mammalian cell membrane, for example a membrane of any eukaryotic cell contemplated herein.

A cell membrane as used herein may be any cellular membrane, and typically refers to membranes that are in contact with cytosolic components, including intracellular membrane bounded compartments such as mitochondrial inner and outer membranes as described above, and also intracellular vesicles, ER-Golgi constituents, other organelles and the like, as well as the plasma membrane. In preferred embodiments, an ANT fusion protein may be targeted to a mitochondrial membrane. In other preferred embodiments, for example, recombinant expression constructs according to the invention may encode ANT fusion proteins that contain polypeptide sequences that direct the fusion protein to be retained in the cytosol, to reside in the lumen of the endoplasmic reticulum (ER), to be secreted from a cell via the classical ER-Golgi secretory pathway, to be incorporated into the plasma membrane, to associate with a specific cytoplasmic component including the cytoplasmic domain of a transmembrane cell surface receptor or to be directed to a particular subcellular location by any of a variety of known intracellular protein sorting mechanisms with which those skilled in the art will be familiar. Accordingly, these and related embodiments are encompassed by the instant compositions and methods directed to targeting a polypeptide of interest to a predefined intracellular, membrane or extracellular localization.

Vectors

The present invention also relates to vectors and to constructs that include nucleic acids of the present invention, and in particular to "recombinant expression constructs" that include any nucleic acids encoding ANT polypeptides according to the invention as provided above; to host cells which are genetically engineered with vectors and/or constructs of the invention and to the production of ANT polypeptides and fusion proteins of the invention, or fragments or variants thereof, by recombinant techniques.

ANT proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., *Molecular Cloning: A Laboratory Manual*, Second Edition, Cold Spring Harbor, N.Y., (1989).

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences. Optionally, the heterologous sequence can encode a fusion protein including an N-terminal identification peptide imparting desired characteristics, e.g., stabilization or simplified purification of expressed recombinant product.

Useful expression constructs for bacterial use are constructed by inserting into an expression vector a structural DNA sequence encoding a desired protein together with suitable translation initiation and termination signals in operable reading phase with a functional promoter. The construct may comprise one or more phenotypic selectable marker and an origin of replication to ensure maintenance of the vector construct and, if desirable, to provide amplification within the host. Suitable prokaryotic hosts for transformation include *E. coli, Bacillus subtilis, Salmonella typhimurium* and various species within the genera *Pseudomonas, Streptomyces*, and *Staphylococcus*, although others may also be employed as a matter of choice. Any other plasmid or vector may be used as long as they are replicable and viable in the host.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter, if it is a regulated promoter as provided herein, is induced by appropriate means (e.g., temperature shift or chemical induction) and cells are cultured for an additional period. Cells are typically harvested by centrifugation, disrupted by physical or chemical means, and the resulting crude extract retained for further purification. Microbial cells employed in expression of proteins can be disrupted by any convenient method, including freeze-thaw cycling, sonication, mechanical disruption, or use of cell lysing agents; such methods are well know to those skilled in the art.

Thus, for example, the nucleic acids of the invention as provided herein may be included in any one of a variety of expression vector constructs as a recombinant expression construct for expressing an ANT polypeptide. Such vectors and constructs include chromosomal, nonchromosomal and synthetic DNA sequences, e.g., derivatives of SV40; bacterial plasmids; phage DNA; baculovirus; yeast plasmids, vectors derived from combinations of plasmids and phage DNA, viral DNA, such as vaccinia, adenovirus, fowl pox virus, and pseudorabies. However, any other vector may be used for preparation of a recombinant expression construct as long as it is replicable and viable in the host.

The appropriate DNA sequence(s) may be inserted into the vector by a variety of procedures. In general, the DNA sequence is inserted into an appropriate restriction endonuclease site(s) by procedures known in the art. Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described, for example, in Ausubel et al. (1993 Current Protocols in *Molecular Biology*, Greene Publ. Assoc. Inc. & John Wiley & Sons, Inc., Boston, Mass.); Sambrook et al. (1989 *Molecular Cloning*, Second Ed., Cold Spring Harbor Laboratory, Plainview, N.Y.); Maniatis et al. (1982 Molecular Cloning, Cold Spring Harbor Laboratory, Plainview, N.Y.), and elsewhere.

The DNA sequence in the expression vector is operatively linked to at least one appropriate expression control sequences (e.g., a promoter or a regulated promoter) to direct mRNA synthesis. Representative examples of such expression control sequences include LTR or SV40 promoter, the *E. coli* lac or trp, the phage lambda $P_L$ promoter and other promoters known to control expression of genes in prokaryotic or eukaryotic cells or their viruses. Promoter regions can be selected from any desired gene using CAT (chloramphenicol transferase) vectors or other vectors with selectable markers. Two appropriate vectors are pKK232-8 and pCM7. Particular named bacterial promoters include lac, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-1. Selection of the appropriate vector and promoter is well within the level of ordinary skill in the art, and preparation of certain particularly preferred recombinant expression constructs comprising at least one promoter or regulated promoter operably linked to a nucleic acid encoding an ANT polypeptide is described herein.

In certain preferred embodiments the expression control sequence is a "regulated promoter", which may be a promoter as provided herein and may also be a repressor binding site, an activator binding site or any other regulatory sequence that controls expression of a nucleic acid sequence as provided herein. In certain particularly preferred embodiments the regulated promoter is a tightly regulated promoter that is specifically inducible and that permits little or no transcription of nucleic acid sequences under its control in the absence of an induction signal, as is known to those familiar with the art and described, for example, in Guzman et al. (1995 *J. Bacteriol.* 177:4121), Carra et al. (1993 *EMBO J.* 12:35), Mayer (1995 *Gene* 163:41), Haldimann et al. (1998 *J. Bacteriol.* 180:1277), Lutz et al. (1997 *Nuc. Ac. Res.* 25:1203), Allgood et al. (1997 *Curr. Opin. Biotechnol.* 8:474) and Makrides (1996 *Microbiol. Rev.* 60:512), all of which are hereby incorporated by reference. In other preferred embodiments of the invention a regulated promoter is present that is inducible but that may not be tightly regulated. In certain other preferred embodiments a promoter is present in the recombinant expression construct of the invention that is not a regulated promoter, such a promoter may include, for example, a constitutive promoter such as an insect polyhedrin promoter as described in the Examples or a yeast phosphoglycerate kinase promoter (see, e.g., Giraud et al., 1998 *J. Mol. Biol.* 281:409). The expression construct also contains a ribosome binding site for translation initiation and a transcription terminator. The vector may also include appropriate sequences for amplifying expression.

Transcription of the DNA encoding the polypeptides of the present invention by higher eukaryotes may be increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

As noted above, in certain embodiments the vector may be a viral vector such as a retroviral vector. For example, retroviruses from which the retroviral plasmid vectors may be derived include, but are not limited to, Moloney Murine Leukemia Virus, spleen necrosis virus, retroviruses such as Rous Sarcoma Virus, Harvey Sarcoma virus, avian leukosis virus, gibbon ape leukemia virus, human immunodeficiency virus, adenovirus, Myeloproliferative Sarcoma Virus, and mammary tumor virus.

The viral vector includes one or more promoters. Suitable promoters which may be employed include, but are not limited to, the retroviral LTR; the SV40 promoter; and the human cytomegalovirus (CMV) promoter described in Miller, et al., *Biotechniques* 7:980–990 (1989), or any other promoter (e.g., cellular promoters such as eukaryotic cellular promoters including, but not limited to, the histone, pol III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein, and may be from among either regulated promoters or promoters as described above.

The retroviral plasmid vector is employed to transduce packaging cell lines to form producer cell lines. Examples of packaging cells which may be transfected include, but are not limited to, the PE501, PA317, ψ-2, ψ-AM, PA12, T19-14X, VT-19-17-H2, ψCPE, ψCRIP, GP+E-86, GP+envAm12, and DAN cell lines as described in Miller, *Human Gene Therapy*, 1:5–14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the ANT polypeptides or fusion proteins. Such retroviral vector particles then may be employed, to transduce eukaryotic cells, either in vitro or in vivo. The transduced eukaryotic cells will express the nucleic acid sequence(s) encoding the ANT polypeptide or fusion protein. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

As another example of an embodiment of the invention in which a viral vector is used to prepare the recombinant ANT expression construct, in one preferred embodiment, host cells transduced by a recombinant viral construct directing the expression of ANT polypeptides or fusion proteins may produce viral particles containing expressed ANT polypeptides or fusion proteins that are derived from portions of a host cell membrane incorporated by the viral particles during viral budding. In another preferred embodiment, ANT encoding nucleic acid sequences are cloned into a baculovirus shuttle vector, which is then recombined with a baculovirus to generate a recombinant baculovirus expression construct that is used to infect, for example, Sf9 or *Trichoplusia ni* (PharMingen, Inc., San Diego, Calif.) host cells, as described in *Baculovirus Expression Protocols, Methods in Molecular Biology* Vol. 39, Christopher D. Richardson, Editor, Human Press, Totowa, N.J., 1995; Piwnica-Worms, "Expression of Proteins in Insect Cells Using Baculoviral Vectors," Section II in Chapter 16 in: *Short Protocols in Molecular Biology*, 2 Ed., Ausubel et al., eds., John Wiley & Sons, New York, N.Y., 1992, pages 16–32 to 16–48.

Host Cells

In another aspect, the present invention relates to host cells containing the above described recombinant ANT expression constructs. Host cells are genetically engineered (transduced, transformed or transfected) with the vectors and/or expression constructs of this invention which may be, for example, a cloning vector, a shuttle vector or an expression construct. The vector or construct may be, for example, in the form of a plasmid, a viral particle, a phage, etc. The engineered host cells can be cultured in conventional nutrient media modified as appropriate for activating promoters, selecting transformants or amplifying particular genes such as genes encoding ANT polypeptides or ANT fusion proteins. The culture conditions for particular host cells selected for expression, such as temperature, pH and the like, will be readily apparent to the ordinarily skilled artisan.

The host cell can be a higher eukaryotic cell, such as a mammalian cell, or a lower eukaryotic cell, such as a yeast cell, or the host cell can be a prokaryotic cell, such as a bacterial cell. Representative examples of appropriate host cells according to the present invention include, but need not be limited to, bacterial cells, such as *E. coli, Streptomyces, Salmonella tvphimurium*; fungal cells, such as yeast; insect cells, such as *Drosophila* Sf2, *Trichoplusia ni* (PharMingen, San Diego, Calif.) and *Spodoptera* Sf9; animal cells, such as CHO, COS or 293 cells; adenoviruses; plant cells, or any suitable cell already adapted to in vitro propagation or so established de novo. The selection of an appropriate host is deemed to be within the scope of those skilled in the art from the teachings herein.

Various mammalian cell culture systems can also be employed to express recombinant protein. Examples of mammalian expression systems include the COS-7 lines of monkey kidney fibroblasts, described by Gluzman, *Cell* 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences, for example as described herein regarding the preparation of ANT expression constructs. DNA sequences derived from the SV40 splice, and polyadenylation sites may be used to provide the required nontranscribed genetic elements. Introduction of the construct into the host cell can be effected by a variety of methods with which those skilled in the art will be familiar, including but not limited to, for example, calcium phosphate transfection, DEAE-Dextran mediated transfection, or electroporation (Davis et al., 1986 *Basic Methods in Molecular Biology*).

As will be appreciated by those of ordinary skill in the art, in certain situations it may be desirable to prepare the compositions of the invention and to practice the methods of the invention under conditions where endogenous ANT expression by a host cell is compromised, in order to provide advantages associated with the expression of a desired ANT encoding construct. For example, detection of particular ANT encoding nucleic acid sequences or ANT polypeptides that are highly similar to those encoded by the host cell genome may be facilitated by inhibiting host cell ANT gene expression. As another example, where functional activity of an exogenously introduced recombinant ANT polypeptide is to be determined in a host cell or in a biological sample derived therefrom, it may also be advantageous to inhibit endogenous host cell ANT gene expression.

Thus, in certain preferred embodiments of the invention, host cells may lack at least one isoform of an endogenous ANT, and in certain preferred embodiments the host cells may lack all endogenous ANT isoforms. For example, in the yeast system described by Giraud et al. (1998 *J. Mol. Biol.* 281:409) a *S. cerevisiae* triple null mutant is described that lacks all three yeast ANT isoforms and is unable to grow under anaerobic conditions. In other preferred embodiments, expression in host cells of at least one gene encoding an endogenous ANT isoform is substantially impaired. Substantial impairment of endogenous ANT isoform expression may be achieved by any of a variety of methods that are well known in the art for blocking specific gene expression, including site-specific or site-directed mutagenesis as described above, antisense inhibition of gene expression, ribozyme mediated inhibition of gene expression and generation of mitochondrial DNA depleted ($p^0$) cells.

Identification of oligonucleotides and ribozymes for use as antisense agents and DNA encoding genes for targeted delivery for genetic therapy involve methods well known in the art. For example, the desirable properties, lengths and other characteristics of such oligonucleotides are well known. Antisense oligonucleotides are typically designed to resist degradation by endogenous nucleolytic enzymes by using such linkages as: phosphorothioate, methylphosphonate, sulfone, sulfate, ketyl, phosphorodithioate, phosphoramidate, phosphate esters, and other such linkages (see, e.g., Agrwal et al., *Tetrehedron Lett.* 28:3539–3542 (1987); Miller et al., *J. Am. Chem. Soc.* 93:6657–6665 (1971); Stec et al., *Tetrehedron Lett.* 26:2191–2194 (1985); Moody et al., *Nucl. Acids Res.* 12:4769–4782 (1989); Uznanski et al., *Nucl. Acids Res.* (1989); Letsinger et al., *Tetrahedron* 40:137–143 (1984); Eckstein, *Annu. Rev. Biochem.* 54:367–402 (1985); Eckstein, *Trends Biol. Sci.* 14:97–100 (1989); Stein In: *Oligodeoxynucleotides. Antisense Inhibitors of Gene Expression*, Cohen, Ed, Macmillan Press, London, pp. 97–117 (1989); Jager et al., *Biochemistry* 27:7237–7246 (1988)).

Antisense nucleotides are oligonucleotides that bind in a sequence-specific manner to nucleic acids, such as mRNA or DNA. When bound to mRNA that has complementary sequences, antisense prevents translation of the mRNA (see, e.g., U.S. Pat. No. 5,168,053 to Altman et al., U.S. Pat. No. 5,190,931 to Inouye, U.S. Pat. No. 5,135,917 to Burch; U.S. Pat. No. 5,087,617 to Smith and Clusel et al. (1993) *Nucl. Acids Res.* 21:3405–3411, which describes dumbbell antisense oligonucleotides). Triplex molecules refer to single DNA strands that bind duplex DNA forming a colinear triplex molecule, thereby preventing transcription (see, e.g., U.S. Pat. No. 5,176,996 to Hogan et al., which describes methods for making synthetic oligonucleotides that bind to target sites on duplex DNA).

According to this embodiment of the invention, particularly useful antisense nucleotides and triplex molecules are molecules that are complementary to or bind the sense strand of DNA or mRNA that encodes an ANT polypeptide or a protein mediating any other process related to expression of endogenous ANT genes, such that inhibition of translation of mRNA encoding the ANT polypeptide is effected.

A ribozyme is an RNA molecule that specifically cleaves RNA substrates, such as mRNA, resulting in specific inhibition or interference with cellular gene expression. There are at least five known classes of ribozymes involved in the cleavage and/or ligation of RNA chains. Ribozymes can be targeted to any RNA transcript and can catalytically cleave such transcripts (see, e.g., U.S. Pat. No. 5,272,262; U.S. Pat. No. 5,144,019; and U.S. Pat. Nos. 5,168,053, 5,180,818, 5,116,742 and 5,093,246 to Cech et al.). According to certain embodiments of the invention, any such ANT mRNA-specific ribozyme, or a nucleic acid encoding such a ribozyme, may be delivered to a host cell to effect inhibition of ANT gene expression. Ribozymes, and the like may therefore be delivered to the host cells by DNA encoding the ribozyme linked to a eukaryotic promoter, such as a eukaryotic viral promoter, such that upon introduction into the nucleus, the ribozyme will be directly transcribed.

As used herein, expression of a gene encoding an endogenous adenine nucleotide translocator isoform is substantially impaired by any of the above methods for inhibiting when cells are substantially but not necessarily completely depleted of functional DNA or functional mRNA encoding the endogenous ANT isoform, or of the relevant ANT polypeptide. ANT isoform expression is substantially impaired when cells are preferably at least 50% depleted of DNA or mRNA encoding the endogenous ANT (as measured using high stringency hybridization as described above) or depleted of ANT polypeptide (as measured by Western immunoblot as described herein, see also, e.g., Giraud et al. 1998-J. Mol. Biol. 281:409); and more preferably at least 75% depleted of endogenous ANT DNA, mRNA or polypeptide. Most preferably, ANT isoform expression is substantially impaired when cells are depleted of >90% of their endogenous ANT DNA, mRNA, or polypeptide.

Alternatively, expression of a gene encoding an endogenous adenine nucleotide translocator isoform may be substantially impaired through the use of mitochondrial DNA depleted $p^0$ cells, which are incapable of mitochondrial replication and so may not continue to express functional ANT polypeptides. Methods for producing $p^0$ cells are known and can be found, for example in PCT/US95/04063, which is hereby incorporated by reference.

Protein Production

The expressed recombinant ANT polypeptides or fusion proteins may be useful in intact host cells; in intact organelles such as mitochondria, cell membranes, intracellular vesicles other cellular organelles; or in disrupted cell preparations including but not limited to cell homogenates or lysates, submitochondrial particles, uni- and multilamellar membrane vesicles or other preparations. Alternatively, expressed recombinant ANT polypeptides or fusion proteins can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

Samples

A "biological sample containing mitochondria" may comprise any tissue or cell preparation in which intact mitochondria capable of maintaining a membrane potential when supplied with one or more oxidizable substrates such as glucose, malate or galactose are or are thought to be present. Mitochondrial membrane potential may be determined according to methods with which those skilled in the art will be readily familiar, including but not limited to detection and/or measurement of detectable compounds such as fluorescent indicators, optical probes and/or sensitive pH and ion-selective electrodes (See, e.g., Ernster et al., 1981 *J. Cell Biol.* 91:227s and references cited therein, see also Haugland, 1996 *Handbook of Fluorescent Probes and Research Chemicals*—Sixth Ed., Molecular Probes, Eugene, Oreg., pp. 266–274 and 589–594.). By "capable of maintaining a potential" it is meant that such mitochondria have a membrane potential that is sufficient to permit the accumulation of a detectable compound (e.g., DASPMI [2-,4-dimethylaminostyryl-N-methylpyridinium], TMRM [tetramethylrhodamine methyl ester], etc.) used in the particular instance. A biological sample containing mitochondria may, for example, be derived from a normal (i.e., healthy) individual or from an individual having a disease associated with altered mitochondrial function. Biological samples containing mitochondria may be provided by obtaining a blood sample, biopsy specimen, tissue explant, organ culture or any other tissue or cell preparation from a subject or a biological source. The subject or biological source may be a human or non-human animal, a primary cell culture or culture adapted cell line including but not limited to genetically engineered cell lines that may contain chromosomally integrated or episomal recombinant nucleic acid sequences, immortalized or immortalizable cell lines, somatic cell hybrid or cytoplasmic hybrid "cybrid" cell lines, differentiated or differentiatable cell lines, transformed cell lines and the like.

A "biological sample" may comprise any tissue or cell preparation as just described for a biological sample containing mitochondria, but does not require the presence of intact mitochondria. Thus a "biological sample" may comprise any tissue or cell preparation and a "biological sample" containing at least "one recombinant ANT polypeptide" comprises any tissue or cell preparation in which an expressed recombinant ANT polypeptide or fusion protein as provided herein is thought to be present. A biological sample may, for example, be derived from a recombinant cell line or from a transgenic animal. Biological samples containing recombinant ANT may be provided by obtaining a blood sample, biopsy specimen, tissue explant, organ culture or any other tissue or cell preparation from a subject or a biological source. The subject or biological source may be a human or non-human animal, a primary cell culture or culture adapted cell line including but not limited to genetically engineered cell lines that may contain chromosomally integrated or episomal recombinant nucleic acid sequences, immortalized or immortalizable cell lines, somatic cell hybrid or cytoplasmic hybrid "cybrid" cell lines, differentiated or differentiatable cell lines, transformed cell lines and the like.

Proteins

As described herein, isolation of a mitochondrial pore component or a mitochondrial molecular species with which an agent identified according to the methods of the invention interacts refers to physical separation of such a complex from its biological source, and may be accomplished by any of a number of well known techniques including but not limited to those described herein, and in the cited references. Without wishing to be bound by theory, a compound that "binds a mitochondrial component" can be any discrete molecule, agent compound, composition of matter or the like that may, but need not, directly bind to a mitochondrial molecular component, and may in the alternative bind indirectly to a mitochondrial molecular component by interacting with one or more additional components that bind to a mitochondrial molecular component. These or other mechanisms by which a compound may bind to and/or associate with a mitochondrial molecular component are within the scope of the claimed methods, so long as isolating a mitochondrial pore component also results in isolation of the mitochondrial molecular species that directly or indirectly binds to the identified agent. Thus, for example, as provided herein, any ANT polypeptide including recombinant ANT polypeptides and fusion proteins may be a mitochondrial molecular component and/or a mitochondrial pore component, and any ANT ligand or agent that binds to an ANT polypeptide may be a compound that binds a mitochondrial component and/or an agent that affects mitochondrial pore activity.

As described herein, the mitochondrial permeability transition "pore" may not be a discrete assembly or multisubunit complex, and the term thus refers instead to any mitochondrial molecular component (including, e.g., a mitochondrial membrane per se) that regulates the inner membrane selective permeability where such regulated function is impaired during MPT. As used herein, mitochondria are comprised of "mitochondrial molecular components", which may be any protein, polypeptide, peptide, amino acid, or derivative thereof; any lipid, fatty acid or the like, or derivative thereof; any carbohydrate, saccharide or the like or derivative thereof, any nucleic acid, nucleotide, nucleoside, purine, pyrimidine or related molecule, or derivative thereof, or the like; or any other biological molecule that is a constituent of a mitochondrion. "Mitochondrial molecular components" includes but is not limited to "mitochondrial pore components". A "mitochondrial pore component" is any mitochondrial molecular component that regulates the selective permeability characteristic of mitochondrial membranes as described above, including those responsible for establishing $\Delta\psi m$ and those that are functionally altered during MPT.

Isolation and, optionally, identification and/or characterization of the mitochondrial pore component or components with which an agent that affects mitochondrial pore activity interacts may also be desirable and are within the scope of the invention. Once an agent is shown to alter MPT according to the methods provided herein and in U.S. Ser. No.

09/161,172, those having ordinary skill in the art will be familiar with a variety of approaches that may be routinely employed to isolate the molecular species specifically recognized by such an agent and involved in regulation of MPT, where to "isolate" as used herein refers to separation of such molecular species from the natural biological environment. Thus, for example, once an ANT ligand is prepared according to the methods provided herein, such approaches may be routinely employed to isolate the ANT polypeptide. Techniques for isolating a mitochondrial pore component such as an ANT polypeptide or fusion protein may include any biological and/or biochemical methods useful for separating the complex from its biological source, and subsequent characterization may be performed according to standard biochemical and molecular biology procedures. Those familiar with the art will be able to select an appropriate method depending on the biological starting material and other factors. Such methods may include, but need not be limited to, radiolabeling or otherwise detectably labeling cellular and mitochondrial components in a biological sample, cell fractionation, density sedimentation, differential extraction, salt precipitation, ultrafiltration, gel filtration, ion-exchange chromatography, partition chromatography, hydrophobic chromatography, electrophoresis, affinity techniques or any other suitable separation method that can be adapted for use with the agent with which the mitochondrial pore component interacts. Antibodies to partially purified components may be developed according to methods known in the art and may be used to detect and/or to isolate such components.

Affinity techniques may be particularly useful in the context of the present invention, and may include any method that exploits a specific binding interaction between a mitochondrial pore component and an agent identified according to the invention that interacts with the pore component. For example, because ANT ligands as provided herein and other agents that influence MPT can be immobilized on solid phase matrices, an affinity binding technique for isolation of the pore component may be particularly useful. Alternatively, affinity labeling methods for biological molecules, in which a known MPT-active agent or a novel ANT ligand as provided herein may be modified with a reactive moiety, are well known and can be readily adapted to the interaction between the agent and a pore component, for purposes of introducing into the pore component a detectable and/or recoverable labeling moiety. (See, e.g., Pierce Catalog and Handbook, 1994 Pierce Chemical Company, Rockford, LL; Scopes, R. K., Protein Purification: Principles and Practice, 1987, Springer-Verlag, New York; and Hermanson, G. T. et al., Immobilized Affinity Ligand Techniques, 1992, Academic Press, Inc., California; for details regarding techniques for isolating and characterizing biological molecules, including affinity techniques.

Characterization of mitochondrial pore component molecular species, isolated by MPT-active agent affinity techniques described above or by other biochemical methods, may be accomplished using physicochemical properties of the pore component such as spectrometric absorbance, molecular size and/or charge, solubility, peptide mapping, sequence analysis and the like. (See, e.g., Scopes, supra.) Additional separation steps for biomolecules may be optionally employed to further separate and identify molecular species that co-purify with mitochondrial pore components. These are well known in the art and may include any separation methodology for the isolation of proteins, lipids, nucleic acids or carbohydrates, typically based on physicochemical properties of the newly identified components of the complex. Examples of such methods include RP-HPLC, ion exchange chromatography, hydrophobic interaction chromatography, hydroxyapatite chromatography, native and/or denaturing one- and two-dimensional electrophoresis, ultrafiltration, capillary electrophoresis, substrate affinity chromatography, immunoaffinity chromatography, partition chromatography or any other useful separation method. Preferably extracts of cultured cells, and in particularly preferred embodiments extracts of biological tissues or organs may be sources of mitochondrial molecular components, including ANT polypeptides. Preferred sources may include blood, brain, fibroblasts, myoblasts, liver cells or other cell types.

ANT Ligands

As noted above, the binding of the adenine nucleotide translocator (ANT) is responsible for mediating transport of ADP and ATP across the mitochondrial inner membrane. ANT has also been implicated as the critical component of the mitochondrial permeability transition pore, a $Ca^{2+}$ regulated inner membrane channel that plays an important modulating role in apoptotic processes. Additionally, ANT activity appears to be related to changes in ANT polypeptide conformation within the mitochondrial membrane, as evidenced by studies using agents that are capable of binding to ANT. (Block et al., 1986 Meths. Enzymol 125:658). Accordingly, it is another aspect of the present invention to provide compositions and methods for producing and identifying agents that bind to ANT, which agents are also referred to herein as ANT ligands.

Binding interactions between ANT and a variety of small molecules are known to those familiar with the art. For example, these interactions include binding to ANT by atractyloside, carboxyatractyloside, palmitoyl-CoA, bongkrekic acid, thyroxin, eosin Y and erythrosin B. (See, e.g., Stubbs, 1979 Pharm. Ther. 7:329; Klingenberg et al., 1978 Biochim. Biophys. Acta 503:193; Sterling, 1986 Endocrinol. 119:292; Majima et al., 1998 Biochem. 37:424; Block et al. 1986 Meths. Enzymol. 125:658; for erythrosin B and additional ANT inhibitors, see Beavis et al. 1993 J. Biol. Chem. 268:997; Powers et al. 1994 J. Biol. Chem. 269:10614.)

The ANT ligands of the present invention represent novel atractyloside derivatives. Atractyloside (ATR) and its known derivatives, including carboxyatractyloside (CATR), naphthoyl-ATR, MANT-ATR and other ATR derivatives (see, e.g., Boulay et al., Analytical Biochemistry 128:323–330,1983; Roux et al., Analytical Biochemistry 234:31–37,1996, Lauquin et al., FEBS Letters 67:306–311, 1976; and Gottikh et al., Tetrahedron 26:4419–4433, 1970; for other known ATR derivatives see, e.g., Block et al., 1986 Meths. Enzymol. 125:658) have proven invaluable in the elucidation of the structure and the mechanism of action of the adenine nucleotide translocator. According to the ANT ligands of the invention, the binding mode of ATR to ANT allows for modifications of the ATR 6'-hydroxyl functionality without significantly altering ATR binding affinity for ANT. Thus, ANT ligands as provided herein may be ATR derivatives modified by chemical substitution at the 6' hydroxyl position. In particular, the novel ANT ligands as provided herein further include long linker moieties at the 6' position, which linkers may include a 6'-amine linker, thereby permitting additional chemical modification to the ANT ligand as will be appreciated by those skilled in the art and as illustrated in the non-limiting Examples. Also, as shown in Examples 6–11, such linkers as provided herein may have carbon chain backbones of 2–20 carbon atoms, and in preferred embodiments 2–6 carbon atoms.

The invention therefore provides ANT ligands that may be intermediates for conjugation to a variety of additional chemical moieties to yield further ATR derivatives that are ANT ligands within the scope of the invention. These include ANT ligands to which $^{125}$I may be covalently attached under mild reaction conditions; the invention also includes ANT ligands to which reactive amine groups may be covalently linked. ANT ligands which are such amine-containing ATR derivatives may then be reacted with a variety of fluorophores and haptens bearing, for example, reactive isothiocyanate, N-hydroxysuccinimide ester, anhydride and other useful functionalities to yield stable ATR derivatives including, for example, derivatives that have thiourea, amide or other linkages.

Thus, ANT ligands as provided herein also include ATR derivatives that are detectable by virtue of substituents introduced at the 6' position. Accordingly, detectable ATR derivatives as herein provided include ATR derivatives having a 6' hydroxyl substitution that includes a radiolabeled substituent, for example $^{125}$I, $^{131}$I, $^{3}$H, $^{14}$C or $^{35}$S. Other ANT ligands that are detectable ATR derivatives may comprise fluorescent substituents, including those appropriately tagged with reporter molecules such as fluorophores and haptens having utility in high throughput screening assays for identifying agents that bind to ANT. More specifically, in preferred embodiments, an ANT ligand according to the present invention that includes fluorescent substituents has an extinction coefficient $\geq 10,000$ $M^{-1}$ (see Table 1); further, this property provides an advantage for using such ANT ligands according to the methods provided herein, and in particular for use in high throughput screening assays. Additionally, the ANT ligands of the invention exhibit high affinities for ANT, and in preferred embodiments have binding constants in the nanomolar range.

In certain embodiments of the invention, ANT ligands may be ATR derivatives such as ATR-lanthanide chelating agents, which have utility in time-resolved fluorescence detection, for example detection of these compounds complexed to a lanthanide ion such as $Eu^{3+}$, $Tb^{3+}$, $Sm^{3+}$ and $Dy^{3+}$. In addition, ANT ligands may comprise ATR conjugated to readily detectable substituents such as highly fluorescent moieties, for example by way of illustration and not limitation, cyanine and coumarin derivatives. These and other highly fluorescent substituents permit the synthesis, according to the methods of the invention, of ANT ligands that are detectable with extremely high sensitivities. Those familiar with the art are aware of additional fluorescent substituents that may be used, for example, those disclosed in Haugland, 1996 *Handbook of Fluorescent Probes and Research Chemicals*—Sixth Ed., Molecular Probes, Eugene, Oreg. In other embodiments, the invention provides detectable ANT ligands produced by coupling of biotin-NHS ester with the ATR derivatives as disclosed herein; these and other ANT ligands similarly generated according to the instant methods can be detected with commercially available enzyme-avidin conjugates using, for example, colorimetric, fluorescent or chemiluminescent techniques.

In one embodiment, the ANT ligands of this invention have the following structure (I):

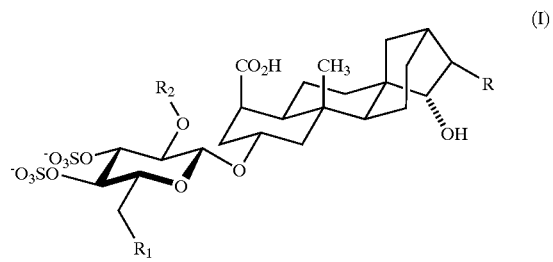

including stereoisomers and pharmaceutically acceptable salts thereof, wherein
 $R_1$ is hydroxyl, halogen, —OC(=O)$R_4$ or —NH$R_4$,
 $R_2$ is hydrogen or —C(=O)$R_5$,
 $R_3$ is —CH$_3$ or =CH$_2$;
 $R_4$ is —X-aryl, —X-substituted aryl, —X-arylalkyl, —X-substituted arylalkyl, X-heteroaryl, or —X-heteroarylalkyl, wherein X is an optional amido or alkylamido linker moiety, and
 $R_5$ is alkyl,
 As used herein, the above terms have the meanings set forth below.
 "Amido" means —NHC(=O)— or —C(=O)NH—.
 "Alkylamido" means -(alkyl)-NHC(=O)— or -(alkyl)-C(=O)NH—, such as —CH$_2$NHC(=O)—, —CH$_2$CH$_2$NHC(=O)—, —CH$_2$C(=O)NH—, —CH$_2$CH$_2$C(=O)NH—, and the like.
 "Alkyl" means a straight chain or branched, noncyclic or cyclic, unsaturated or saturated aliphatic hydrocarbon containing from 1 to 8 carbon atoms. Representative saturated straight chain alkyls include methyl, ethyl, n-propyl, n-butyl, n-pentyl, n-hexyl, and the like, while saturated branched alkyls include isopropyl, sec-butyl, isobutyl, tert-butyl, isopentyl, and the like. Representative saturated cyclic alkyls include cyclopropyl, cyclobutyl, cyclopentyl, cyclohexyl, and the like; while unsaturated cyclic alkyls include cyclopentenyl and cyclohexenyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1 butynyl, and the like.
 "Aryl" means an aromatic carbocyclic moiety such as phenyl or naphthyl (i.e., 1— or 2-naphthyl).
 "Arylalkyl" means an alkyl having at least one alkyl hydrogen atoms replaced with an aryl moiety, such as benzyl, —(CH$_2$)$_2$phenyl, —(CH$_2$)$_3$phenyl, and the like.
 "Heteroaryl" means an aromatic heterocycle ring of 5- to 10 members and having at least one heteroatom selected from nitrogen, oxygen and sulfur, and containing at least 1 carbon atom, including both mono- and bicyclic ring systems. Representative heteroaryls are pyridyl, furyl, benzofuranyl, thiophenyl, benzothiophenyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl, and quinazolinyl.
 "Heteroarylalkyl" means an alkyl having at least one alkyl hydrogen atom replaced with a heteroaryl moiety, such as —CH$_2$pyridinyl, —CH$_2$pyrimidinyl, and the like.

"Heterocycle" means a 5- to 7-membered monocyclic, or 7- to 10-membered bicyclic, heterocyclic ring which is either saturated, unsaturated, or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring. The heterocycle may be attached via any heteroatom or carbon atom. Heterocycles include heteroaryls as defined above. Thus, in addition to the heteroaryls listed above, heterocycles also include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

"Heterocyclealkyl" means an alkyl having at least one alkyl hydrogen atom replaced with a heterocycle, such as —CH$_2$morpholinyl, and the like.

The term "substituted" as used herein means any of the above groups (i.e., alkyl, aryl, arylalkyl, heteroaryl, heteroarylalkyl, heterocycle and heterocyclealkyl) wherein at least one hydrogen atom is replaced with a substituent. In the case of a keto substituent ("C(=O)") two hydrogen atoms are replaced. Substituents include halogen, hydroxy, alkyl, haloalkyl, aryl, substituted aryl, arylalkyl, substituted arylalkyl, heterocycle, substitued heterocycle, heterocyclealkyl or substituted heterocyclealkyl.

"Halogen" means fluoro, chloro, bromo and iodo.

"Haloalkyl" means an alkyl having at least one hydrogen atom replaced with halogen, such as trifluoromethyl and the like.

"Alkoxy" means an alkyl moiety attached through an oxygen bridge (i.e., —O-alkyl) such as methoxy, ethoxy, and the like.

In one embodiment, R$_2$ is —C(=O)CH$_2$CH(CH$_3$)$_2$, R$_3$ is =CH$_2$, and the ANT ligand is an atractyloside derivative having the following structure (II):

(II)

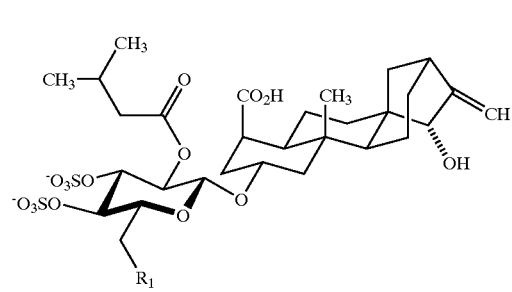

wherein R$_1$ is as defined above.

In another embodiment, R$_2$ is —C(=O)CH$_2$CH(CH$_3$)$_2$, R$_3$ is —CH$_3$, and the ANT ligand is a dihydro-atractyloside derivative having the following structure (III):

(III)

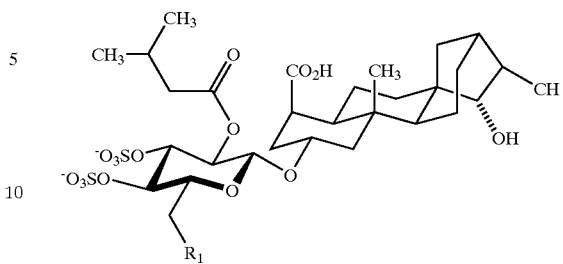

wherein R$_1$ is as defined above.

In still a further embodiment, R$_2$ is —OH, R$_3$ is =CH$_2$, and the ANT ligand is an apoatractyloside derivative having the following structure (IV):

(IV)

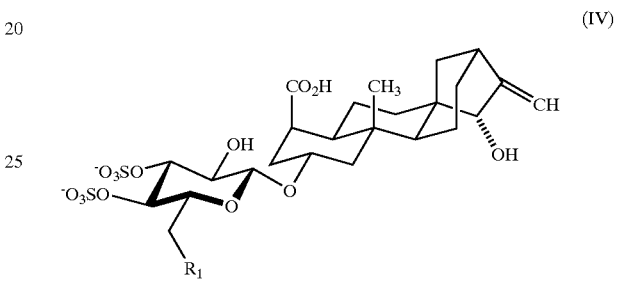

wherein R$_1$ is as defined above.

In more specific embodiments of structures (II), (III) and (IV), R$_1$ is —OC(=O)(aryl), —OC(=O)(substituted aryl), —OC(=O)(arylalkyl), —OC(=O)(substituted arylalkyl), —NH(CH$_2$)$_2$NHC(=O)(arylalkyl), —NH(CH$_2$)$_2$NHC(=O)substituted arylalkyl). Representative R$_1$ moieties in this regard include —OC(=O)(phenyl), —OC(=O)(1-naphthyl), —OC(=O)(substituted phenyl), —OC(=O)(substituted 1-naphthyl), —OC(=O)(CH$_2$)$_{1-3}$(phenyl), —OC(=O)(CH$_2$)$_{13}$(substituted phenyl), —NH(CH$_2$)$_2$NHC(=O)(CH$_2$)$_{1-3}$(phenyl), —NH(CH$_2$)$_2$NHC(=O)(CH$_2$)$_{1-3}$(substituted phenyl). In this context, representative substituted phenyl moieties include (but are not limited to) 4-hydroxyphenyl, 3-iodo-4-hydroxyphenyl, 3,5-iodo-4-hydroxyphenyl, 4-(4-hydoxyphenyl)phenyl, 4-(3-iodo-4-hyroxyphenyl)phenyl, 3-methyl-4-hyroxyphenyl, and 3-methyl-4-hydroxy-5-iodophenyl.

The ANT ligands of structure (I) may readily be made by one skilled in the art of organic chemisty and, more particularly, by the techniques disclosed in Examples 6–11.

The compounds of the present invention may generally be utilized as the free base. Alternatively, the compounds of this invention may be used in the form of acid addition salts. Acid addition salts of the free amino compounds of the present invention may be prepared by methods well known in the art, and may be formed from organic and inorganic acids. Suitable organic acids include maleic, fumaric, benzoic, ascorbic, succinic, methanesulfonic, acetic, oxalic, propionic, tartaric, salicylic, citric, gluconic, lactic, mandelic, cinnamic, aspartic, stearic, palmitic, glycolic, glutamic, and benzenesulfonic acids. Suitable inorganic acids include hydrochloric, hydrobromic, sulfuric, phosphoric, and nitric acids. Thus, the term "pharmaceutically acceptable salt" of structure (I) is intended to encompass any and all acceptable salt forms.

With regard to stereoisomers, the compounds of structure (I) may have chiral centers and may occur as recemates, reacemic mixtures and as individual enantiomers or diastereomers. All such isomeric forms are included within the present invention, including mixtures thereof. Furthermore, some of the crystalline forms of the compounds of structure (I) may exist as polymorphs, which are included in the present invention. In addition; some of the compounds of structure (I) may also form solvates with water or other organic solvents. Such solvates are similarly included within the scope of this invention.

Activities of ANT ligands are typically calculated from the $IC_{50}$ as the concentration of a compound necessary to displace 50% of the detectable (i.e., detectably labeled, for example, radiolabeled) ligand from ANT molecules, which may be present as isolated or purified polypeptides or as components of preparations containing isolated mitochondria or submitochondrial particles (SMP) using established ligand binding assays or modifications thereof. For example, ANT ligands may be tested for their ability to compete with radiolabeled ATR, or with a radiolabeled ATR derivative such as compound 24 as provided herein, for binding to isolated ANT polypeptides or to ANT present in isolated mitochondria or SMP.

As another example, the relative affinities for ANT of various ANT ligands as provided herein may be determined by a fluorescence assay that exploits the flourescent properties of compound 22 (Example 11), a naphthoyl-ATR derivative that is an ANT ligand having a fuorescence excitation peak at 312 nm and an emission peak at 400 nm. When compound 22 is bound to ANT, the fluorescence is quenched. When, however, compound 22 is displaced from ANT by a known concentration of ATR or an ATR derivative that is an ANT ligand, fluorescence dequenching that results from displacement of the fluorophore can be measured in real time.

Briefly, a mitochondrial preparation (see, e.g., Example 13) is washed and resuspended in a suitable buffer in the presence of compound 22 (e.g., 10 mM Tris-120 mM KCl containing 3.6 nmoles of compound 22 per mg mitochondrial protein, 10 min at room temperature), washed to remove unbound fluorophore and placed in a fluorometer equipped with a light source and filter set appropriate for the fluorophore. Fluorescence intensity is monitored as a function of time, and a candidate ANT ligand is then added to determine its ability to compete with compound 22 for binding to ANT, as evidenced by a change in detectable relative fluorescence intensity units. After the fluorescence signal has stabilized, any additional compound 22 that remains bound to ANT is displaced by adding an excess (e.g., $\mu$M quantities) of ATR as a competitive inhibitor, to determine maximal signal intensity and therefrom calculate the proportion of compound 22 displaced by the candidate ANT ligand. Those having familiarity with the art will appreciate that variations and modifications may be made to ANT-binding assays such as those illustrated above and described in the Examples for determing $IC_{50}$ values of candidate ANT ligands, and which are not intended to be limiting.

Activity of each ANT ligand is reported as a "$K_i$" value calculated by the following equation:

$$K_i = \frac{IC_{50}}{1 + L/K_D}$$

where L=radioligand and $K_D$=affinity of radioligand for receptor (Cheng and Prusoff, Biochem. Pharmacol. 22:3099, 1973). ANT ligands of this invention have a $K_i$ of 100 $\mu$M or less. In a preferred embodiment of this invention, the ANT ligands have a $K_i$ of less than 10 $\mu$M, and more preferably less than 1 $\mu$M. To this end, ANT ligands of this invention having a $K_i$ of less than 100 $\mu$M include compound 5 (Example 7), compound 6 (Example 8), and compounds 22, 23, 24, 26, 29, 33, 35, 37, and 38 (Example 11). Preferred ANT ligands having a $K_i$ of less than 10 $\mu$M include compounds 6, 22, 23, 24, 29, 33, 35, and 38 and more preferred ANT ligands having a $K_i$ of less than 1 $\mu$M include compounds 6, 24, 33, and 38, as well as ATR.

Assays

It is another aspect of the invention to provide compositions and methods for the determination of the presence of ANT polypeptides and for the identification of agents that bind to, or that interact with, ANT polypeptides. Such compositions and methods will be useful for diagnostic and prognostic purposes, for example in the determination of the existence of altered mitochondrial function which, as described above, may accompany both normal and disease states. These compositions and methods will also be useful for the identification of agents that alter or regulate mitochondrial function based on ANT roles in mitochondrial activities, for example by way of illustration and not limitation, maintenance of mitochondrial membrane potential, ATP biosynthesis, induction of apoptosis, MPT and other mitochondrial function. In certain preferred embodiments these compositions and methods are useful as high throughput screening assays.

In certain aspects the invention provides a method for determining the presence of an ANT polypeptide in a biological sample, comprising contacting a sample suspected of containing an ANT polypeptide with an ANT ligand under conditions and for a time sufficieint to allow binding of the ANT ligand to an ANT polypeptide, and detecting such binding. "ANT ligands" according to these aspects of the invention may include any novel ANT ligands as provided herein. The use of human ANT1, ANT2 and ANT3 according to these methods represent particularly preferred embodiments. Other preferred embodiments include the use of any ANT polypeptide or ANT fusion protein as provided herein. Accordingly, the instant method for determining the presence of ANT polypeptide in a sample will be useful for monitoring expression of ANT encoding constructs provided herein. In some preferred embodiments an ANT fusion protein is used that is a GST fusion protein, and in other preferred embodiments the ANT fusion protein is a His-tagged fusion protein. As provided herein, the biological sample may be a cell, a mitochondrion, submitochondrial particles, a cell membrane (including any cellular membrane as described herein), a cell extract, cell conditioned medium, a tissue homogenate or an isolated ANT.

In other aspects, the invention provides a method for identifying an agent that binds to an ANT polypeptide, comprising contacting a candidate agent with a host cell expressing at least one recombinant ANT polypeptide under conditions and for a time sufficient to permit binding of the agent to the ANT polypeptide and detecting such binding. In various preferred embodiments the host cell may be a prokaryotic cell or a eukaryotic cell. In certain other preferred embodiments the host cell may lack at least one isoform of an endogenous ANT, for example, due to a mutation in one or more endogenous ANT encoding genes. In certain other embodiments host cell expression of at least one gene encoding an endogenous ANT isoform is substantially impaired, for example, through the use of ANT nucleic acid-specific ribozyme or antisense constructs as provided herein, or through the use of $p^0$ cells, as also provided herein.

According to other embodiments of this aspect of the invention, it may be preferred to use intact cells or, alternatively, to use permeabilized cells. Those having ordinary skill in the art are familiar with methods for permeabilizing cells, for example by way of illustration and not limitation, through the use of surfactants, detergents, phospholipids, phospholipid binding proteins, enzymes, viral membrane fusion proteins and the like; through the use of osmotically active agents; by using chemical crosslinking agents; by physicochemical methods including electroporation and the like, or by other permeabilizing methodologies.

In other aspects, the invention provides a method for identifying an agent that binds to an ANT polypeptide comprising contacting a candidate agent with a biological sample containing at least one recombinant ANT polypeptide under conditions and for a time sufficient to permit binding of the agent to the ANT polypeptide, and detecting such binding. The use of human ANT1, ANT2 and ANT3 according to these methods represent particularly preferred embodiments. Other preferred embodiments include the use of any ANT polypeptide or ANT fusion protein as provided herein. In some preferred embodiments an ANT fusion protein is used that is a GST fusion protein, and in other preferred embodiments the ANT fusion protein is a His-tagged fusion protein. As provided herein, the biological sample may be a cell, a mitochondrion, submitochondrial particles, a cell membrane (including any cellular membrane as described herein), a cell extract, cell conditioned medium, a recombinant viral particle, a tissue homogenate or an isolated ANT. Detection of binding may be by any of a variety of methods and will depend on the nature of the candidate agent being screened. For example, certain candidate agents are inherently detectable as a consequence of their physicochemical properties, such as will be apparent to those skilled in the art and including spectrophotometric, colorimetric, fluorimetric, solubility, hydrophobic, hydrophilic, electrostatic charge, molecular mass or other physicochemical properties. As another example, certain candidate agents may be radioactively labeled with a readily detectable radionuclide, as is well known in the art. Certain candidate agents may also be directly or indirectly detectable by ANT protein affinity methodologies, for example by their ability to interfere with binding of an ANT-specific antibody to an ANT; or by their being removable from an assay solution using a protein affinity reagent that binds to a fusion polypeptide present as a portion of an ANT fusion protein. A candidate agent bound to an ANT polypeptide may be detected by any method known for the detection, identification or characterization of relevant molecules, including spectrophotometric, mass spectrometric, chromatographic, electrophoretic, calorimetric or any other suitable analytical technique.

In another aspect the invention provides a method for identifying an agent that interacts with an ANT polypeptide comprising contacting a biological sample containing recombinant ANT with a detectable ANT ligand (or a known detectable molecule capable of binding to ANT) in the presence of a candidate agent, and comparing binding of the detectable ANT ligand (or known detectable ANT binding molecule) to recombinant ANT in the absence of the agent to binding of the detectable ANT ligand (or known detectable ANT binding molecule) to recombinant ANT in the presence of the agent, and therefrom identifying an agent that interacts with an ANT polypeptide. It will be appreciated that in certain preferred embodiments this aspect provides competitive binding assays wherein novel ANT ligands as provided hereinabove are useful. However, this aspect of the invention need not be so limited and may be modified to employ known detectable ANT binding molecules, in which case it should be pointed out that the selection of biological sample and/or of recombinant ANT as provided by the present invention offer unexpected advantages heretofore unknown in the art. Examples of known detectable ANT-binding molecules include suitably labeled ATP, ADP, ATR, CATR, palmitoyl-CoA, bongkrekic acid, thyroxin, eosin Y and erythrosin B or other ANT-binding molecules known in the art. (See, e.g., Block et al., 1986 *Meths. Enzymol.* 125.658.) The use of human ANT1, ANT2 and ANT3 according to these methods represent particularly preferred embodiments. Other preferred embodiments include the use of any ANT polypeptide or ANT fusion protein as provided herein. In some preferred embodiments an ANT fusion protein is used that is a GST fusion protein, and in other preferred embodiments the ANT fusion protein is a His-tagged fusion protein. As provided herein, the biological sample may be a cell, a mitochondrion, submitochondrial particles, a cell membrane (including any cellular membrane as described herein), a cell extract, cell conditioned medium, a recombinant viral particle, a tissue homogenate or an isolated ANT.

The ANT ligands compounds are preferably part of a pharmaceutical composition when used in the methods of the present invention. The pharmaceutical composition will include at least one of a pharmaceutically acceptable carrier, diluent or excipient, in addition to one or more ANT ligands and, optionally, other components.

"Pharmaceutically acceptable carriers" for therapeutic use are well known in the pharmaceutical art, and are described, for example, in *Remingtons Pharmaceutical Sciences*, Mack Publishing Co. (A. R. Gennaro edit. 1985). For example, sterile saline and phosphate-buffered saline at physiological pH may be used. Preservatives, stabilizers, dyes and even flavoring agents may be provided in the pharmaceutical composition. For example, sodium benzoate, sorbic acid and esters of p-hydroxybenzoic acid may be added as preservatives. Id. at 1449. In addition, antioxidants and suspending agents may be used Id.

"Pharmaceutically acceptable salt" refers to salts of the compounds of the present invention derived from the combination of such compounds and an organic or inorganic acid (acid addition salts) or an organic or inorganic base (base addition salts). The compounds of the present invention may be used in either the free base or salt forms, with both forms being considered as being within the scope of the present invention.

The pharmaceutical compositions that contain one or more ANT substrates/ligands compounds may be in any form which allows for the composition to be administered to a patient. For example, the composition may be in the form of a solid, liquid or gas (aerosol). Typical routes of administration include, without limitation, oral, topical, parenteral (e.g., sublingually or buccally), sublingual, rectal, vaginal, and intranasal. The term parenteral as used herein includes subcutaneous injections, intravenous, intramuscular, intrasternal, intracavernous, intrameatal, intraurethral injection or infusion techniques. The pharmaceutical composition is formulated so as to allow the active ingredients contained therein to be bioavailable upon administration of the composition to a patient. Compositions that will be administered to a patient take the form of one or more dosage units, where for example, a tablet may be a single dosage unit, and a container of one or more compounds of the invention in aerosol form may hold a plurality of dosage units.

For oral administration, an excipient and/or binder may be present. Examples are sucrose, kaolin, glycerin, starch dextrins, sodium alginate, carboxymethylcellulose and ethyl cellulose. Coloring and/or flavoring agents may be present. A coating shell may be employed.

The composition may be in the form of a liquid, e.g., an elixir, syrup, solution, emulsion or suspension. The liquid may be for oral administration or for delivery by injection, as two examples. When intended for oral administration, preferred composition contain, in addition to one or more ANT substrates/ligands compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

A liquid pharmaceutical composition as used herein, whether in the form of a solution, suspension or other like form, may include one or more of the following adjuvants: sterile diluents such as water for injection, saline solution, preferably physiological saline, Ringer's solution, isotonic sodium chloride, fixed oils such as synthetic mono or digylcerides which may serve as the solvent or suspending medium, polyethylene glycols, glycerin, propylene glycol or other solvents; antibacterial agents such as benzyl alcohol or methyl paraben, antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid composition intended for either parenteral or oral administration should contain an amount of ANT substrates/ligands compound such that a suitable dosage will be obtained. Typically, this amount is at least 0.01 wt % of an ANT substrates/ligands compound in the composition. When intended for oral administration, this amount may be varied to be between 0.1 and about 70% of the weight of the composition. Preferred oral compositions contain between about 4% and about 50% of ANT substrates/ligands compound(s). Preferred compositions and preparations are prepared so that a parenteral dosage unit contains between 0.01 to 1% by weight of active compound.

The pharmaceutical composition may be intended for topical administration, in which case the carrier may suitably comprise a solution, emulsion, ointment or gel base. The base, for example, may comprise one or more of the following: petrolatum, lanolin, polyethylene glycols, beeswax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the ANT substrates/ligands compound of from about 0.1 to about 10% w/v (weight per unit volume).

The composition may be intended for rectal administration, in the form, e.g., of a suppository which will melt in the rectum and release the drug. The composition for rectal administration may contain an oleaginous base as a suitable nonirritating excipient. Such bases include, without limitation, lanolin, cocoa butter and polyethylene glycol.

In the methods of the invention, the ANT substrates/ligands compound(s) may be administered through use of insert(s), bead(s), timed-release formulation(s), patch(es) or fast-release formulation(s).

It will be evident to those of ordinary skill in the art that the optimal dosage of the ANT substrates/ligands compound(s) may depend on the weight and physical condition of the patient; on the severity and longevity of the physical condition being treated; on the particular form of the active ingredient, the manner of administration and the composition employed. It is to be understood that use of an ANT substrates/ligands compound in a chemotherapy can involve such a compound being bound to an agent, for example, a monoclonal or polyclonal antibody, a protein or a liposome, which assist the delivery of said compound.

EXAMPLES

The following Examples are offered by way of illustration and not by way of limitation.

Example 1

Cloning and Expression of His-Tagged Human ANT Proteins in Bacteria

A. PCR Amplification of ANT cDNAs

Total cellular RNA prepared from whole human brain was obtained from a commercial source (Clontech, Palo Alto, Calif.). The RNA was purified by treatment with RNase-free DNase I (Roche Molecular Biochemicals, formerly Boehringer Mannheim Biochemicals, Indianapolis, Ind.) using 1 ul of DNase I (10 u/ul) in a buffer containing 40 mM Trsi-HCl, pH 7.0, 6 mM magnesium chloride and 2 mM calcium chloride for 30 minutes at 37° C. This treatment was followed by two phenol/chloroform extractions, one chloroform extraction and an ethanol precipitation in the presence of sodium acetate. The RNA pellet was collected by centrifugation, washed with 70% ethanol, air dried, and resuspended in RNase-free sterile water. The RNA was reverse transcribed to generate cDNA using RNase H-deficient Reverse Transcriptase (SUPERSCRIPT™; Life Technologies, Rockville, Md.).

ANT cDNAs were amplified by polymerase chain reactions (PCR) in a thermal cycler using the following primers, AMPLITAQ™ DNA Polymerase (Perkin-Elmer), and reagents and buffers supplied in a GENEAMP™ PCR Reagent Kit (Perkin-Elmer), according to the manufacturer's instructions. In the following representations of the PCR primers, underlined nucleotides indicate sequences complementary to the 5'-ends and 3'-ends of the ANT cDNAs and double-underlined nucleotides indicate recognition sequences for the restriction enzymes XhoI (recognition sequence: 5'-CTCGAG) and Asp718 (recognition sequence: 5'-GGTACC).

For human ANT1 (huANT1; SEQ ID NO:1), the following primers were used:
Forward (sense):
5'-TTATATCTCGAGTATGGGTGATCACGCTTGGAGCT TCCTAAAG SEQ ID NO:4
and Reverse (antisense):
5'-TATATAGGTACCTTAGACATATTTTTTGATCTCATC ATACAAC SEQ ID NO:5.

For human ANT2 (huANT2; SEQ ID NO:2), the following primers were used:
Forward (sense):
5'-TTATATCTCGAGTATGACAGATGCCGCTGTGTCCT TCGCCAAG SEQ ID NO:6
and Reverse (antisense):
5'-TATATAGGTACCTTATGTGTACTTCTTGATTTCATC ATACAAG SEQ ID NO:7.

For human ANT3 (huANT3; SEQ ID NO:3), the following primers were used:

Forward (sense):
5'-TTATATCTCGAGTATGACGGAACAGGCATCTCCTT CGCCAAA SEQ ID NO:8
and Reverse (antisense):
5'-TATATAGGTACCTTAGATCACCTTCTTGAGCTCGT CGTACAGG SEQ ID NO:9.

B. Generation of ANT Expression Constructs

PCR products were digested with the restriction endonucleases XhoI and Asp718 (both enzymes from Roche Molecular Biochemicals) according to the manufacturer's recommendations using manufacturer-supplied reaction buffers. Restricted DNAs were purified by horizontal agarose gel electrophoresis and band extraction using the UltraClean GelSpin kit (Mo Bio Laboratories, Inc., Solana Beach, Calif.).

The expression vector pBAD/His ("B" derivative; Invitrogen, Carlsbad, Calif.) was used. This vector contains the following elements operably linked in a 5' to 3' orientation: the inducible, but tightly regulatable, araBAD promoter; optimized $E.\ coli$ translation initiation signals; an amino terminal polyhistidine(6×His)-encoding sequence (also referred to as a "His-Tag"); an XPRESS™ epitope-encoding sequence; an enterokinase cleavage site which can be used to remove the preceding N-terminal amino acids following protein purification, if so desired, a multiple cloning site, and an in-frame termination codon.

Plasmid pBAD/His DNA was prepared by digestion with the restriction endonucleases XhoI and Asp718 according to the manufacturer's instructions and subjected to horizontal agarose gel electrophoresis and band extraction using the UltraClean GelSpin kit (Mo Bio Laboratories). Restricted ANT cDNAs were ligated into the linearized plasmid with restricted expression vector DNA using T4 DNA ligase (New England Biolabs, Beverly, Mass.) using the manufacturer's reaction buffer and following the manufacturer's instructions. Competent recA1 hsdR endA1 $E.\ coli$ cells (strain TOP10F'; Invitrogen, Catalog #C3030-03) were transformed with ligation mixtures containing the prokaryotic vector construct according to the manufacturer's instructions. Single colonies were selected and grown in 3–5 ml of LB broth (Sambrook, J., Fritsch, E. F., and Maniatis, T., Molecular Cloning: A Laboratory Manual, Cold Spring Harbor Laboratory Press, Cold Spring Harbor, N.Y., 1989) containing 50 µg/ml ampicillin (Roche Molecular Biochemicals). Plasmid DNA was isolated from the bacterial cultures using the WIZARD™ Plus Series 9600 Miniprep Reagents System (Promega, Madison, Wis.).

The recombinant huANT nucleotide sequences present in the expression constructs were determined and their authenticity confirmed relative to the published ANT sequences (FIG. 1, See Neckelmann et al., Proc. Nat'l. Acad Sc. U.S.A. 84:7580–7584 (1987) for huANT1; Battini et al., J. Biol. Chem. 262:4355–4359 (1987) for huANT2, and Cozens et al., J. Mol. Biol. 206:261–280 (1989) for huANT3.) by DNA sequencing using the PRISM™ Ready BIG DYE™ Terminator Cycle Sequencing Kit (The Perkin-Elmer Corp., Norwalk, Conn.) and the following sequencing primers 5'-TATGCCATAGCATTTTTATCC (SEQ ID NO:10) and 5'-CGCCAAAACAGCCAAGCT (SEQ ID NO:11). For each human ANT sequence, both primers are located inside the vector sequence adjacent to the DNA insertion. Sequence data was analyzed using the SEQUENCE NAVIGATOR™ analysis software package (Perkin-Elmer). This huANT3 expression construct was named pMK3A-huANT3.

The expression plasmids encoding His-tagged human ANT1, ANT2 and ANT3 are referred to herein as follows: For human ANT1, "pMK1 (His-tagged huANT1)" or "pMK1"; for human ANT2, "pMK2 (His-tagged huANT2)" or "pMK2"; for human ANT3 "pMK3A (His-tagged hu ANT3" or "pMK3A"; for human ANT3 from which extraneous linker N-terminal amino acids are deleted as detailed below, "pMK3B (His-tagged hu ANT3, shortened epiotpe linker)" or "pMK3B". Plasmids pMK1, pMK2 and pMK3A have been deposited at the American Type Culture Collection (ATCC; Manassas, Va.) on Nov. 3, 1998, and given the accession numbers ATCC 98969, ATCC 98970 and ATCC 98971, respectively.

The expression constructs comprising nucleotide sequences encoding human ANT1 (pMK1-huANT1) and human ANT2 (pMK2-huANT2) were restriction mapped to confirm their structures. The nucleotide sequences of plasmids pMK1-huANT1 and pMK2-huANT2 are determined using the methods and primers (SEQ ID NOS:10 and 1) described above.

Treatment of the recombinant huANT3 protein expressed from pMK3A-huANT3 with enterokinase liberates the His-Tag/XPRESS™ epitope polypeptide from the huANT3 protein; however, the resultant huANT3 protein comprises several extraneous N-terminal amino acids (i.e., Pro-Ser-Ser-Ser-Met, where "Met" indicates the amino acid encoded by the translation initiation codon of huANT3). Although the extraneous amino acids probably have little or no effect on the recombinant huANT3 protein, a derivative expression construct in which the nucleotide sequence encoding the extraneous amino acids are deleted was prepared in the following manner.

The QUIK-CHANGE™ Site-Directed Mutagenesis Kit (Stratagene, La Jolla, Calif.) essentially according to the manufacturer's instructions. Briefly, a reaction mixture comprising purified pMK3A-huANT3 DNA, the mutagenic oligonucleotide primers 5'-GGAGATGGCCTGTTCCGTCAT CTTATCGTCATCGTCGTACAGATC (SEQ ID NO:12; the underlined sequence is the reverse complement of the 5' end of the huANT3 reading frame), and 5'-GATCTGTACGAC GATGACGATAAGATGACGGAACAGGCCATCTCC (SEQ ID NO:13; the underlined sequence corresponds to the 5' end of the huANT3 reading frame), Pfu DNA polymerase and dNTPs in manufacturer-supplied reaction buffer was prepared. The mutagenic oligonucleotide primers were present in excess and cycles of DNA synthesis was carried out in a thermal cycler according to the manufacturer's protocol. The reaction products were treated with the restriction enzyme DpnI, which cleaves methylated and hemi-methylated DNAs but leaves unmethylated DNA (i.e., annealed products of the reaction) intact, and used to transform EPICUREAN COLI™ XL-1-Blue $E.\ coli$ cells (Stratagene). Plasmid DNA was prepared from twelve randomly selected transformants and the nucleotide sequence of the region containing the multiple cloning site cassette was determined according to the methods described above. Of the twelve plasmids, only one retained the original sequence found in pMK-huANT3, and three contained undesired point mutations. One of the eight "correct" plasmids was chosen and named pMK3B-huANT3.

C. Expression of His-Tagged huANT3

Cultures of $E.\ coli$ cells containing pMK3A-huANT3 were grown in LB media containing 50 ug/ml ampicillin to mid-log phase ($OD_{600}$~0.5) and induced for 3–4 hours with increasing doses of arabinose (i.e., 0.00002%, 0.0002%, 0.002%, 0.02%, and 0.2%). One ml of each culture was centrifuged at 5,000×g for 10 minutes at 4° C. to pellet the cells. Cell pellets were resuspended, and the cells were lysed, by adding 100 ul of Phosphate Buffered Saline (PBS;

pH 7.4) containing 1% cholate, 1% n-dodecyl maltoside, and 0.1% 2-mercaptoethanol (in the preceding text, and throughout the specification, unless specified otherwise, all chemicals are from Sigma, St. Louis, Mo.). Total protein content in the lysates was determined using the BCA (bicinchoninic acid; Smith et al., 1985, *Anal. Biochem.* 150:76–85) Protein Assay kit (Pierce Chemical Co., Rockford, Ill.). Ten µg of total protein were loaded per lane onto an SDS polyacrylamide gel, electrophoresed and transferred to a nitrocellulose membrane (HYBOND™ ECL Nitrocellulose Membrane, Amersham Pharmacia Biotech, formerely Amersham Life Sciences, Piscataway, N.J.). Human ANT3 fusion proteins were detected in a western blot using ANTI-XPRESS™ Antibody (Invitrogen) and horseradish peroxidase-conjugated anti-mouse secondary antibody (Amersham Pharmacia Biotech) according to the manufacturers' instructions.

The results are shown in FIG. 3. From left to right in the figure, the following samples are shown: lanes "M", molecular weight markers; lane "0", untransformed *E. coli* cells; lane "o/n", *E. coli* comprising pMK3A-huANT3 grown overnight without induction; lane "1"–"5", *E. coli* comprising pMK3A-huANT3 grown induced with increasing doses of arabinose (0.00002%, 0.0002%, 0.002%, 0.02% and 0.2%, respectively). As expected, untransformed (lane 0) and uninduced (lane o/n) *E. coli* showed no XPRESS™-huANT3 material. However, expression of recombinant ANT3 fusion protein with a molecular weight of 36.6 kD was observed in lanes 3 and 4 (0.002% and 0.02% arabinose, respectively). No XPRESS™-huANT3 material was detected in lanes 1 and 2 (0.00002% and 0.0002% arabinose, respectively) indicating that the degree of induction was insufficient under these conditions.

Cells that were grown in the presence of the highest concentration of arabinose (0.2%, lane 5) began to lyse and died before the time of harvest, consequently, no recombinant protein was detected. This indicated that very high expression of recombinant huANT in *E. coli* caused cell death, as is sometimes the case during overexpression of heterologous proteins in bacteria.

D. Recombinant huANT3 Localizes to the Bacterial Membrane

Figure 4:
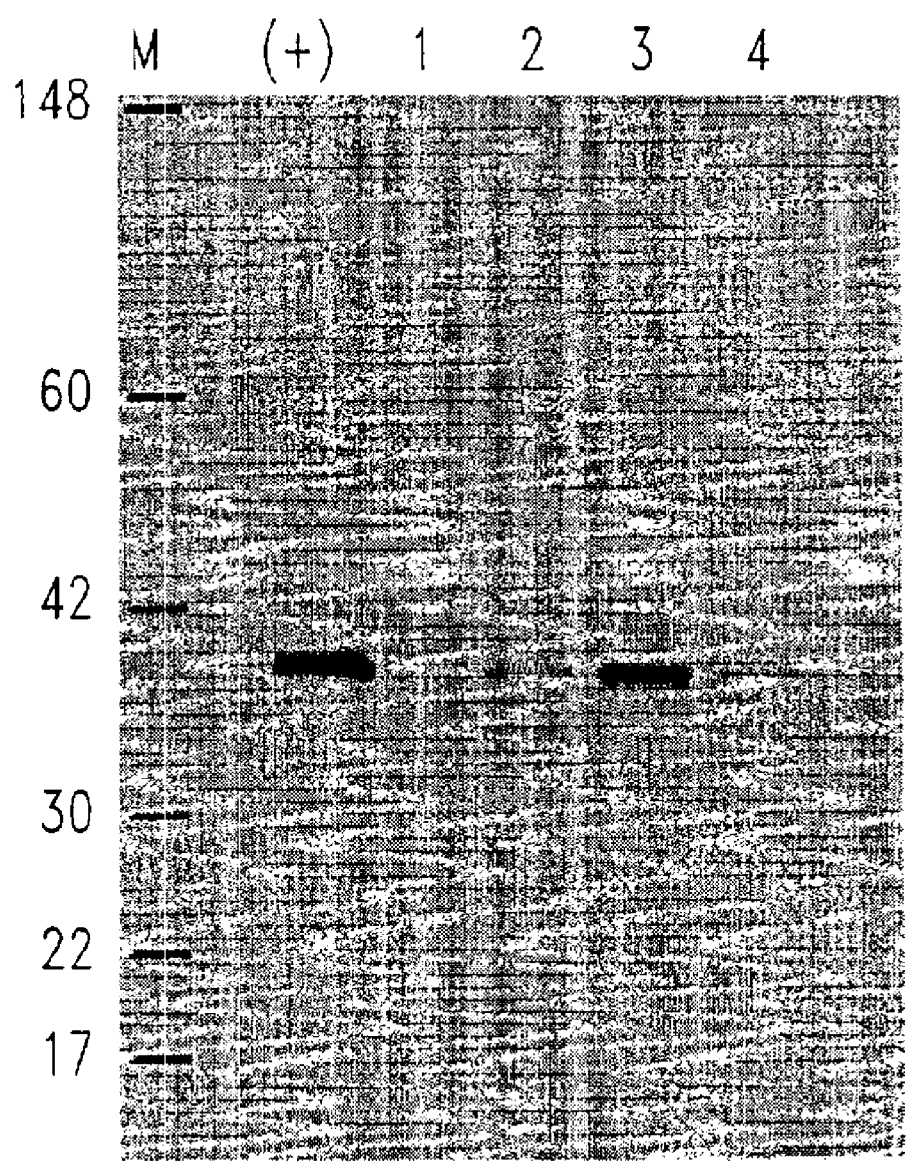
FIG. 4 shows the localization of His-Tagged, XPRESS™-epitope containg huANT3 protein in *E. coli* as determined by Western analysis.

In order to locate the expressed human ANT 3 within *E. Coli* cells, cells were grown in culture and induced with arabinose as described above, and then fractionated into different compartments (e.g., membranes, inclusion bodies and cytosol). Bacteria were pelleted by centrifugation at 5,000×g for 10 minutes at 4° C. The cell pellets were resuspended in ⅒ volume of cell buffer A (50 mM Tris-HCl, pH 8.0, 2 mM EDTA, 100 ug/ml lysozyme, and 0.1% Triton X-100) and incubated for 15 minutes at 30° C. in an orbital shaker. The cell mixture was sonicated for 2 minutes and membranes were pelleted by centrifugation at 12,000×g for 15 minutes at 4° C. The supernatant, representing the cytosol, was removed for analysis (FIG. 4, lane 4), as was a portion of the pellet containing membranes and inclusion bodies (FIG. 4, lane 3). The remaining portion of the pellet was washed twice with cell buffer B (10 mM Tris-HCl, pH 7.0, 0.1 mM EDTA, and 1 mM DTT) and centrifuged at 12,000×g for 15 minutes at 4° C. The pellet was resuspended in cell buffer C (20 mM Tris-HCl, pH 8.0, 100 mM sodium chloride, and 6 M guanidinium hydrochloride) and incubated for 1 hour at room temperature. The solution was then centrifuged at 12,000×g for 15 minutes at 4° C. The supernatant (containing solubilized inclusion bodies; lane 1, FIG. 4) and the pellet (containing insoluble inclusion bodies; lane 2, FIG. 4) were analyzed by Western blotting as described above.

The results are shown in FIG. 4. Recombinant huANT 3 (molecular weight 36.6 kD) was detected in lanes 2, 3, and 4, as well as the positive control lane (+) (total cell lysate previously tested for presence of ANT3 protein by Western immunoblot analysis, as described above). The greatest amount of recombinant huATN3 was detected in lane 3, which represents the membrane fraction. This indicates that the majority of the huANT3 fusion protein integrated into the *E. Coli* cellular membrane. Smaller protein signals were visible in lanes 2 and 4, representing the insoluble inclusion body fraction which might have contained some membranes with integrated ANT 3, and the cytosolic fraction where protein synthesis takes place. No protein was detectable in the soluble inclusion body fraction in lane 1, indicating that controlled expression of ANT3 in the bacteria did not result in the formation of inclusion bodies, which is an undesirable consequence of over-expression of some heterologous proteins in bacteria.

E. Purification of ANT Proteins

ANT proteins, and ANT fusion proteins, produced by the expression systems described herein have been purified using a variety of methods. The purification of ANT proteins, particularly human ANT proteins, is described in this Example.

Regardless of which of following protein purification methods is used, or others that can be derived from the present disclosure, it is important to add sufficient amounts of DNase and RNase to eliminate the viscosity associated with some bacterial lysates (typically 10 µg/mL of each enzyme, both from Roche Biochemicals) when the bacterial cells are lysed (or immediately thereafter). An alternative or additional means by which viscosity has been minimized and ANT solubility has been optimized is vigorous sonication, as opposed to standard sonication, of the lysates. The term "vigorous sonication" refers to, for example, sonication with a Branson Sonifier (Model 450) 2× (30 seconds each time) at 50% duty cycle and 80% output using a tapered, flat-tipped probe (as opposed to sonication with a cup and horn apparatus). Although either type of sonication will suffice, better yields have typically been observed when vigorous sonication has been used.

Furthermore, in various ANT purification methods that have been used, it was often desirable to make the lysate at least 1% Triton-X, in order to solubilize the maximum possible amount of ANT protein, after which insoluble material is removed by a high-speed (i.e., about 100,000 g) spin. Typically, protease inhibitors such as, for example, pepstatin, leupeptin, phenylmethylsulfonyl fluoride (PMSF) and/or aprotinin (all from Sigma) have been present at effective levels (typically 10 µg/mL) during the preparation. Depending on the particular ANT protein or ANT fusion protein being isolated, all four protease inhibitors or any effective combination thereof are used. For example, in preparations of GST-huANT3 fusion proteins, best results were seen when all four protease inhibitors were used, although acceptable results have been obtained when only leupeptin and pepstatin were used.

One method incorporates novel methods with several techniques previously used only for purifying ANT proteins from non-human mammals, i.e., bovine cardiac tissue and rats (Aquila et al., 1982, *Hoppe-Seyler's Z. Physiol. Chem.* 363:345–349; and Sterling, 1986, *Endocrinology* 119:292–295). In brief, bacterial cells expressing a GST-ANT3 fusion protein were lysed by lysozyme treatment, and $^{14}$C-palmityl-CoA (Sigma) was added at a concentration of 50 nmol per gram of *E. coli*. Because it associates with ANT proteins, $^{14}$C-palmityl-CoA acts as a radiolabeled tracer that can be used to follow the ANT protein in subsequent purification steps. The lysates were then sonicated and made 6% Triton X-100 (Sigma) and incubated at 4° C. for 1 hr to solubilize material. A high-speed spin was used to remove insoluble material, and the resulting solute was applied either (1) for small scale preparations, to hydroxyapatite beads (Bio-Rad Laboratories, Hercules, Calif.), or (2) in the case of larger preparations (i.e., ≧1 liter of bacterial culture), to a hydroxyapatite column (Bio-Rad) essentially according to the manufacturer's instructions. Unlike other intramembrane mitochondrial proteins, ANT has a low affinity for hydroxyapatite (Klingenberg et al., 1978, *Biochim. et Biophys. Acta* 503:193–210). The hydroxyapatite column was eluted with Column Buffer A (10 mM MOPS, pH 7.2, 100 Mm NaCl, 9.5% Triton X100) and washed with Column Buffer B (10 mM MOPS, pH 7.2, 100 mM NaCl, 400 mM sodium phosphate). Non-recombinant ANT proteins from non-human species are eluted in the void volume with Column Buffer A, and the GST-huANT3 fusion protein was expected to be present in the void volume as well; Column Buffer B was used to wash the column in the event that GST-huANT3 fusion protein behaves differently. Samples were collected in such a manner as to have a final concentration of 30 of mM octyl glucoside (Calbiochem), a non-ionic detergent that helps solubulize ANT proteins with minimal effect on activity (Sterling, 1986, *Endrocrinol.* 119: 292–295). The bead-extracted supernatant or column eluent was collected, and Triton X-100 was removed therefrom using the EXTRACTI-GEL™ affinity matrix (Pierce) essentially according to the manufacturer's instructions (see also Berman et al., 1985, *Biochemistry* 24:7140–7147).

Varying amounts of GST-huANT3 prepared in the above manner were subject to PAGE and the gel was stained using a colloidal blue protein stain (Novex, San Diego, Calif.). The stained gel displayed a single band having a molecular weight corresponding to that predicted for the fusion protein. Based on the intensity of bands from samples of varying volumes, and the known volume of the preparation and minimal sensitivity of the stain, the yield from 100 mL of bacterial culture was estimated to be about 50 ug. In one of the lanes of the gel, approximately 500 ng of protein was loaded, and no contaminating bands were detected, this indicates that the GST-huANT3 protein was from at least about 90% pure to at least about 95% pure.

GST-huANT3 fusion proteins (see preceding Examples) have been purified by this method, and other ANT fusion proteins, including His-tagged huANT3 and other His-tagged ANT proteins, are purified in like fashion. Purified huANT fusion proteins are used to produce purified human ANT proteins as follows.

GST-huANT fusion proteins are further purified via glutathione-agarose beads (Sigma) essentially according to the manufacturer's instructions. In brief, a solution comprising GST-huANT fusion proteins is contacted with glutathione-agarose beads, and the beads are washed to release undesirable contaminants. Next, the [bead:GST-huANT] complexes are treated with an appropriate enzyme, i.e., one that separates the huANT polypeptide from the remainder of the fusion protein. In the case of the GST-huANT3 fusion protein described herein (i.e., that encoded by pMK3C), thrombin (Sigma) cleaves the fusion protein in such a manner so as to produce two polypeptides: a first polypeptide corresponding to the GST moiety, and a second polypeptide which corresponds to human ANT3 with an additional six amino acids (i.e., Gly-Ser-Pro-Gly-Ile-Leu) present at its N-terminus.

His-tagged huANT fusion proteins are further purified via Nickel-coated resins (such as, e.g., PROBOND™ $Ni^{2+}$ charged agarose resin; Invitrogen) essentially according to the manufacturer's instructions. In brief, a solution comprising His-tagged huANT fusion proteins is contacted with the Nickel-coated resin, and the resin is washed to release undesirable contaminants. Next, the [resin:His-tagged huANT] complexes are treated with an appropriate enzyme, i.e., one that separates the huANT polypeptide from the remainder of the fusion protein. In the case of the His-tagged huANT3 fusion proteins described herein, enterokinase (Sigma, or EKMAX™ from Invitrogen may be used) cleaves the fusion protein in such a manner so as to produce two polypeptides: a first polypeptide comprising the His-tag and XPRESS™ epitope moieties, and a second polypeptide which corresponds to human ANT3. If the expression construct used is pMK3A, the resultant purified human ANT3 protein has an additional four amino acids (i.e., Pro-Ser-Ser-Ser) at its N-terminus. If pMK3B is the expression construct present in the cells from which His-tagged huANT3 is isolated, the resultant purified human ANT3 protein has the sequence of native huANT3, i.e., SEQ ID NO:3.

In both of the preceding purification steps, an ANT fusion protein bound to a solid support is treated with an enzyme (i.e., thrombin or enterokinase) that liberates an ANT protein from the remainder of the fusion protein, which remains bound to the solid support. ANT protein is released into the liquid phase which is then collected to generate a solution comprising the ANT protein and some amount of the liberating enzyme. The amount of liberating enzyme needed is minimal because the treatment is catalytic in nature; nevertheless, some enzyme remains in the preparation. If desired, enzyme molecules may be removed from the preparation using any of a variety of means known in the art. For example, an enzyme may be removed from a solution by contacting the solution with a resin conjugated to a ligand having a high affinity for the enzyme. In the case of enterokinases, one such resin is the EK-AWAY™ resin (Invitrogen) which comprises the soybean trypsin inhibitor having a high affinity for enterokinases. Methods of treating GST fusion proteins with thrombin and purifying the desired recombinant protein have been described previously (see, for example, Smith and Corcoran, Unit 16.7 in Chapter 16 in *Short Protocols in Molecular Biology* $2^{nd}$ Ed., Ausubel et al, eds, John Wiley & Sons, New York, N.Y., 1992, pages 16–28 to 16–31. In general, however, any suitable means for separating the liberating enzyme from any given ANT protein may be used.

F. Growth Inhibition

As noted in the above discussion of the results presented in FIG. 3, very high expression of recombinant huANT3 in *E. coli* caused cell death. Such a result is sometimes observed during over-expression of heterologous proteins in bacteria. Although not wishing to be bound by any particular theory, because the recombinant huANT3 protein localized to the bacterial membrane, and because ANT3 functions as an ATP/ADP exchanger in the inner mitochondrial membrane and under appropriate conditions may exhibit pore properties suggestive of a role in membrane permeability, one possible explanation for the observed cell death would be an inappropriate enhancement of the permeability of the bacterial membrane. If this in fact the case, inhibitors of mitochondrial ANT might prevent the death of *E. coli* overexpressing huANT3. As noted above, under certain conditions atractyloside or bongkrekic acid may exhibit inhibition of ANT activity, such that either of these inhibitors, other known ANT-active agents and potentially other ANT ligands as provided herein may be employed in the instant Example described using bongkrekic acid.

In order to test this hypothesis, the following experiments are carried out. E. coli harboring pMK3A-huANT3 are grown with no arabinose or with 0.2% or more arabinose, the latter concentration having been previously shown to induce toxic levels of huANT3, and various concentrations (0, 5, 20, 50 and 200 µM of bongkrekic acid (Biomol Research Laboratories, Inc., Plymouth Meeting, Mass.), an inhibitor of ANT (Henderson and Lardy, 1970, *J. Biol. Chem.* 245:1319–1326) that binds to ANT (sec, e.g., Vignais et al., 1976, *Biochim. Biophys.* 440:688–696). The ability of bongkrekic acid to prevent the lysis of *E. coli* overexpressing huANT3, or any other ANT protein for that matter, indicates that the toxic effect of such overexpression is due to an activity associated with normally functioning ANT.

ANT proteins produced by this expression system, and others described herein, are also purified using known methods for purifying ANT proteins from humans and other mammals. See for example, Klingenberg et al., 1978 *Biochim. Biophys. Acta* 503:193–210; Aquila et al., 1982 *Hoppe-Seyler's Z. Physiol. Chem.* 363:345–349; and Sterling, 1986 *Endocrinol.* 119:292–295.

The bacterial toxicity of extreme overexpression of ANT in this system can be used to screen and identify novel inhibitors of ANT, as such compounds will be expected to also prevent lysis of *E. coli* overexpressing ANT proteins. In order to achieve a greater degree of specificity for the ANT protein produced from an expression vector, the yeast expression system for ANT proteins (see Example 4, infra) is used in a mutant yeast strain that is resistant to bongkrekic acid (Lauquin et al., 1975 FEBS Letters 35:198–200).

Example 2

Expression of GST-huANT3 Fusion Proteins
A. Generation of GST-huANT3 Expression Constructs Human ANT3 cDNA was amplified from pMK3A-huANT3 by PCR as in Example 1 but using the following primers. In the following representations of PCR primers, underlined nucleotides indicate sequences complementary to the 5'-ends and 3'-ends of the ANT cDNAs and double-underlined nucleotides indicate recognition sequences for the restriction enzymes XhoI (recognition sequence 5'-CTCGAG) or EcoRI (recognition sequence: 5'-GAATTC).

The primers used for PCR amplification were:
Forward (sense):
5'-CCCGGGGAATTCTGATGACGGAACAGGCCATCT CC SEQ ID NO:14
and Reverse (antisense):
5'-CCCGGGCTCGAGTTAGAGTCACCTTCTTGAGCTC SEQ ID NO:15

The expression vector pGEX-4T-2 (Amersham Pharmacia Biotech) was used to generate huANT3 fusion proteins comprising an enzymatic polypeptide and an ANT polypeptide. This vector comprises a lacI$^q$ (repressor) gene a tac promoter operably linked to a glutathione S-transferase (GST) gene from *Schistosoma japonicum*. (Smith et al., 1988, *Gene* 67:31–40), the coding sequence of which has been modified to comprise a thrombin cleavage site-encoding nucleotide sequence immediately 5' from a multiple cloning site. GST fusion proteins can be detected by Western blots with anti-GST or by using a calorimetric assay; the latter assay utilizes glutathione and 1-chloro-2-4-dinitrobenzene (CDNB) as substrates for GST and yields a yellow product detectable at 340 nm (Habig et al., 1974, *J. Biol. Chem.* 249:7130–7139). GST fusion proteins produced from expression constructs derived from this expression vector can be purified by, e.g., glutathione affinity chromatography, and the desired polypeptide released from the fusion product by thrombin. Thus, this expression vector provides for the rapid purification of fusion proteins, and release of proteins with relatively few extraneous N-terminal amino acids, although the resulting recombinantly produced protein contains two additional amino acids at the amino terminus (Gly-Ser). The tac promoter may be induced by the addition to cultured cells of, e.g., 1–5 mM isopropyl-beta-D-thiogalactopyranoside (IPTG; Fluka, Milwaukee, Wis.) and provides for high-level expression.

Plasmid pGEX-4T-2 was prepared by digestion with the restriction endonucleases EcoRI and Asp718 according to the manufacturer's instructions and subjected to horizontal agarose gel electrophoresis and band extraction using the UltraClean GelSpin kit (Mo Bio Laboratories). Restricted ANT cDNAs were ligated with the restricted expression vector DNA as described in the preceding Example. Single colonies were selected for grown in 3–5 ml of LB broth containing 50 ug/ml ampicillin (Roche Molecular Biochemicals), and plasmid DNA was isolated from the bacterial cultures using the WIZARD™ Plus Series 9600 Miniprep Reagents System (Promega). To confirm their authenticity, the recombinant huANT nucleotide sequences present in the pGEX deriavtive plasmid were determined as described in the preceding Example using the previously described oligonucleotide primers and 5' and 3' PGEX Sequencing Primers (Amersham Pharmacia Biotech).

The resultant GST-huANT3 expression construct was named pMK3C-GST-huANT3 (also referred to herein as pMK3C). Plasmid pMK3C has been deposited at the American Type Culture Collection (ATCC; Manassas, Va.) on Nov. 3, 1998, and given the accession number ATCC 98973. Thrombin treated recombinant huANT3 protein produced from the pMK3C-GST-huANT3 expression construct includes several extraneous N-terminal amino acids, i.e., Gly-Ser-Pro-Gly-Ile-Leu-Met, where "Met" indicates the amino acid encoded by the translation initiation codon of huANT3. There is, however, no evidence that the extraneous six amino terminal amino acids have any effect on the resultant recombinant huANT3 protein.

In order to confirm expression of the GST-huANT3 fusion protein, the following experiments were carried out. Eight independently isolated pMK3C-GST-huANT3 transformants and one control (vector-transformed) isolate were grown overnight in LB-ampicillin and then diluted 1:20 in 2 ml of fresh media. After 3 hours of growth at 37° C., IPTG was added to a final concentration of 0.1 mM. Cell growth was continued for 2 hours, after which 1.5 of cells were transferred to microfuge tubes, pelleted, resuspended in 300 uL of cold PBS containing 1% Triton X-100, and sonicated twice for 8 seconds. The sonicates were spun for 5 min. at 4° C., the supernatant was transferred to fresh microfuge tubes and 50 uL of glutathione-agarose beads (Sigma) were added to produce a 50% slurry. After a 5 min. incubation at ambient temperature, the beads were spun and washed with 1 ml of PBS three times. The washed pellet was resuspended in SDS spl buffer (62.5 mM Tris, pH 6.8, 2% SDS, 10% glycerol, 5% beta-mercaptoethanol and sufficient bromophenol blue to provide visible coloration), and 30 uL of each preparation (equivalent to 15 uL of culture) was subjected to SDS-PAGE. The gel was stained using a Colloidal Coomassie (G-250) Staining Kit (Novex, San Diego, Calif.). A band of the predicted molecular weight of the GST-huANT3 fusion protein was readily apparent, with the same intensity, in each of the 8 preparations from pMK3C-GST-huANT3 transformants, this band was absent in the control preparation.

B. Western Blot Analysis of Expression of huANT3 Fusion Proteins

*E. coli* transformed with either (1) pMK3A-huANT3 (the pBAD/His-huANT3 expression construct) or (2) pMK3C-GST-huANT3 (the pGEX/GST-huANT3 expression construct) were lysed by the addition of lysozyme (100 µg/µl; Sigma) for 20 min at room temperature, followed by one freeze/thaw cycle. The negative control for the former transformant was a parallel culture of the transformed cells that had not undergone arabinose induction. The control for the latter transformant was a parallel culture of *E. coli* that had been transformed with the pGEX-4T-2 vector only.

Total protein concentrations of each lysate were determined using the BCA Protein Assay kit (Pierce Chemical Co.), and equivalent amounts of total protein from each lysate preparation were mixed with equivalent volumes of 2× Laemmli electrophoresis buffer and subjected to SDS-PAGE. The proteins were electrophoretically transferred to nitrocellulose, which was then contacted with antibodies against the appropriate epitope included in each vector (i.e., ANTI-XPRESS™ from Invitrogen for pMK3A-huANT3 and polyclonal goat anti-GST from Amersham Pharmacia Biotech, formerly Nycomed Amersham plc and Pharmacia & UpJohn Inc. for pMK3C-GST-huANT3).

In a separate experiment, the bacterial lysate from the pMK3C-GST-huANT3 transformants was incubated with agarose-glutathione beads (Sigma) according to the manufacturer's instructions (see the preceding section and Smith et al., Expression and Purification of Glutathione S-Transferase Fusion Proteins, Unit 16.7 of Chapter 16 in: *Short Protocols in Molecular Biology*, 2nd Ed., Asubel et al., eds., John Wiley & Sons, New York, N.Y., 1992, pages 16–28 to 16–31). The beads were suspended in Laemmli sample buffer and subjected to SDS-PAGE and Western analysis as described above. Although the yield of GST-huANT3 was low, perhaps because the fusion protein is inserted into the bacterial membrane, a sufficient amount of material was recovered for the experiment.

Figure 5:
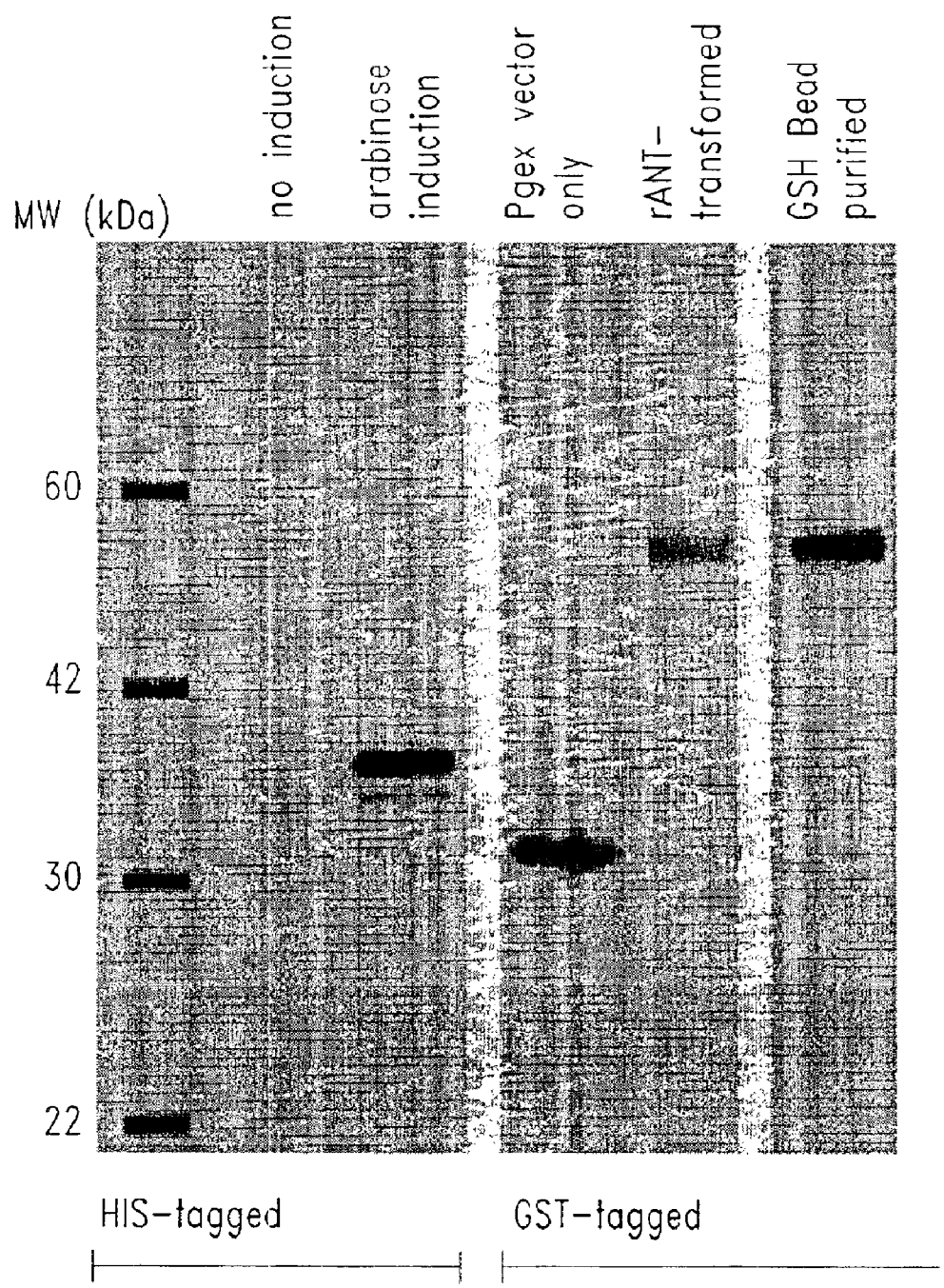
FIG. 5 shows the expression of human ANT3 (huANT3) in *E. coli* expression systems.

The results (FIG. 5) show that a specific band of the predicted molecular weight (His-Tag+enterokinase site+antigenic site+huANT3=38 kDa) was observed in the arabinose induced *E. coli* that were transformed with the pBAD/his-huANT3 vector, but was absent in the non-induced control culture. Similarly, a band corresponding to GST-huANT3 was observed in the pMK3C-GST-huANT3-transformed *E. coli*, while only the unaltered GST band was observed in control *E. coli* transformed with the expression vector. Purification of the GST-huANT3 fusion protein using agarose-GSH beads produced a band of equivalent size to that observed in the crude lysate of pMK3C-GST-huANT-transformed bacteria.

Example 3

Expression of ANT3 in Insect Cells

A. Generation of Baculovirus Expression Constructs

DNA comprising nucleotide sequences encoding huANT3 was amplified by PCR from a whole human brain cDNA library (Clontech) using the following primers. In the following representations of PCR primers, underlined nucleotides indicate sequences complementary to the 5'-ends and 3'-ends of the ANT cDNAs and double-underlined nucleotides indicate recognition sequences for the restriction enzymes BamHI (recognition sequence: 5'-GGATCC) or EcoRI (recognition sequence: 5'-GAATTC).

The PCR primers used were:

Forward (sense):
5'-TTATAGGATCCATCCATGACGGAACAGGCCATCT CCTTCGCCAAA SEQ ID NO:16 and Reverse (antisense):
5'-TTAAAGATTCTTAGATCACCTTCTTGAGCTCGTC GTACAG SEQ ID NO: 17.

PCR products were digested with the restriction endonucleases BamHI (New England Biolabs) and EcoRI (New England Biolabs) according to the manufacturer's recommendations. Subsequent purification was carried out by horizontal agarose gel electrophoresis and band extraction using the UltraClean GelSpin kit (Mo Bio Laboratories, Inc.).

The Baculovirus transfer vector pBlueBacHis2 (B version, Invitrogen) comprises, in 5' to 3' orientation, a constitutive polyhedrin promotor operably linked to nucleotide sequences encoding (1) a translation initiation sequence, (2) an N-terminal polyhistidine sequence, (3) an XPRESS™ epitope tag for detection and purification of the recombinant protein and (4) an enterokinas cleavage site, followed by a multiple cloning site wherein cDNAs can be inserted.

The transfer vector pBlueBacHis2 was prepared by digestion with the restriction endonucleases BamHI and EcoRI according to the manufacturer's recommendation, and the restricted DNA was subject to horizontal agarose gel electrophoresis and band extraction using the UltraClean Gel-Spin kit (Mo Bio Laboratories, Inc.). The restricted PCR products were ligated with the restricted expression vector DNA as in the preceding Examples.

Competent *E. coli* TOP10F' cells (Invitrogen) were transformed with the ligation recation following the manufacturer's instructions. Single colonies were selected for growth in 3–5 ml of LB broth containing 50 ug/ml ampicillin. Plasmid DNA was isolated from the bacterial cultures using the WIZARD™ Plus Series 9600 Miniprep Reagents System (Promega).

The recombinant ANT gene sequences were determined and their authenticities confirmed (SEQ ID NOS:1, 2 and 3 correspond to human ANTs 1, 2 and 3, respectively) by DNA sequencing using the Prism Ready Dye Terminator Cycle Sequencing Kit (Perkin-Elmer, Catalog #402080) and the following primers: Polyhedrin Forward Sequencing Priming Site, 5'-AAATGATAACCATCTCGC (SEQ ID NO:18); Baculovirus Reverse Sequencing Priming Site, 5'-ACTTCAAGGAGAATTTCC (SEQ ID NO:19); primers internal to the ANT 3 coding sequence (sense strand), 5'-ACTTCGCCTTCACGGATA (SEQ ID NO:20); and 5'-TACGGCCAAGGGCATTCT (SEQ ID NO:21); primers internal to the ANT 3 coding sequence (antisense strand), 5'-TGAAGCGGAAGTTCCTAT (SEQ ID NO:22); and 5'-ATGCCGGTTCCCGTACGA (SEQ ID NO:23). Sequence data were analysed using the SEQUENCE NAVIGATOR™ analysis software package (Perkin-Elmer). An isolated plasmid having the correct sequence was named pMK4A-huANT3.

Although pMK4A-huANT3 contains authentic huANT3-encoding sequences, the ANT3 reading frame is not synchronous with the reading frame of the His-Tag/XPRESS™ epitope of the expression vector. Accordingly, pMK4A-huANT3 is not expected to produce recombinant ANT protein, although cells harboring it may be used as controls.

In order to generate an in-frame derivative of pMK4A-huANT3, the plasmid was mutagenized using the QUIK-CHANGE™ Site-Directed Mutagenesis Kit (Stratagene) as in Example 1, except that the mutagenic oligonucleotide primers used were 5'-GGCCTGTTCCGTCATCTTATCGT CATCGTCG (SEQ ID NO:24; the underlined sequence is the reverse complement of the 5' end of the huANT3 reading frame), and 5'-CGACGATGACGATAAGATGACGGAAC AGGCC (SEQ ID NO:25; the underlined sequence corresponds to the 5' end of the huANT3 reading frame). Several transformants were isolated, and plasmid DNA purified therefrom. The nucleotide sequences of the plasmid DNAs were determined and one having the "correct" sequence was identified and named pMK4B-huANT3.

The baculovirus expression plasmids encoding human ANT3 are referred to as "pMK4A (baculovirus shuttle, out-of-frame hu ANT3)" or "pMK4A"; and "pMK4B (baculovirus shuttle, in-frame hu ANT3)" or "pMK4B". Plasmid pMK4B has been deposited at the American Type Culture Collection (ATCC; Manassas, Va.) on Nov. 3, 1998, and given the accession number ATCC 98972.

In order to insert sequences encoding the huANT3 protein (and associated regulatory sequences) into the baculovirus genome, insect cells (MAXBAC™ *Spodoptera frugiperda* S9 cells, Invitrogen, Carlsbad, Calif., or *Trichoplusia ni* cells, PharMingen, San Diego, Calif.) were co-transfected with the baculoviral transfer construct pMK4B-huANT3 and linear baculoviral (*Autographa californica* nuclear polyhedrosis virus, AcMNPV) DNA engineered to contain a promoterless 3' fragment of the lacZ gene (BAC-N-BLUE™, Invitrogen) using the BAC-N-BLUE™ Transfection Kit (Invitrogen) following the manufacturer's instructions. Recombinant baculovirus plaques express functional beta-galactosidase and were identified as blue plaques in the presence of X-gal (5-bromo-4-chloro-3-indoyl-beta-D-glactosidase). These recombinant viruses are expression constructs that express human ANT3 polypeptide in insect cells, as shown by the following experiments.

B. Western Blot Analysis of Baculovirus Expression Systems

High titer viral stock was produced, and recombinant protein was expressed in infected Sf9 (Invitrogen, Carlsbad, Calif.) or *T. ni* (PharMingen, San Diego, Calif.) cells according to the manufacturer's instructions (see also Piwnica-Worms, Expression of Proteins in Insect Cells Using Baculovirus Vectors, Section II of Chapter 16 in: *Short Protocols in Molecular Biology*, 2nd Ed., Asubel et al., eds., John Wiley & Sons, New York, N.Y., 1992, pages 16–32 to 16–48; Kitts, Chapter 7 in: *Baculovirus Expression Protocols, Methods in Molecular Biology*, Vol. 39, C. R. Richardson, Ed., Humana Press, Totawa, N.J., 1995, pages 129–142).

Transfected Sf9 cells were pelleted by centrifugation and lysed by adding 100 µl of MSB buffer (210 mM mannitol (Sigma), 70 mM sucrose (Fluka), 50 mM Tris-HCl, pH 7.4, 10 mM EDTA) and performing three freeze-thaw cycles. A total cellular fraction, a cytosolic fraction, a submitochondrial partical fraction, a mitochondrial fraction and a plasma membrane fraction were prepared as follows. The cell lysate was centrifuged at 600 g for 10 minutes at 4° C. to prepare a plasma membrane pellet. The supernatant was removed and set aside. The plasma membrane pellet was washed with 100 ul of MSB, centrifuged at 600 g for 10 minutes at 4° C., and used for the analysis. The supernatant was removed, combined with the first supernatant and mixed. Half of the supernatant was used to prepare a mitochondrial fraction and a cytosolic fraction by centrifugation at 14,000 g for 15 minutes at 4° C.; the pellet represents the mitochondrial fraction and the supernatant represents the cytosol. The other half of the supernatant was centrifuged at 14,000 g for 15 minutes at 4° C. to produce a mitochondria-containing pellet that was resuspended in MSB, incubated with 0.25 mg/ml digitonin (Roche Molecular Biochemicals, formerly Boehringer Mannheim, Indianapolis, 1N) for 2 min and sonicated for 3 min at 50% duty cycle in a cup-horn sonicator to produce submitochondrial particles (SMPs). (See Example 13 for details regarding mitochondrial preparation from transfected *T. ni* cells.)

The protein content for each fraction was determined using the BCA Protein Assay kit (Pierce Chemical Co.), and 8 ug of total protein were loaded per lane onto an SDS polyacrylamide gel, electrophoresed and transferred to a HYBOND™ ECL Nitrocellulose Membrane (Amersham Life Science). Fusion proteins were detected in a western blot using ANTI-XPRESS™ Antibody (Invitrogen, Catalog #R910-25) and horseradish peroxidase-conjugated anti-mouse secondary antibody (Amersham Life Science) following the manufacturers' instructions.

Figure 6:
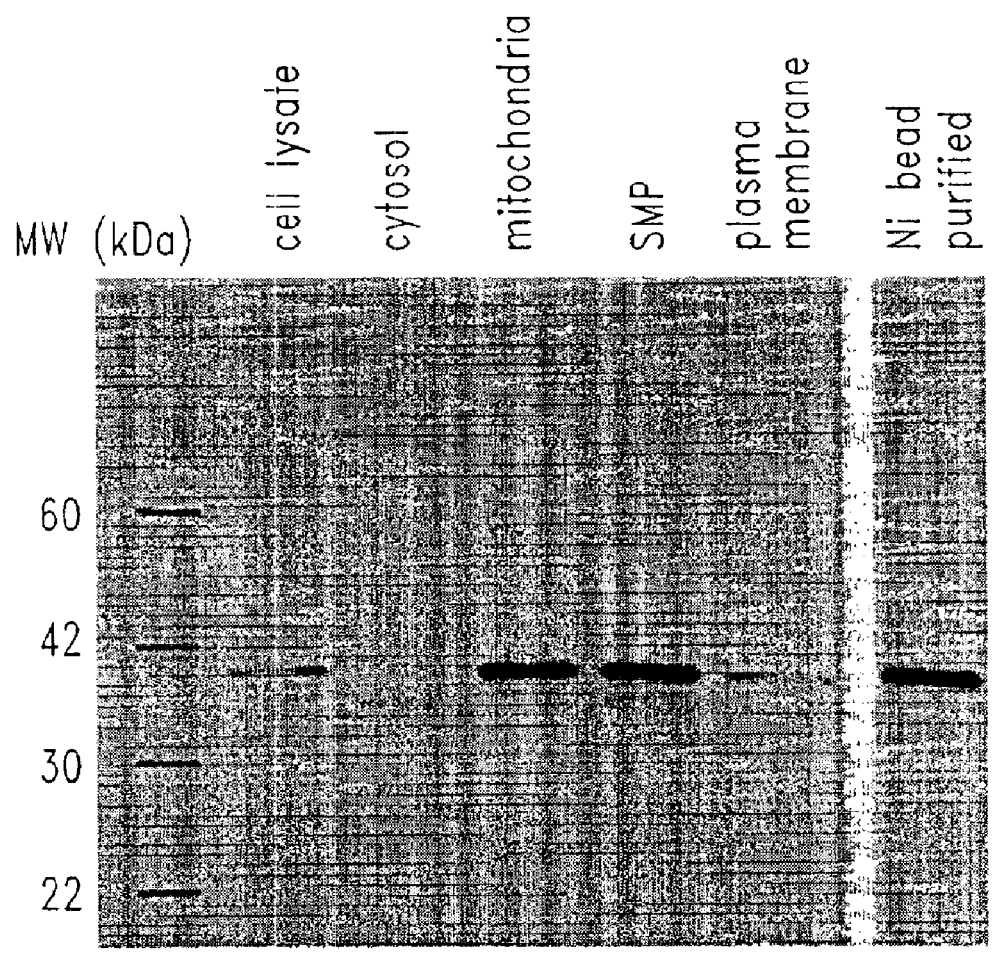
FIG. 6 shows the expression of huANT3 in baculovirus-infected Sf9 cells.

The results of the Western analysis are shown in FIG. 6. Recombinant GST-huANT3 fusion protein (molecular weight 36.6 kD) was detected in total cells, mitochondria, submitochondrial particles and the plasma membrane. The signal was most intense in mitochondria and submitochondrial particles, whereas no band was detectable in the cytosolic fraction. These data suggest that the human recombinant huANT3 fusion protein integrated into the mitochondrial membranes much more efficiently than into the plasma membranes. Furthermore, all of the recombinant protein integrated into membranes since no signal was detected in the cytosolic fraction. The final lane of the autoradiogram shows His-tagged huANT3 isolated from cell lysates using magnetic agarose beads coupled to Ni according to the manufacturers instructions (Qiagen; Hilden, Germany).

Thus, as in *E. coli*, huANT3 is expressed in the baculovirus/Sf9 system. Furthermore, recombinantly produced 6×His- and epitope-tagged huANT3 fusion protein is appropriately localized to the mitochondria in Sf9 cells despite the presence of over 35 extraneous N-terminal amino acids, and can be isolated from cellular fractions by means that take advantage of the His-Tag moiety's affinity for metals such as, e.g., nickel.

Example 4

Expression of ANT3 in Yeast

A. Expression Constructs and Host Cells

Human ANT3 cDNA was amplified by PCR as in Example 1 but using the following primers. In the following representations of PCR primers, underlined nucleotides indicate sequences complementary to the 5'-ends and 3'-ends of the ANT cDNAs and double-underlined nucleotides indicate recognition sequences for the restriction enzymes XhoI (recognition sequence: 5'-CTCGAG) or Asp718 (recognition sequence: 5'-GGTACC).

The primers used for PCR amplification were:
Forward (sense; SEQ ED NO:28):
5'-TTAATGGGTACCATGACGGAACAGGCCATCTCCT TCGCCAAA and
Reverse (antisense; SEQ ID NO:29):
5'-TTATACTCGAGTTAGATCACCTTCTTGAGCTCGTC GTACAGG.

PCR products, and expression vector DNAs, were digested with the restriction endonucleases XhoI and Asp718 (both enzymes from Roche Molecular Biochemicals) according to the manufacturer's recommendations using manufacturer-supplied reaction buffers. The expression vector pYES2 (Invitrogen) was used. This vector contains a multiple cloning site located immediately downstream from an inducible GAL1 promoter, as well as the 2u origin of replication and the *S. cerevisiae* URA3 gene for high-copy maintenance and selection in ura3 yeast cells, respectively.

The restricted DNAs were purified by horizontal agarose gel electrophoresis and band extraction using the UltraClean GelSpin kit (Mo Bio Laboratories), ligated to each other, and used to transform E. coli cells, as in the preceding Examples. Plasmid DNA was isolated from several transformants, and the nucleotide sequence of the insert DNA was determined and confirmed to be that of huANT3. One confirmed plasmid was chosen to be used for further study and was designated pMK5A (huANT3).

A second yeast huANT3 expression vector, pMK5B, was constructed as follows. Plasmids pMK5A and pYESTrp2 (Invitrogen) were digested with restriction enzymes BglI and PvuII (both from New England Biolabs) and gel purified, ligated and used to transform E. coli as above. The expression vector pYES2Trp is similar to pYES2 but comprises a TRP1selectable marker. Plasmid DNA was isolated from several transformants and restriction mapped to confirm the structure of the expected expression construct. One confirmed plasmid was chosen to be used for further study and was designated pMK5B (huANT3).

A third yeast huANT3 expression vector, pMK5C, was constructed using the expression vector pYPGE2, which comprises a TRP1 selectable marker and the strong PGK promoter upstream from a multiple cloning site (Brunelli and Pall, 1993 Yeast 9:1299–1308). Plasmid pYPGE2 DNA was digested with XhoI and Asp718, gel-purified and ligated with the XhoI- and Asp718-restricted huANT3 PCR product of Example 1. The ligation mixture was used to transform E. coli, and plasmid DNA was isolated from several transformants and restriction mapped to confirm the structure of the expected expression construct. One confirmed plasmid was chosen to be used for further study and was designated pMK5C (huANT3).

In order to generate yeast expression systems, the S. cerevisiae strain INVSc1 (MATα, his3Δl, leu2, trpl-289, ura3-52) was transformed with purified pMK5A, pMK5B and pMK5C DNAs using the S.c. EASYCOMP™ Transformation Kit (Invitrogen). A second S. cerevisiae strain, JΔ1Δ3 (MATα, ade2-1, leu2-3, leu2-112, his3-11, his3-15, trp1-1, ura3-1, can1-100, AAC1::LEU2. AAC2::HIS3, AAC3::URA3) was also transformed with the expression constructs. The AAC genes encode the three isoforms of the mitochondrial ADP/ATP translocator in S. cerevisiae and are interrupted in strain JΔ1Δ3 (Giraud et al., J. Mol. Biol. 281:409–418 (1998)). It is thus expected that transformants of JΔ1Δ3, which are incapable of expressing endogenous ANT (AAC) proteins, will only express the human ANT protein encoded by the expression construct with which they have been transformed.

B. Northern Blot Analyses of Yeast Expression Systems

In order to examine levels of huANT3 mRNA production in strain JΔ1Δ3, Northern analyses of cells transformed with pMK5B and pMK5C were performed according to methods known in the art. In brief, transformed cells and control (untransformed) cells grown to mid-log phase, harvested and lysed. RNA was extracted from the lysates, electrophoresed and transferred to a nitrocellulose filter (see Treco, Preparation of Yeast RNA, Unit 13.12 of Chapter 13 in Short Protocols in Molecular Biology, 2nd Ed., Asubel et al., eds., John Wiley & Sons, New York, N.Y. (1992), 13:44–46 and Seldon, Analysis of RNA by Northern Hybridization, Unit 4.9 of Chapter 4, Id., 4:23–25). The XhoI- and Asp718-restricted huANT3 PCR product of Example 1 was radiolabelled and used as a probe, and an RNA preparation from human spleen tissue was used as a positive control.

Figure 10:
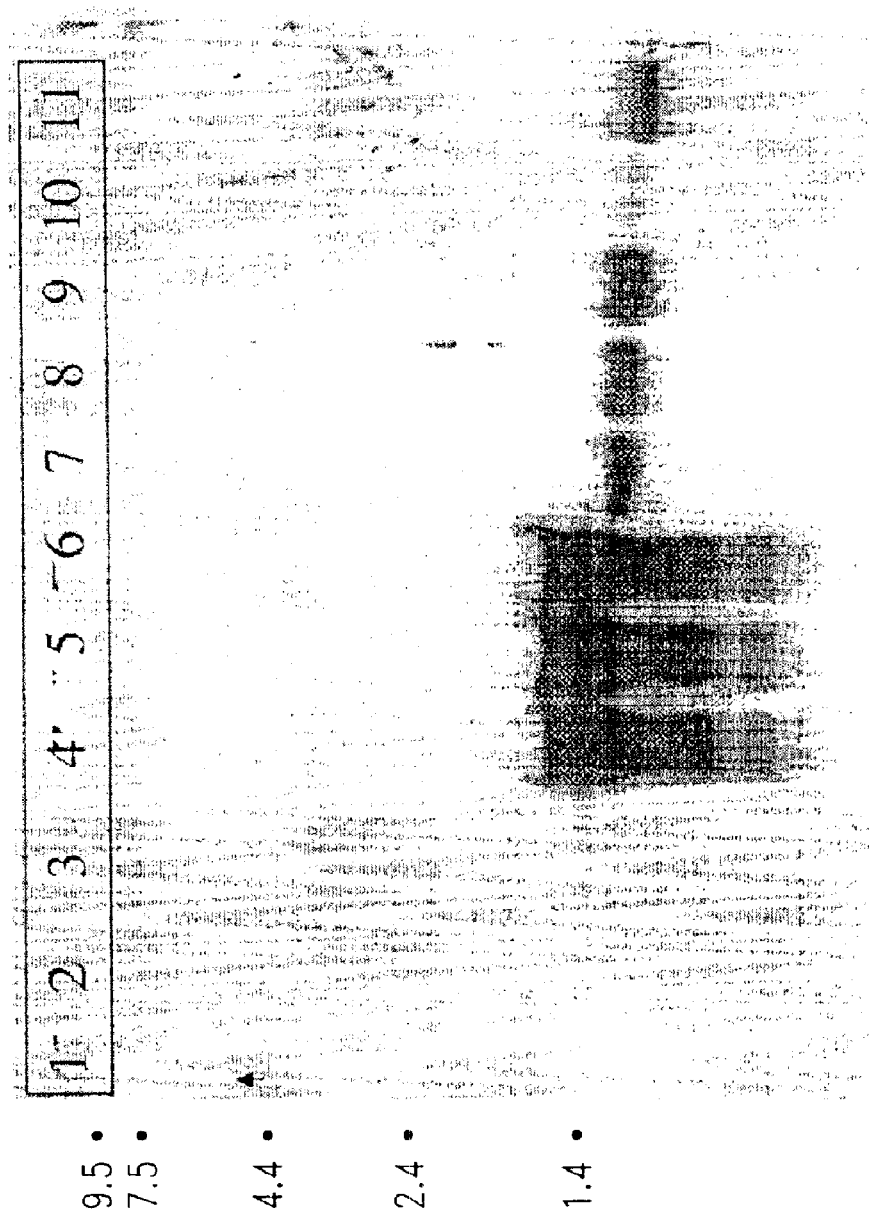
FIG. 10 shows Northern blot analysis of huANT3 transcripts detected in a yeast expression system. Lane contents: lane "M," molecular weight markers (positions of 1.4, 2.4, 4.4 and 7.5 kilobase markers indicated); lanes 1–3, [0 µg of RNA from three independent isolates of mock transformed AACyeast; lanes 4–6, 10 µg of RNA from three independent isolates of AACyeast transformed with pMK5C (pYPGE2-hANT3), lanes 7–9, 10 µg of RNA from three independent isolates of AACyeast transformed with pMK5B (pYESTrp2-hANT3); lanes 10 and 11, 0.2 (lane 10) and 0.8 (lane 11) µg of RNA prepared from samples of human spleen.

The results (FIG. 10) demonstrate the appropriately-sized ANT3-specific RNA is produced in human spleen and in yeast cells transformed with either expression vector, but not in untransformed yeast cells. The pYPGE2-derived expression construct pMK5C, which directs ANT3 expression from the PGK promoter, clearly results in more ANT3 RNA than the pYES2Trp-derived construct pMK5B, in which ANT3 expression is driven by the GAL1 promoter. In either case, however, significant levels of huANT3-specific RNA were produced in a yeast background that lacks any endogenous adenosine nucleotide translocator proteins.

C. Western Analyses of Yeast Expression Systems

1. Production of antibody to huANT3

As the huANT3 produced from the yeast expression constructs lacks an epitope tag, it was necessary to produce an antibody to huANT3 in order to evaluate recombinant production of the protein. A Nonspecific (antipeptide) antibody specific to huANT3 was prepared as follows.

A synthetic polypeptide corresponding to a portion of huANT3 located near the carboxy terminus and predicted to have high antigenicity according to the Jameson-Wolf Index (Wolf et al., Comput. Appl. Biosci. 4:187–191 (1988)) was synthesized using known means by Alpha Diagnostic International (San Antonio, Tex.) and determined to be at least about 70% pure, preferably at least about 90% pure, by HPLC and MS analyses. The sequence of the synthetic polypeptide (SEQ ID NO:30) is:

Cys-Trp-Arg-Lys-Ile-Phe-Arg-Asp-Glu-Gly-Gly-Lys-Ala-Phe-Phe

The synthetic polypeptide was conjugated to a carrier molecule, keyhole limpet hemocyanin (KLH), using MSB (m-maleimidobenzoyl-N-hydroxysuccinimide ester; Pierce Chemical Co., Rockford, Ill.), and the conjugated material was used to immunize several rabbits, according to known means (Collawn and Paterson, Units 11.14 and 11.15 in Chapter 11 in: Short Protocols in Molecular Biology, 2nd Ed., Asubel et al., eds., John Wiley & Sons, New York, N.Y. (1992) 11:3741. The rabbits were or are bled at 0 (preimmune, 2 mL), 7, 9, 11, 13 (15 mL for each bleed) or 15 weeks (50 μL) post-inoculation. Sodium azide (0.1%) was or is added to the bleeds as preservative.

2. Western Analyses

Western analyses of yeast expression systems are performed essentially as described in the preceding Examples, except that different methods are used to prepare protein preparations from yeast cells as opposed to bacterial or insect cells. Such methods of isolating proteins from yeast are known in the art (see, for example, Dunn and Wobbe, Preparation of Protein Extracts from Yeast, Unit 13.13 of Chapter 13 in Short Protocols in Molecular Biology, 2nd Ed., Asubel et al., eds. John Wiley & Sons, New York, N.Y. (1992), 13:46–50). The intracellular distribution of huANT3 in, e.g., membrane or mitochondrial fractions, is determined as in the preceding Examples.

Example 5

Expression of ANT3 in Mammalian Cells

The preceding Examples describe a variety of means by which ANT and ANT fusion proteins can be recombinantly produced in various systems. Although such ANT proteins can be used in a variety of assays (see infra), it may be desirable to isolate large amounts of the native ANT protein from mammalian cells. In particular, as described in this Example, it may be desirable to produce recombinant viral particles in which ANT proteins are displayed in the viral envelope. Such ANT-displaying viral particles are expected to be very stable and useful in a variety of assays including, for example, those in which compounds binding to ANT proteins are screened and identified.

Another useful outcome of mammalian expression systems is the generation and isolation of human mitochondria in which a particular ANT isoform is over-represented in order to determine the specific biological role(s) of such isoforms. For example, ANT3 is apparently ubiquitously expressed in human tissues, whereas ANT1 is primarily expressed in heart and skeletal muscle (Stepien et al., 1992, *J. Biol. Chem.* 267:14592–14597). Directed overexpression of huANT1 in cultured heart or muscle cells is expected to result in mitochondria that contain mostly the ANT1 isoform. Such "ANT isoform-enriched" mitochondria can be isolated and tested for various mitochondrial functions.

Constructs for expressing ANT proteins in mammalian cells are prepared in a stepwise process. First, expression cassettes that comprise a promoter (and associated regulatory sequences) operably linked to nucleotide sequences encoding an ANT protein are constructed in bacterial plasmid-based systems; these expression cassette-comprising constructs are evaluated and optimized for their ANT-producing ability in mammalian cells that are transiently transfected therewith. Second, the ANT expression cassettes are transferred to viral systems that produce recombinant proteins during lytic growth of the virus (e.g., SV40, BPV, EBV, adenovirus; see below) or from a virus that can stably integrate into and transduce a mammalian cellular genome (e.g., a retroviral expression construct).

A. Transient Expression

With regards to the first step, commercially available "shuttle" (i.e., capable of replicaton in both *E. coli* and mammalian cells) vectors that comprise promoters that function in mammalian cells and can be operably linked to an ANT-encoding sequence include, but are not limited to, SV40 late promoter expression vectors (e.g., pSVL, Pharmacia), glucocorticoid-inducible promoter expression vectors (e.g., pMSG, Pharmacia), Rous sarcoma enhancer-promoter expression vectors (e.g., pRc/RSV, Invitrogen) and CMV early promoter expression vectors, including deriavtives thereof having selectable markers to agents such as Neomycin, Hygromycin or ZEOCIN™ (e.g., pRc/CMV2, pCDM8, pcDNA1.1, pcDNA1.1/Amp, pcDNA3.1, pcDNA3.1/Zeo and pcDNA3.1/Hygro, Invitrogen). In general, preferred shuttle vectors for ANT genes are those having selectable markers (for ease of isolation and maintenance of transformed cells) and inducible, and thus regulatable, promoters (as overexpression of ANT genes may have toxic effects).

Methods for transfecting mamallian cells are known in the art (see, Kingston et al., "Transfection of DNA into Eukaryotic Cells," Section I of Chapter 9 in: *Short Protocols in Molecular Biology,* 2nd Ed., Asubel et al., eds., John Wiley & Sons, New York, N.Y., 1992, pages 9–3 to 9–16). A control plasmid, such as pCH110 (Pharmacia), may be cotransfected with the ANT expression construct being examined so that levels of ANT can be normalized to a gene product expressed from the control plasmid.

Western analyses of mammalian expression systems are performed essentially as described in the preceding Examples, except that different methods are used to prepare protein preparations from mamallian cells as opposed to bacterial, insect or yeast cells. Such methods of isolating proteins from yeast are known in the art (see, for example, Kingston and Sheen, Unit 9.6A and Brasier, Unit 9.6B of Chapter 9 in: *Short Protocols in Molecular Biology,* 2nd Ed., Asubel et al., eds., John Wiley & Sons, New York, N.Y., 1992, pages 9–17 to 9–23). Preferred expression cassettes, consisting essentially of a promoter and associated regulatory sequences operably linked to an ANT gene of interest, are identified by the ability of cells transiently transformed with a vector comprising a given ANT expression cassette to express high levels of ANT protein when induced to do so; these expression cassettes are incorporated into viral expression vectors.

B. Viral Expression

Nucleic acids, preferably DNA, comprising preferred expression cassettes are isolated from the transient expression constructs in which they were prepared, characterized and optimized (see preceding section). A preferred method of isolating such expression cassettes is by amplification by PCR, although other methods (e.g., digestion with appropriate restriction enzymes) can be used. Preferred expression cassettes are introduced into viral expression vectors, preferably retroviral expression vectors, in the following manner.

A DNA molecule comprising a preferred expression cassette is introduced into a retroviral transfer vector by ligation (see preceding Examples). Two types of retroviral transfer vectors are known in the art: replication-incompetent and replication-competent. Replication-incompetent vectors lack viral genes necessary to produce infectious particles but retain cis-acting viral sequences necessary for viral transmission. Such cis-acting sequences include the ψ packaging sequence, signals for reverse transcription and integration, and viral promoter, enhancer, polyadenylation and other regulatory sequences. Replication-competent vectors retain all these elements as well as genes encoding virion structural proteins (typically, those encoded by genes designated gag, pol and env) and can thus form infectious particles in a variety of cell lines. In contrast, these functions are supplied in trans to replication-incompetent vectors in a packaging cell line, i.e, a cell line that produces mRNAs encoding gag, pol and env genes but lacking the ψ packaging sequence. See, generally, Cepko, 0.15 Unit 9.10 of Chapter 9 in: *Short Protocols in Molecular Biology* 2nd Ed., Asubel et al., eds., John Wiley & Sons, New York, N.Y., 1992, pages 9–30 to 9–35.

A retroviral construct comprising an ANT expression cassette produces RNA molecules comprising the cassette sequences and the ψ packaging sequence. These RNA molecules correspond to viral genomes that are encapsidated by viral structural proteins in an appropriate cell line (by "appropriate" it is meant that, for example, a packaging cell line must be used for constructs based on replication-incompetent retroviral vectors). Infectious viral particles are then produced, and released into the culture supernatant, by budding from the cellular membrane. The infectious particles, which comprise a viral RNA genome that includes the ANT expression cassette, are prepared and concentrated according to known methods. It may be desirable to monitor undesirable helper virus, i.e., viral particles which do not comprise an ANT expression cassette. See, generally, Cepko, Units 9.11, 9.12 and 9.13 of Chapter 9 in: *Short Protocols in Molecular Biology,* 2nd Ed., Asubel et al., eds., John Wiley & Sons, New York, N.Y., 1992, pages 9–36 to 9–45.

Viral particles comprising an ANT expression cassette are used to infect in vitro (e.g., cultured cells) or in vivo (e.g., cells of a rodent, or of an avian species, which are part of a whole animal). Tissue explants or cultured embryos may also be infected according to methods known in the art. See, generally, Cepko, Unit 9.14 of Chapter 9 in: *Short Protocols in Molecular Biology,* 2nd Ed., Asubel et al., eds., John Wiley & Sons, New York, N.Y., 1992, pages 9–45 to 9–48. Regardless of the type of cell used, production of ANT protein is directed by the recombinant viral genome.

In a preferred embodiment, recombinantly produced ANT proteins are inserted into the cell membrane of cultured cells. Because the retroviral expression construct produces viral particles by budding of the cell membrane, the resultant viral particles delivered to the culture supernatant have ANT protein incorporated into their capsules, preferably on the surface of the particles. Such ANT-displaying viral particles are expected to provide a stable format for ANT proteins and to thus be useful in assays using ANT proteins, either directly or as a source material from which ANT can be further purified. If it is desired to minimize the amount of ANT protein inserted into mitochondrial membranes, $p^0$ cells, which have been treated in such a manner as to be nearly or completely devoid of mitochondria, are used as host cells.

C. ANT Antisense Constructs

Antisense versions of the preceding transient and viral ANT expression constructs are prepared by exchanging the antisense (non-encoding) strand for a sense (ANT protein encoding) strand in a construct. Such ANT antisense constructs are useful as research reagents, i.e., to reduce levels of expression of one or more isoforms in a cell transformed or infected with such a construct in order to determine the effects of such treatment on cellular physiology. ANT antisense constructs are also useful as gene therapy agents that interfere with the translation of one or more isoforms of ANT.

Example 6

Synthesis and Properties of Representative ATR Derivatives

A number of atractyloside (ATR) derivatives were prepared for use as ligands for adenine nucleotide translocators (ANTs) in the context of high-throughput screening assays. These compounds bind with high affinity (i.e., in the nM range) to ANT and are thus useful for screening libraries of chemical compounds for molecules having high specificity for ANT (regardless of isoform). The structure of ATR is set forth below as compound (1). Compounds (3) and (4) represent novel fluorescent derivatives of ATR, while compound (2) is an ATR derivative which permits introduction of the $^{125}I$ under mild conditions.

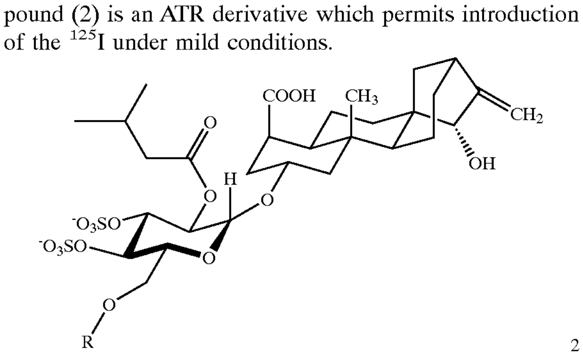

2

1

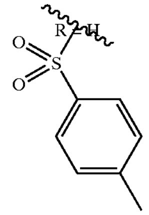

-continued

3

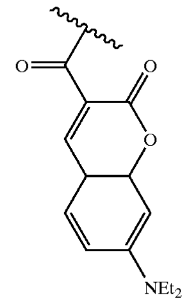

4

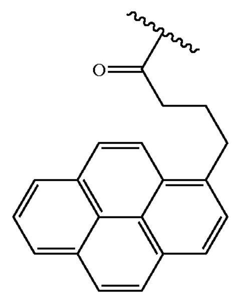

Purification

Compounds 2, 3 and 4 were purified by silica gel chromatography using $CH_2Cl_2$/MeOH/AcOH (75:25:1) as the eluting solution. Detection was achieved by staining with a 0.5% solution of vanillin in $H_3PO_4H_2O$ (1/1). Further purification was accomplished by reversed-phase HPLC using a Microsorb C8 column (250×10 mm). The column was eluted at a flow rate of 2.0 mL/min with a linear gradient of methanol/acetic acid/1M ammonium acetate 98:1:1 ("Solvent B") and $H_2O$/acetic acid/1M ammonium acetate aqueous solution 98:1:1 ("Solvent A"). The effluent was monitored for absorbance at 254 nm. Compound-containing fractions were pooled, evaporated, and repeatedly co-evaporated with added methanol (3×5 mL).

Synthesis of Compound 2

Atractyloside 1 (0.10 mmol) was dried by repeated evaporation of added pyridine (3×5 mL) and the resulting gummy residue dissolved in pyridine (5 mL). To the resulting solution, 0.20 mmol of toluenesulfonyl chloride was added. The reaction mixture was stirred at ambient temperature for 1.5 h. Then, another portion of toluenesulfonyl chloride (0.20 mmol) was added and the reaction left stirring an additional 1.5 h. 1 mL of methanol was added to the reaction mixture which was then stirred for 0.5 h, after which solvents were removed by evaporation. Residual pyridine was removed by evaporation of additional methanol (5×10 mL). Silica gel chromatography followed by reversed-phase HPLC using a linear gradient of 50–80% of solvent B in solvent A for 30 min. resulted in the compound 2 eluting at 68% solvent B. Yield: 4.3 mg, 4.9%. ESI-MS (M−H) found: 879, calc.: 879.

Synthesis of Compounds 3 and 4

7-Diethylamino-2-oxo-2H-chromene-3-carboxylic acid or 0.20 mmol of 1-pyrenebutyric acid and 0.60 mmol of 1,1'-carbonyldiimidazole in 1 mL of dimethylformamide were allowed to react for 15 min. To the activated carboxylic acid was added a solution of atractyloside 1 in 120 (4 mL) and the resulting reaction mixture was stirred at ambient temperature for 16 h. Evaporation left a gummy residue which was purified by silica gel chromatography followed by reversed-phase HPLC. Using a linear gradient of 10–80% of solvent B in solvent A for 50 min (for compound 3) or 50–100% of solvent B in solvent A for 50 min (for compound 4) resulted in compound 3 eluting at 75% B and compound 4 eluting at 82% B. Yields: compound 3, 3.1 mg, 8.0%; compound 4, 1.3 mg, 3.6%. ESI-MS (M–H) compound 3 found: 968, calc.: 968; compound 4 found: 995, calc.: 995.

Properties of Representative ATR Derivatives

As summarized in Table 1 below, compounds 3 and 4 were found to be more advantageous in terms of fluorescence characteristics and sensitivity compared to the existing ATR derivatives Naphthoyl-ATR and MANT-ATR as reported by Boulay et al., *Analytical Biochemistry* 128:323–330,1983; Roux et al., *Analytical Biochemistry* 234:31–37,1996; and Lauquin et al., *FEBS Letters* 67:306–311,1976.

TABLE 1

| ATR Derivative | Excitation (nm) | Emission (nm) | Extinction Coefficient ($M^{-1}$) (Predicted) |
|---|---|---|---|
| Naphthoyl-ATR | 300 | 405 | 6,200 |
| MANT-ATR | 350 | 460 | 5,800 |
| Compound 4 | 341 | 391 | 17,420 |
| Compound 3 | 417 | 470 | 46,400 |

Example 7

Synthesis of Representative ATR Derivative

The further representative ATR derivative, compound 5, was prepared by the procedure set forth below.

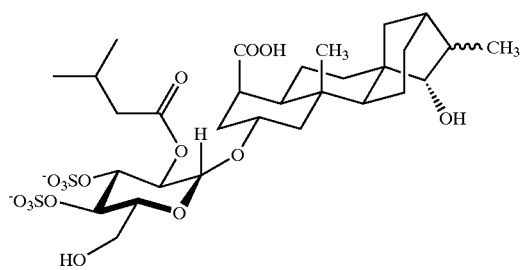

Synthesis of Compound 5

Dipotassium atractylate (0.10 mmol) was dissolved in 50% aq. ethanol (5 mL) and palladium on charcoal (10%, 17 mg) was added to the reaction mixture. After flushing the system with hydrogen, the reaction mixture was stirred under an atmosphere of hydrogen gas for 3 h. Removal of catalyst by filtration through Celite, washing with 50% aq. ethanol (10 mL), and evaporation of solvents afforded a white solid. Yield after thorough drying under high vacuum, 78.3 mg (97.3%). ESI-MS (M–2H+K) found: 765, calc.: 765. $^1$H-NMR analysis confirmed the absence of alkenic protons: DMSO-$d_6$) δ 0.88(d, 3H), 0.89(d, 3H), 1.02(d, 3H).

Example 8

Synthesis of Representative Iodinated ATR Derivative

Compound 2 of Example 6 may be used as intermediate for conjugation of variety of chemical moieties to yield further ATR derivatives. In this example, compound 2 is employed to introduce $^{125}$I under mild conditions to yield the following compound 6.

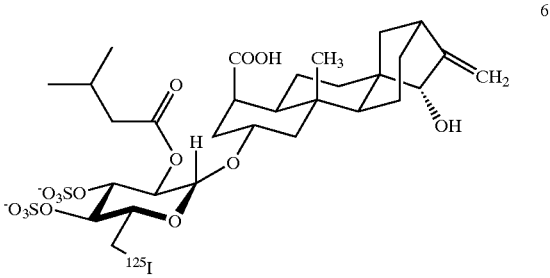

Synthesis of Compound 6

Five μl of 0.2 M sodium phosphate (pH 5) was combined with 21 ul of Na$^{125}$I (9.25 mCi) in its shipping container (specific activity, 2100 Ci/mmol; Amersham, Piscataway, N.J.). Ten ul (200 ug, 212 nmol) of compound 2 of Example 1 was added to the mixture. The pH was checked with litmus paper to confirm that it did not rise above pH 5. The mixture was allowed to stand at ambient temperature overnight (17.5 hours) to yield radiolabelled compound 6. (Non-radioactive iodinated ATR derivative, for use as a "cold" competitor in binding studies, may be prepared in the same manner using unlabeled iodine) The iodinated derivative was purified over a C18 analytical column (4×6×250 mm) (Phenomenex, Torrance, Calif.) using a 25%–55% acetonitrile gradient in running buffer (1% triethylammonium acetate, pH 4.5). A flow rate of 1 ml/min was used to run the gradient over 30 min. The desired product eluted at 25 min. ESI-MS: 835 (M-H), 707 (m$^{-2}$H-I).

Example 9

Synthesis of Representative ATR Derivatives

Activation of carboxylic acids with carbonyl diimidazole and their reaction with ATR has been the method of choice for synthesis of various 6'-O-acyl derivatives. The relatively low reactivity of the 6'-hydroxyl of ATR and the presence of an allylic secondary hydroxyl in the aglycon as well as the sulfated glucose moiety, are all factors that have a negative impact on the efficiencies of these acylation reactions. Hence, yields are generally poor and the approach requires a large excess of acylating reagents.

Two strategies for introduction of an amine functionality in the ATR system are described below that permit synthesis of a broader range of ATR derivatives. In the first strategy, as depicted by Scheme 1, displacement of the primary tosylate from compound 2 (Example 1) with azide followed by reduction yields the corresponding 6'-amine (compound 7). Alternatively, the amine group can be introduced as part of a spacer, which permits introduction of more sterically demanding functional moieties. Thus, reacting the 6'-O-succinoyl derivative (compound 8; see Brandolin et al., 1974 *FEBS Lett.* 46:149.) with a monoprotected diamine followed by deprotection affords compound 9 as illustrated by Reaction Scheme 2.

Reaction Scheme 1

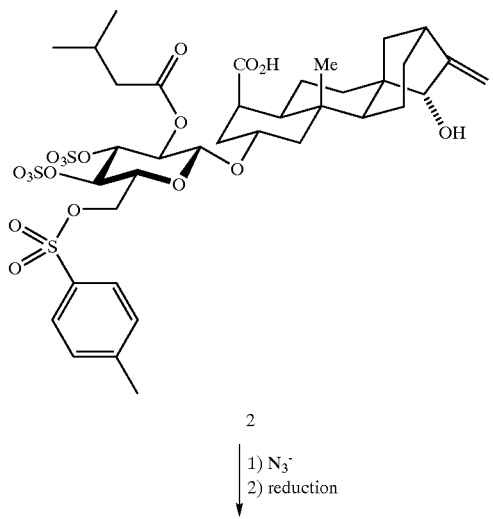

Reaction Scheme 2

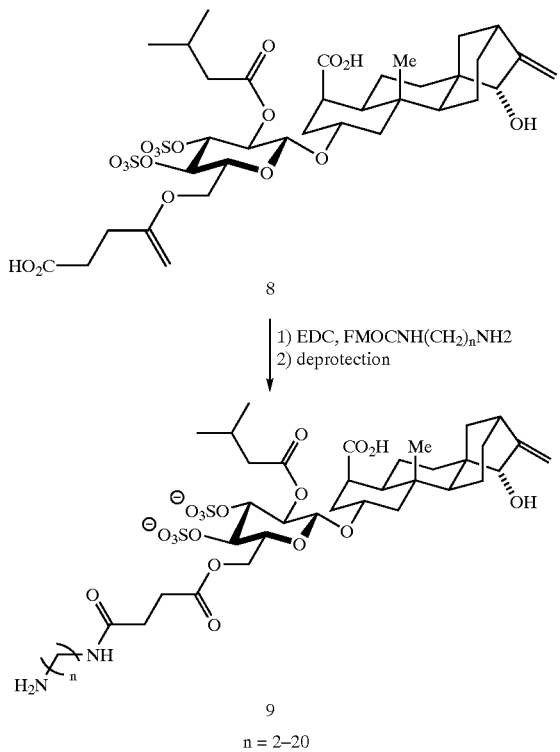

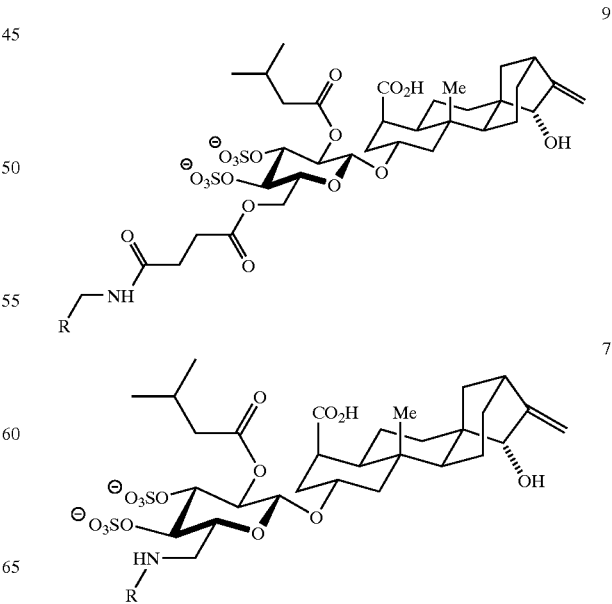

The amine-containing ATR derivatives 7 and 9 may then be reacted with a variety of fluorophors and haptens bearing reactive isothiocyanate, N-hydroxysuccinimide ester and anhydride functionalities to yield stable ATR-derivatives having thiourea and amide linkages. Representative ATR derivatives that were prepared include ATR-lanthanide chelating agents (compounds 10, 11, 12, 13, 20 and 21) that have utility for time-resolved fluorescence detection of these compounds complexed to $Eu^{3+}$. In addition, ATR was conjugated to cyanine (compounds 14 and 15) and fluorescein analogues (compounds 16 and 17) that are detectable by fluorescence with extremely high sensitivities. Coupling of biotin-NHS ester with the ATR derivatives of compounds 7 and 9 provided ATR-biotin conjugates (compounds 18 and 19) that can be detected with commercially available enzyme-avidin conjugates using colorimetric, fluorescent or chemiluminescent techniques.

More specifically, a solution of compound 2 in DMF was treated with azide ion for 8 hours at 80° C. to give the 6'-azido-ATR, that was purified by silica gel chromatography using a $CH_2Cl_2/CH_3OH$ solvent system supplemented with 1% acetic acid. Staudinger-reduction using 1.5 equivalents of triphenylphosphine in a $THF/H_2O$ mixture for 4 hours at RT afforded the amine of compound 7, that was isolated after silica gel chromatographic purification.

To accommodate more sterically demanding functional moieties, 6'-O-succinoyl-ATR may be condensed with commercially available monoprotected diamines (Calbiochem-Novabiochem Corp, San Diego, Calif.) to produce ATR-mono-protected amine derivatives. Thus, EDC-mediated coupling of 6'-O-succinoyl-ATR in DMF with 1.1 equivalents of mono-protected FMOC diamines yield the amide that was deprotected using piperidine or 1,8-diazabicyclo [5.4.0]undec-7-ene (DBU) in acetonitrile to furnish the ATR derivative of compound 9. The amines were purified by silca gel chromatography as described above.

The ATR-amine derivatives of compounds 7 and 9 were coupled to a variety of fluorophors, chelates and haptens that contained amine-reactive functionalities, such as isothiocyanates, anhydrides and NHS esters in aqueous DMF to generate the ATR derivatives of compounds 10 through 19: These compounds were purified by a combination of silica gel chromatography and preparative reverse phase chromatography on a C-8 column using $CH_3OH/H_2O$ gradient containing 0.1–1% acetic acid.

10
R = 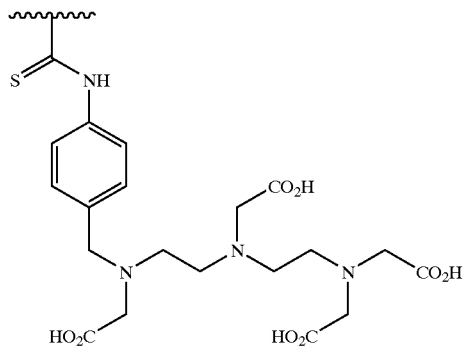
11
R = 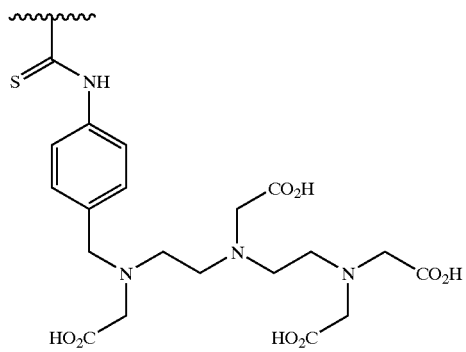
12
R = 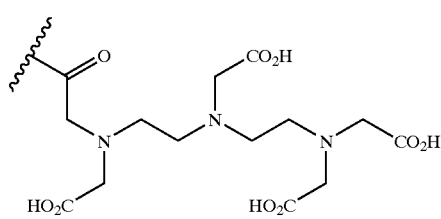
13
R = 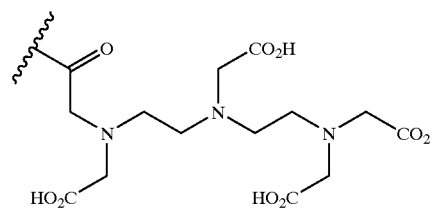
14
R = 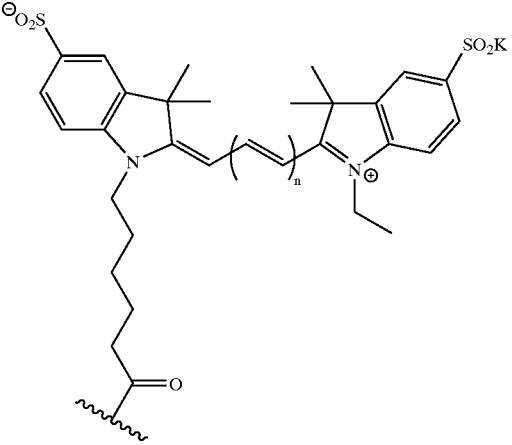
15
R = 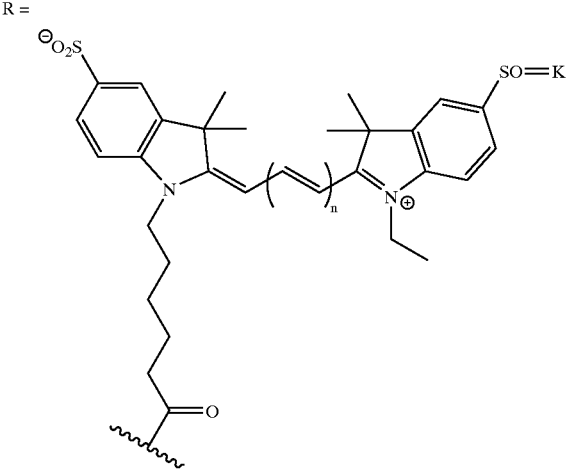
16
R = 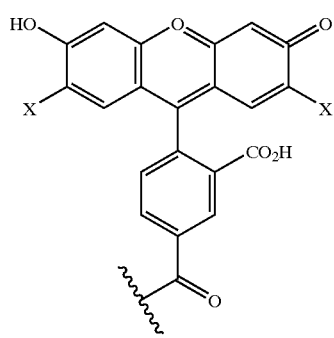
X = H, F, C

R =

17

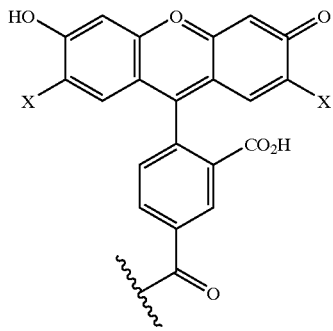

X = H, F, C

R =

18

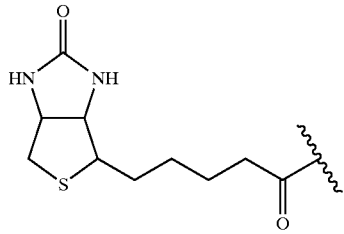

R =

19

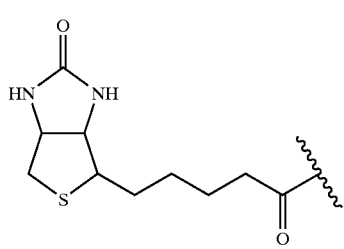

R =

20

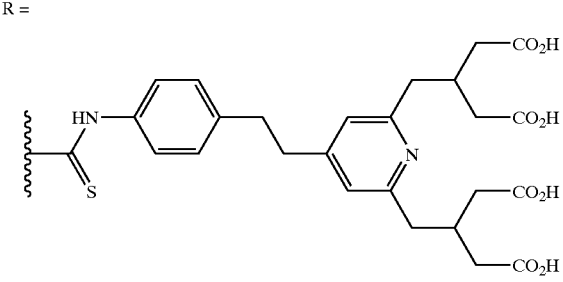

R =

21

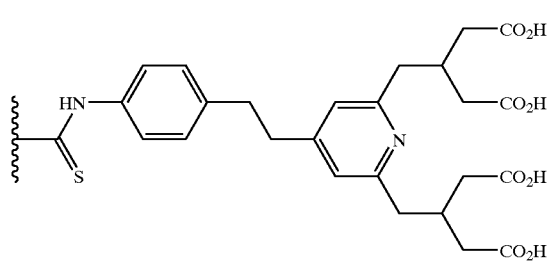

Example 10

Synthesis of Representative ATR Derivatives and Intermediates Therefor

General Procedure for Coupling Atractyloside or Dihydroatractyloside to Organic Acids

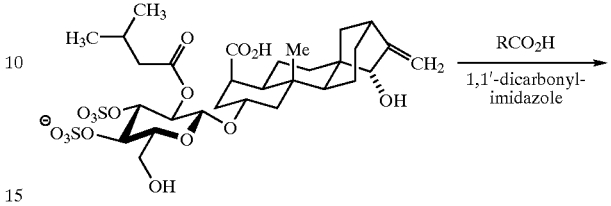

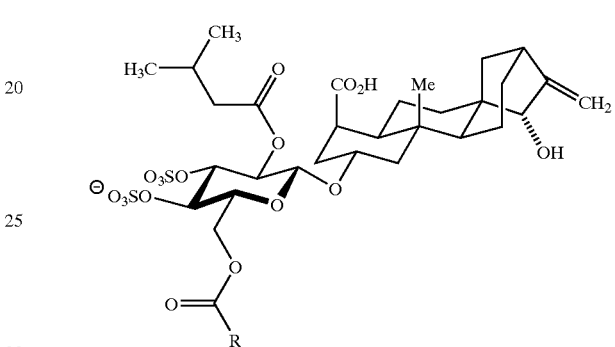

In Ddihydro-atractyloside, the exocyclic bond is reduced

Carboxylic acid (200 μmol) and 1,1'-carbonyldiimidazole (700 μmol) were dissolved in DMF (2 mL) and stirred for 15 min. To the activated acid, a solution of atractyloside (ATR) (100 μmol, 85 mg) or dihydroatractyloside (100 μmol) in DMF:$H_2O$ (1:2, 6 mL) was added (in 1 mL portions over ca 30 sec). The reaction mixture was stirred at room temperature for 60 nm, after which solvents were removed by rotary evaporation on a water bath in which the temperature was kept below 40° C. The residue was stripped of traces of DMF by repeated evaporation of added EtOH:$H_2O$ (1:1, 3×20 mL). The residue was then taken up in MeOH: $H_2O$ (1:1, 10 mL), sonicated if necessary, and filtered through a 0.45 μm filter. Evaporation, re-dissolution in ~1.3 mL buffer, and purification by reverse phase HPLC FURNISHED the desired 6'-O-acyl-ATR in yields ranging from 5–15%.

Reverse Phase HPLC Conditions for Purification of Atractyloside Derivatives

Purification by reverse phase HPLC (RP-HPLC) was performed in a 10×250 mm C-8 column, using a gradient of MeOH:AcOH: 1M $NH_4OAc$ (buffer B, 98:1:1) in $H_2O$:AcOH:1M $NH_4OAc$ (buffer A, 98:1:1). Typically, a gradient of B in A from 50–80% over 30 min was employed. For more lipophilic derivatives, the gradient was from 60–90% or 70–100% B over the same time period.

Synthesis of Dihydroatractyloside

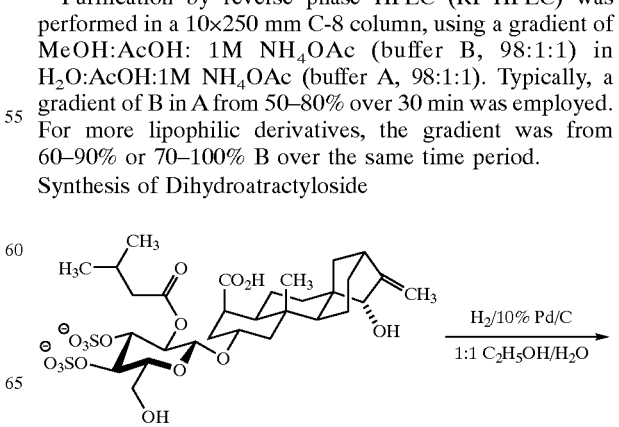

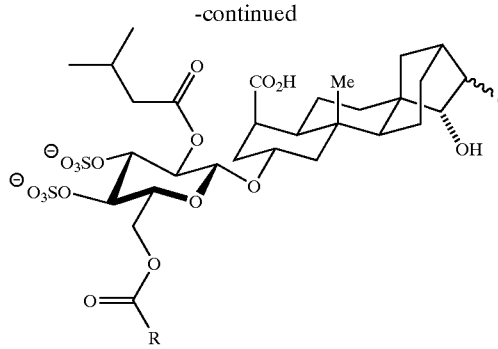

Atractyloside, dipotassium salt (254 mg, 0.3 mmole) in 15 ml of $EtOH/H_2O$ (1:1) was hydrogenated under atmospheric pressure for 3 hours using 51 mg of activated palladium/carbon (10%) as catalyst. The catalyst was removed by filtration through celite and the celite bed was washed with 15 ml of $EtOH/H_2O$. The filtrates were concentrated by rotary evaporation, followed by drying under high vacuum overnight to provide the product as white solid (236 mg), that was pure by NMR.

6'-Tosyl-Atractyloside

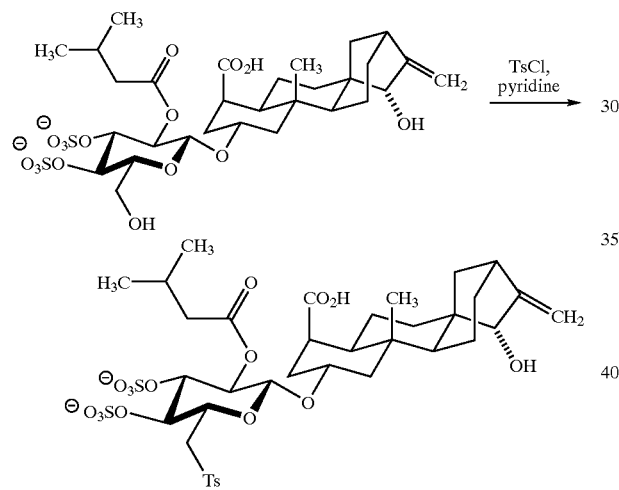

Atractyloside.$3H_2O$ (255 mg. 0.3 mmole) was dried by co-evaporation with dry pyridine (3×5 ml) and then was kept under high vacuum for 16 hrs. The dried atractyloside was dissolved in 15 ml of dry pyridine and 114 mg of tosyl chloride (0.6 mmole) was added. The reaction was stirred for 2 hrs at 23° C. and then an additional 114 mg of tosyl chloride was added and the reaction was allowed to continue for an additional 1.5 hrs. Methanol (1 ml) was added to the reaction mixture to scavenge excess tosyl chloride and the mixture was stirred for several minutes. The mixture was evaporated to dryness, and residual pyridine was removed by evaporation of added methanol (2×30 ml). The crude product was partially purified by silica gel flash chromatography ($CH_2Cl_2$/MeOH, 3:1 with 1% AcOH). The product containing fractions were dissolved in 3 ml of $H_2O$:MeOH:1M $NH_4OAc$:HOAc (49:49:1:1) and purified by RP-HPLC using a 50%–80% gradient of MeOH:AcOH:1M $NH_4OAc$ (buffer B, 98:1:1) in $H_2O$:AcOH:1M $NH_4OAc$ (buffer A, 98:1:1). Product containing fractions were pooled, evaporated, and subjected to additional co-evaporation of 3×10 ml of MeOH. Tosyl-atractyloside was obtained as a glassy material weighing 60 mg.

General Procedure for Lactoperoxidase-Catalyzed Iodination of 4-Hydroxyphenyl Derivatives

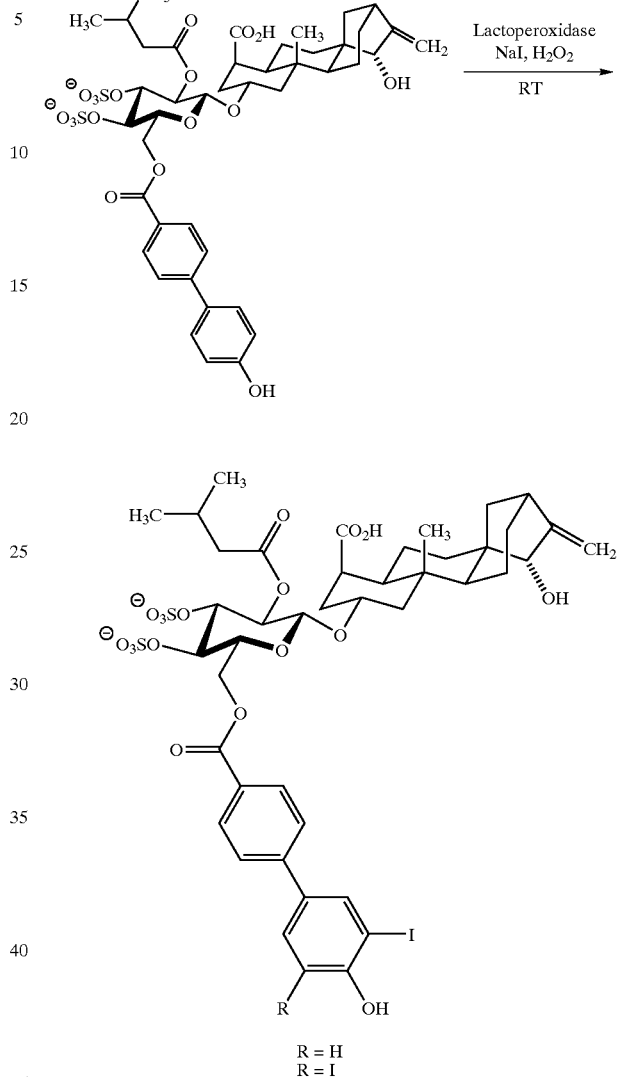

To a solution of 4'-hydroxy-biphenyl-4-carboxylic acid atractylosid-6'-yl ester (1.0 mg, 1.0 mmol) in $H_2O$ (120 μL) were added aqueous solutions of lactoperoxidase (50 μL, 200 μL/mL), NaI (10 μL, 100 mM) and $H_2O_2$ (20 μL, 100 mM). The reaction was left at room temperature for 1 h after which it was frozen at −20° C. The next day (~20 hours later) the reaction mixture was thawed and subjected to RP-HPLC. Three major peaks were eluted and electrospray ionization-mass spectrometic (ESI-MS) analysis confirmed their identity as unreacted starting material, and monoiodinated, and diiodinated atractyloside derivatives.

These conditions can be modified to drive the reaction completely to the mono and di-iodinated forms with additional aliquots of NaI and/or enzyme.

General for Synthesis of Iodophenols

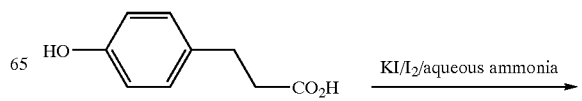

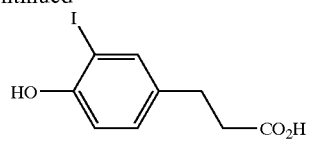

The iodination procedure described in Acta Chem, Scand. 12, 188 (1958) was used for mono-iodination of 3-(4-hydroxyphenyl)propionic acid, 4'-hydroxy-4-biphenylcarboxylic acid and 4-hydroxybenzoic acid. This method is also applicable for the mono-iodination of 3-(4-methoxyphenyl)-propionic acid and di-iodination of 3-(3-iodo-4-hydroxyphenyl)propionic acid, Thus a solution of KI (1.99 gm, 12 mmole) and iodine (1.22 gm, 4.8 mmole) in 20 ml of $H_2O$ was added in a dropwise fashion to a solution of 3-(4-hydroxyphenyl)propionic acid (0.83 gm, 5 mmole) in 100 ml of concentrated aqueous ammonia solution over 20 min. The reaction mixture was stirred for an additional 40 min and then subjected to vacuum to remove the ammonia. The mixture was dried further by rotary evaporation to afford an oily residue. The crude material was partitioned between 2M HCl (50 ml) and ether (2×50 ml) and the ether layers were combined and concentrated to give a yellowish solid residue. Flash silica gel chromatography using 95:5 $CH_2Cl_2$/MeOH as eluant, concentration of product containing fractions and recrystallization in 1:1 benzene hexane afforded 790 mg of 3-iodo-4-hydroxyphenylpropionic acid.

3-(3,5-Diiodo-4-hydroxyphenyl)propionic acid was prepared in similar fashion using 5.2 equivalents of KI and 2.1 equivalents of 12. Following crystallization from toluene, the di-iodo derivative was obtained in 77% yield.

5-iodo-6-hydroxy-2-naphthoic acid

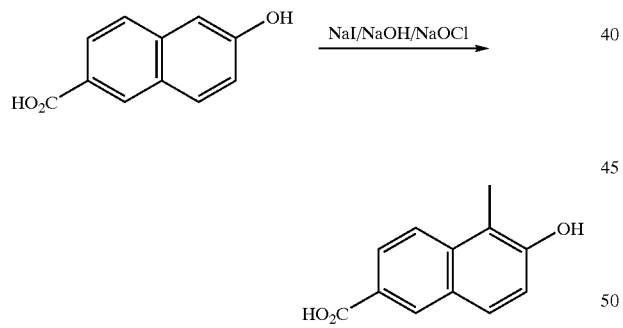

Mono-iodination of 6-hydroxy-2-naphthoic acid and 4-hydroxybenzoic acid was carried out following the procedure of Edgar and Falling (J. Org. Chem. 55, 5287, 1990). Thus, 0.75 gm of (4.34 mmol) was dissolved in 19 ml of MeOH and 1.04 gm of NaI (and 0.27 gm of NaOH was added. The solution was cooled to 0°C and aqueous NaOCl (4% solution, 12.9 ml) was added dropwise over 75 min. The resulting mixture was stirred for 1 hr at 0° C. and then treated with 7 ml of 10% aqueous sodium metabisulfite. The mixture was adjusted to pH 7 using 5% HCl and extracted with 40 ml of ether. The organic layer was washed with brine and dried over $MgSO_4$. The solution was concentrated to an off-white solid, that was recrystallized from toluene/$CH_3OH$ to provide 0.42 gm of 5-iodo-6-hydroxy-2-naphthoic acid.

Reaction of 6'-Tostylatractyloside with 1,2-ethylenediamine

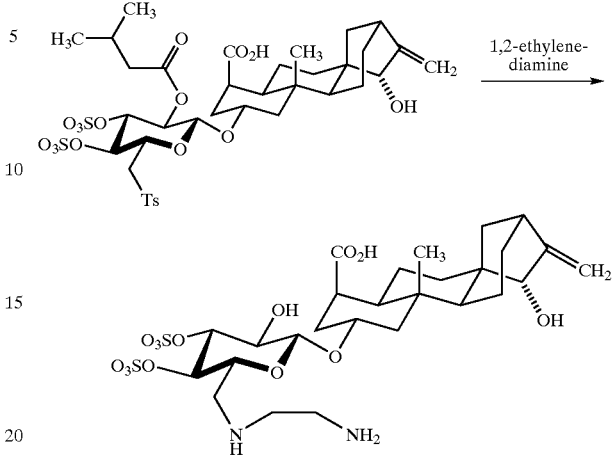

6'-Tosyl-Atractyloside (25 mg) was dissolved in 2 ml of 1,2-ethylenediamine and the mixture was stirred at 23° C. overnight. The 1,2-ethylenediamine was removed in vacuo, the residue was dissolved in MeOH/$H_2O$ (2:1) and 10.6 mg of the product was isolated in by RP-HPLC using the conditions described above. Proton nmr and mass spectra indicate the loss of the isovaleryl group.

Reaction of N-(6-Deoxy-apo-atractylosyl)-ethanediamine with Bolton Hunter Reagent N-(6-Deoxy-apo-atractylosyl)-ethanediamine (10.6 mg) in 2.75 ml of DMF/DMSO (8:3) was reacted with 60 mg of 4-hydroxyphenylpropionyl-N-hydroxysuccinimidyl ester (Bolton Hunter reagent) at 23° C. for 16 hrs. The solution was diluted with water and purified by RP-HPLC to afford 9.1 mg of the desired compound.

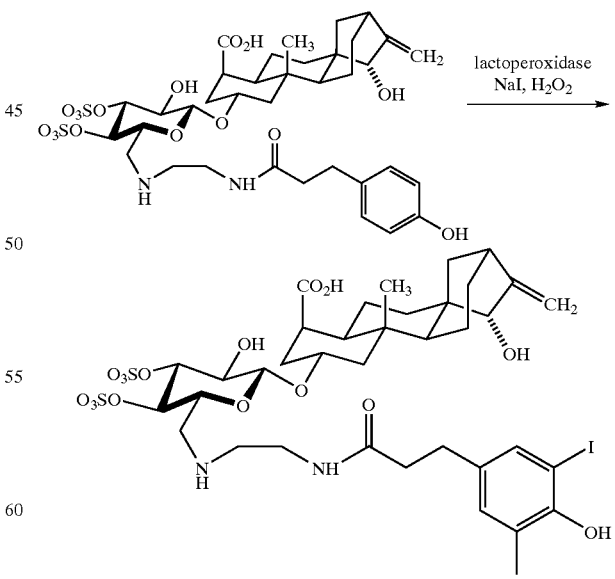

Lactoperoxidase catalyzed iodination of the compound leads to a quantitative conversion to the di-iodo-apo-atractyloside derivative.

Reaction of Atractyloside with Succinic Anhydride

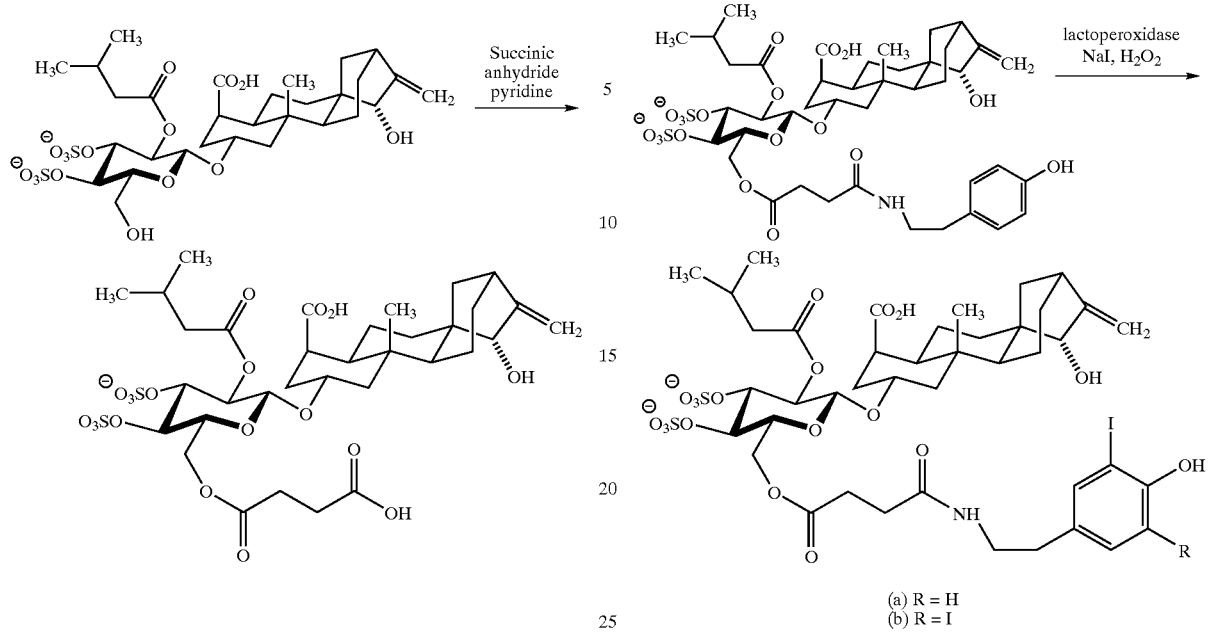

Atractyloside.3H$_2$O (255 mg. 0.3 mmole) was dried by co-evaporation with dry pyridine (3×5 ml) and then was kept under high vacuum for 16 hrs. The dried atractyloside was dissolved in 6 ml of dry pyridine and 60 mg of succinic anhydride (0.6 mmole) was added. The mixture was kept at 80° C. for 30 min, another 60 mg (0.6 mmole) of succinic anhydride was added and the reaction mixture was stirred for an additional 3 hrs. The pyridine was removed in vacuo, and the residue was triturated with 10 ml of MeOH. The 6'-O-succinyl-ATR derivative was collected by filtration as a white solid, washed with MeOH and dried overnight over P$_2$O$_5$.

Reaction of 6'-O-succinylatractyloside with tyramine and iodination

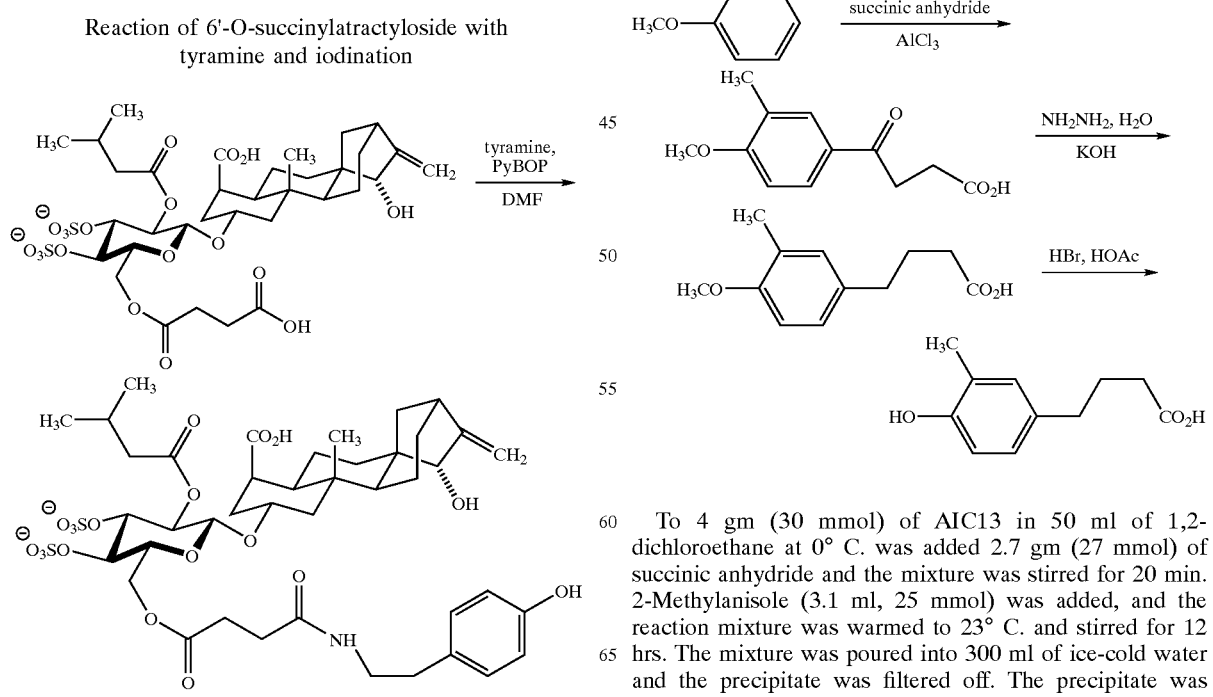

(a) R = H
(b) R = I

6'-O-Succinylatractyloside (85 mg) was dissolved in 2 ml of DMF and 28 mg of tyramine and 100 mg of PyBOP was added. The mixture was stirred at 23° C. for 16 hrs. The crude mixture was subjected to RP-HPLC and the desired amide was isolated in 19.7 mg. Lactoperoxidase catalyzed Iodination of the product using the standard conditions described above provides the mono and the di-iodinated products.

Synthesis of 4-(4-Hydroxy-3-Methyl)-Butyric Acid

To 4 gm (30 mmol) of AlCl3 in 50 ml of 1,2-dichloroethane at 0° C. was added 2.7 gm (27 mmol) of succinic anhydride and the mixture was stirred for 20 min. 2-Methylanisole (3.1 ml, 25 mmol) was added, and the reaction mixture was warmed to 23° C. and stirred for 12 hrs. The mixture was poured into 300 ml of ice-cold water and the precipitate was filtered off. The precipitate was washed with 2×300 ml of water to afford a white solid. The solid material was dried under vacuum to afford 3.51 gm of product that was used in the next reaction.

3-(4-Methoxy-3-methylbenzoyl)propionic acid (4.4 gm, 20 mmol) and 4.49 gm of KOH pellets (80 mmol) were dissolved in 30 ml of ethylene glycol and 3.88 ml of hydrazine hydrate (80 mmol) was added to the stirred solution in four portions. The resulting reaction mixture was heated at 155° C. for 24 hrs in an oil bath. After cooling, the reaction mixture was taken up in 100 ml of benzene and washed with 10% aqueous citric acid. The organic layer was washed with another portion of citric acid, dried over anhydrous sodium sulfate, and concentrated in vacuo to afford an oily residue that crystallized upon standing. The material was triturated with hot hexane and the solvent was evaporated off to afford 3.55 gm of a crystalline solid that was homogeneous by silica gel tic using hexane/ethyl acetate (8:2) as eluting solvent.

4-(4-Methoxy-3-methylphenyl)butyric acid (3.12 gm) was heated in 120 ml of a 1:1 mixture of 48% aqueous HBr/acetic acid at 155° C. for 24 hrs. The reaction mixture was cooled to room temperature and was extracted with 200 ml of benzene/ether (1:1). The organic layer was dried over anhydrous magnesium sulfate and concentrated to afford a light brown solid residue. The reaction products were separated by silica gel flash chromatography using hexane/ethyl acetate (3:1) as eluting solvent to provide 0.86 mg of 4-(4-hydroxy-3-methyl)-butyric acid as a light yellow solid.

Representative Synthesis of Atractyloside Derivatives

To a solution of 3-(4-hydroxyphenyl)propionic acid (HPP) (0.498 g, 3.0 mmole) in 10 ml of anhydrous DMF was added carbonyldiimidazole (0.486 g, 3.0 mmole). The mixture was stirred at room temperature for 30 minutes and added in portions (2 ml/hour) to a solution of atractyloside (ATR) (0.086 g, 0.1 mmole) in 1 ml of anhydrous DMF. The reaction mixture was stirred at room temperature overnight and quenched with 1 ml of water. The solvent was evaporated under vacuum and the residue was dissolved in ethyl acetate (75 ml) and water (50 ml). The aqueous layer is separated, extracted with ethyl acetate (3×75 ml) and concentrated under vacuum. The residue was dissolved in 1.5 ml of methanol/water(1/1), filtered through a 0.2 mm filter and purified using HPLC with a preparative C-8 column (microsorb, 10×250 mm) using a linear gradient elution of 30%–60% solvent B with a flow rate of 2.0 ml/min (solvent A: H2O/HOAc/NH4Oac (1.0M, aq.): {1000/1/1}; solvent B: CH3OH/HOAc/NH4OAc (1.0M, aq.): {1000/1/1}). The title compound (compound 36 of Example 11 below) was obtained as a white film (6.2 mg).

Example 11

Further Representative ATR Derivatives

Following the procedures set forth in Example 10, the following ATR derivatives were prepared.

| Cpd | R | MS | NMR |
|---|---|---|---|
| Atractyloside Derivatives | | | |

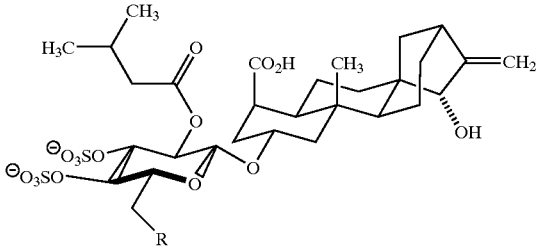

| 22 | 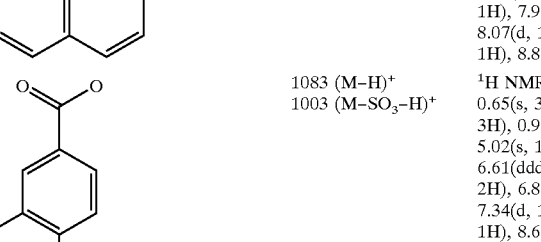 | 879.3 (M–H)+<br>799.3 (M–SO3–H)+ | 1H NMR (CD3OD) δ 0.63(s, 3H), 0.95(d, 3H), 0.96(d, 3H), 4.94(s, 1H), 5.09(s, 1H), 7.53(m, 2H), 7.60(in, 1H), 7.93(d, 1H), 8.07(d, 1H), 8.26(d, 1H), 8.88(d, 1H) |
| 23 | | 1083 (M–H)+<br>1003 (M–SO3–H)+ | 1H NMR (CD3OD) δ 0.65(s, 3H), 0.95(d, 3H), 0.96(d, 3H), 5.02(s, 1H), 5.13(s, 1H), 6.61(ddd, 2H), 6.69(d, 2H), 6.86(dd, 2H), 7.34(d, 1H), 8.33(dd, 1H), 8.67(s, 1H) |

| Cpd | R | MS | NMR |
|---|---|---|---|
| 24 | 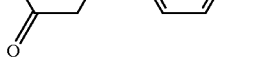 | 999 (M−H)+ | 1H NMR (CD3OD) δ 0.94(s, 3H), 0.95(d, 3H), 0.96(d, 3H), 5.05(s, 1H), 5.15(s, 1H), 6.75(d, 1H), 7.04(dd, 1H), 7.52(d, 1H) |
| 25 | 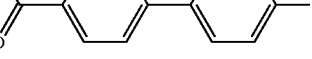 | 921 (M−H)+ 841 (M−SO3−H)+ | 1H NMR (CD3OD) δ 0.75(s, 3H), 0.95(d, 3H), 0.96(d, 3H), 4.97(s, 1H), 5.08(s, 1H), 6.89(d, 2H), 7.52(d, 2H), 7.64(d, 2H), 8.07(d, 2H) |
| 26 |  | 1047 (M−H)+ 967 (M−SO3−H)+ | 1H NMR (CD3OD) δ 0.73(s, 3H), 0.95(d, 3H), 0.96(d, 3H), 4.98(s, 1H), 5.09(s, 1H), 6.93(d, 1H), 7.52(dd, 1H), 7.61(d, 2H), 7.98(d, 1H), 8.08(d, 2H) |
| 27 | 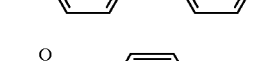 | — | 1H NMR (CD3OD) δ 0.81(s, 3H), 0.95(d, 3H), 0.96(d, 3H), 5.04(s, 1H), 5.15(s, 1H), 6.80(d, 2H), 7.90(d, 2H), 7.64(d, 2H) |
| 28 | 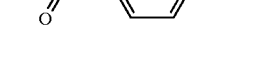 | 1097.1 (M−K)+ 1017.0 (M−SO3−H)+ | 1H NMR (CD3OD) δ 0.83(s, 3H), 0.95(d, 3H), 0.96(d, 3H), 5.03(s, 1H), 5.15(s, 1H), 6.84(d, 1H), 7.88(dd, 1H), 8.33(d, 1H) |
| 29 | 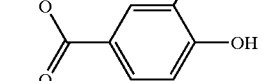 | 1043.2 (M−2H+Na)+ 1021.2 (M−H)+ | 1H NMR (CD3OD) δ 0.66(s, 3H), 0.95(d, 3H), 0.96(d, 3H), 4.93(s, 1H), 5.05(s, 1H), 7.22(d, 1H), 7.87(d, 1H), 8.04(dd, 1H), 8.08(d, 1H), 8.50(d, 1H) |
| 30 | 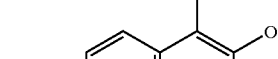 | 944 (M−H)+ 864 (M−SO3−H)+ | 1H NMR (CD3OD) δ 0.97(s, 3H), 0.98(s, 6H), 5.06(s, 1H), 5.17(s, 1H), 5.70(d, 2H), 7.03(d, 2H). |
| 31 |  | 1070 (M−H)+ 990 (M−SO3−H)+ | — |
| 32 | 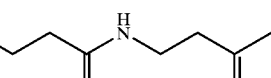 | 1116 (M−SO3−H)+ | — |
| 33 |  | 1125 (M−H)+ 1147 (M−2H+Na)+ | 1H NMR (CD3OD) δ 0.95(s, 3H), 0.96(s, 6H), 5.05(s, 1H), 5.15(s, 1H), 7.58(s, 2H) |

| Cpd | R | MS | NMR |
|---|---|---|---|
| 34 | (structure: 3-methyl-4-hydroxyphenyl propanoate linker) | 923.2 (M−2H+Na)⁺<br>901.3 (M−H)⁺ | — |
| 35 | (structure: 3-methyl-4-hydroxy-5-iodophenyl propanoate linker) | 1049.3 (M−2H+Na)⁺ | — |
| 36 | (structure: 4-hydroxyphenyl propanoate linker) | 873 (M−H)⁺<br>895 (M−2H+Na)⁺ | $^1$H NMR (CD$_3$OD) δ 0.94(s, 3H), 0.96(d, 6H), 5.05(s, 1H), 5.16(s, 1H), |

Dihydroactyloside Derivatives

| Cpd | R | MS | NMR |
|---|---|---|---|
| 37 | (structure: 4-hydroxyphenyl propanoate linker) | 897 (M−2H+Na)⁺<br>875 (N−H)⁺ | $^1$H NMR (CD$_3$OD) δ 0.93(s, 3H), 0.95(d, 3H), 0.96(d, 3H), 1.08(d, 3H), 6.69(d, 2H), 7.02(d, 2H), resonances from alkenic protons absent |
| 38 | (structure: 3-iodo-4-hydroxyphenyl propanoate linker) | 1105 (M−2H+Na)⁺<br>1083 (M−H)⁺ | $^1$H NMR (CD$_3$OD) δ 0.93(s, 3H), 0.95(d, 3H), 0.96(d, 3H), 1.08(d, 3H), 6.74(d, 1H), 7.05(dd, 1H), 7.53(d, 1H), resonances from alkenic protons absent |

Apoactractyloside Derivatives

| Cpd | R | MS | NMR |
|---|---|---|---|
| 39 | (structure: aminoethylamino amide of 4-hydroxyphenyl propanoic acid) | 831 (M−H)⁺ | $^1$H NMR (CD$_3$OD) δ 1.00(s, 3H), 5.07(s, 1H), 5.17(s, 1H), 6.69(d, 2H), 7.03(d, 2H) |

-continued

| Cpd | R | MS | NMR |
|---|---|---|---|
| 40 | [structure: HN-CH2CH2-NH-C(=O)-CH2CH2-(3,5-diiodo-4-hydroxyphenyl)] | 1083 (M−H)+<br>1105 (M−2H+Na)+ | — |

Example 12

Binding Assays Using Recombinant huANT3

A. GST-huANT3 Recombinantly Produced in *E. coli*:

Following arabinose induction, transformed or sham transformed (vector only) *E. coli* were collected by centrifugation at 2000 g for 10 min. The bacterial pellets were resuspended in MSB, to which lysozyme (100 µg/ml) was added. After 20 min at room temperature, the lysates were subjected to one freeze-thaw cycle followed by sonication as described above. The resultant membrane preparation was used for binding assays.

To estimate maximal binding and the extent of overexpression of the huANT3, 25 µg of membrane protein was incubated with varying amounts of [$^{32}$P]ATP (1–500 µM) in binding buffer (120 mM KCl, 10 mM Tris, 1 mM EDTA, pH 7.4) for 2 hr at room temperature. The membranes with bound ATP were sedimented by centrifugation at 5000 g for 5 nm, and washed once with binding buffer. Membrane pellets were then mixed with 5 ml scintillation cocktail and counted. The results are presented in Table 2.

TABLE 2

Saturation Binding of [$^{32}$P]ATP to *E. coli* Membranes

| | cpm bound by: | |
|---|---|---|
| [ATP], uM | Sham Transfomed Cells | huANT3-Producing Cells |
| 0.1 | 109 | 191 |
| 0.5 | 95 | 49 |
| 1.0 | 147 | 325 |
| 5.0 | 123 | N.D. |
| 10 | 214 | 263 |
| 50 | 549 | 2,727 |
| 100 | 718 | 5,772 |
| 500 | 2,140 | 9,715 |

N.D., not determined

The data presented in Table 2 indicate that the affinity of the ATP binding was ~6 µM. ATP binding was completed abolished by the addition of atractyloside (10 µM) to the assay. These results support the contention that the measured ATP binding was predominantly to recombinantly produced ANT3 protein.

Agarose-glutathione beads were incubated with solubilized (using Dnase, Rnase and 0.1% Triton X-110; see Example 1, section D) bacterial lysate (see Example 2), and substituted for the *E. coli* membranes in binding assays. Best results (i.e., more specific binding) were seen when the beads were preincubated with bovine serum albumin (BSA, 0.1%) Specific ATP binding (1,070 cpm) was also observed in this experiment (compare to nonspecific binding of 279 cpm in the presence of 10 mM non-radiolabeled ATP).

B. huANT3 from a Sf9/Baculovirus Expression System

Sf9 cells expressing huANT3 were grown in spinner flasks. The cells were harvested by centrifugation at 2,000 g for 5 min. The cell pellet was resuspended in MSB and subjected to 3 freeze-thaw cycles. Cell membranes and debris were removed by centrifugation at 600 g for 5 min; mitochondria were collected by centrifuging the supernatant at 20,000 g for 15 min. The mitochondrial pellets were suspended in MSB, and used for binding assays as described above. Homologous competition of [$^{32}$P]ATP binding was performed using 25 µg mitochondrial protein per assay.

Figure 7:
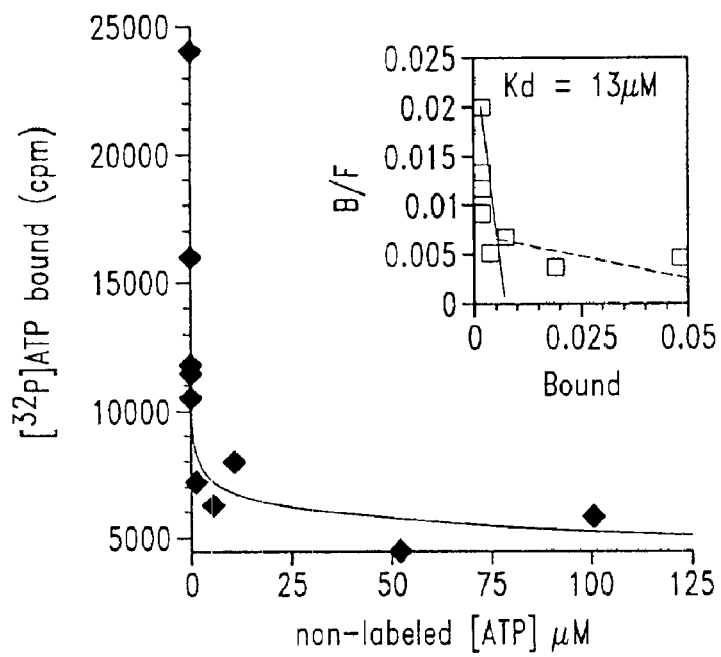
FIG. 7 shows [$^{32}$P]ATP binding to Sf9/huANT3 mitochondria.
Figure 8:
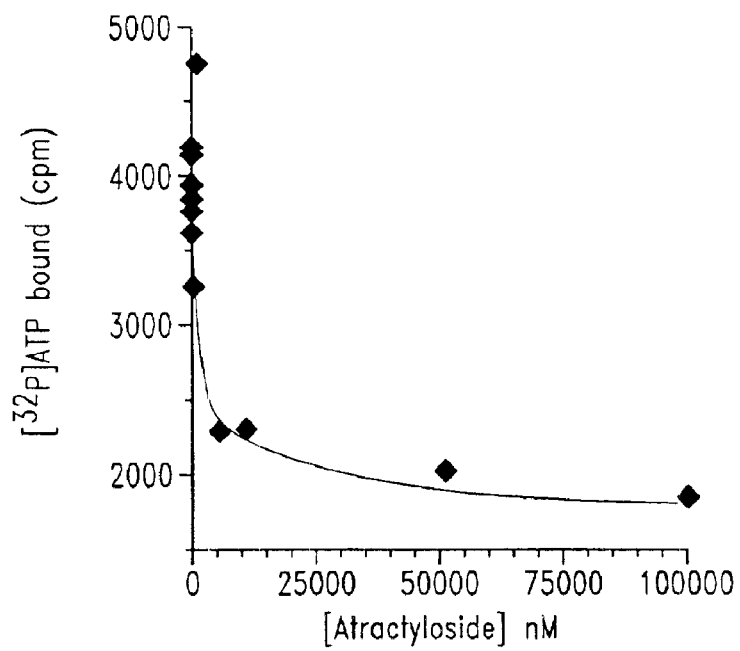
FIG. 8 shows that ATP and atractyloside bind competitively to Sf9/huANT3 mitochondria.
Figure 9:
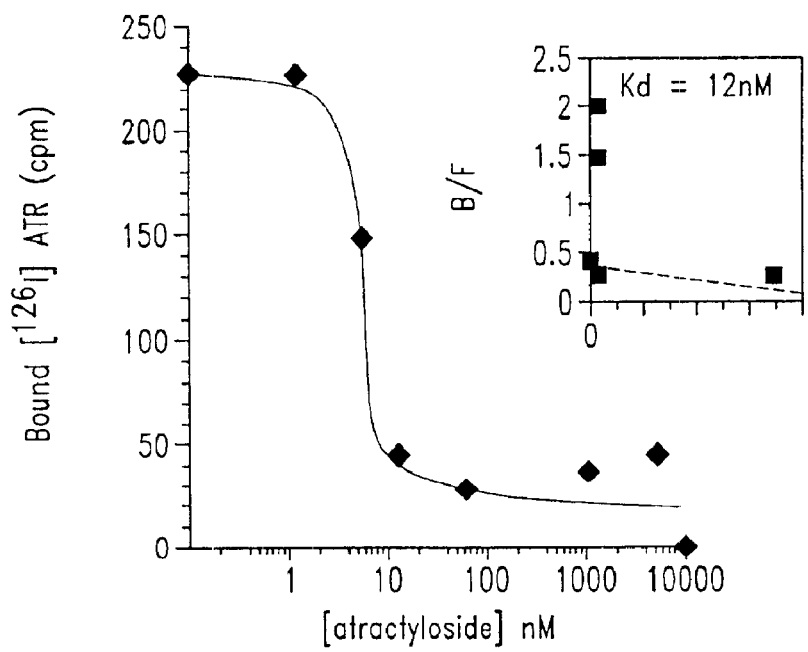
FIG. 9 shows high-affinity binding of atractyloside to Sf9/huANT3 mitochondria.

As illustrated in FIG. 7, ATP bound to the mitochondria with Kd=13 µM, a value consistent with ATP binding to ANT. Furthermore, the ATP binding was displaced by low concentrations of atractyloside (FIG. 8). Homologous competition binding assays using [$^{125}$I]atractyloside revealed specific binding with Kd=12 nM (FIG. 9). These findings are consistent with the presence of functional huANT3 in the mitochondrial preparations.

His-tagged huANT3 protein was purified from baculovirus-infected Sf9 solubilized cell lysates using Ni-agarose magnetic beads; Sf9 cells that had not been infected were used as negative controls. The beads were incubated with [$^{32}$P]ATP (1 or 100 µM) for 2 hr. The beads were washed and then counted to determine the amount of bound ATP. As shown in Table 3, the [$^{32}$P]ATP binding was significantly higher in material recovered from the infected cells than in the controls. Binding saturation had essentially been achieved with 1 µM ATP.

TABLE 3

Binding of [$^{32}$P]ATP to Purified His-Tagged huANT3

| | cpm bound by: | |
|---|---|---|
| [ATP], uM | Control (Uninfected) Cells | huANT3-Producing Cells |
| 1.0 | 43 | 149 |
| 100 | 30 | 160 |

Example 13

Competitive Binding Assays

Atractyloside analogs (Example 6; Table 1; see also Examples 7–9) were used in pseudo-homologous competition binding assays using Sf9/huANT3 mitochondria. Mitochondria (see Example 12, 25 µg/tube) were incubated with 0.5 nM [$^{125}$I]atractyloside and varying concentrations of non-radiolabeled atractyloside or fluorescent atractyloside derivatives as described above (FIGS. 7–9).

The results (Table 4) show that three of the atractyloside derivatives (MANT-, Pyrene- and Coumarin-atractyloside) had relative binding affinities similar to that of authentic atractyloside (IC$_{50}$<500 mM relative to atractyloside). Each of these derivatives is fluorescent, and may therefore be useful as detectable ligands for binding assays.

TABLE 4

Competitive Binding Assays Using [125I]Atractyloside

| [ATR Derivative], nM | cpm [125I]Atractyloside bound in the presence of: | | | |
|---|---|---|---|---|
| | ATR | COU-ATR | PYR-ATR | MANT-ATR |
| 0.0 | 227 | 437 | 437 | 437 |
| 1.0 | 224 | 391 | 350 | — |
| 5.0 | 146 | — | — | — |
| 10 | 42 | 371 | 349 | 229 |
| 50 | 26 | — | — | — |
| 100 | — | 277 | 362 | 195 |
| 1,000 | 36 | 174 | 238 | — |
| 5,000 | 45 | — | — | — |
| 10,000 | 0 | 100 | 0 | — |

Abbreviations and symbols:

ATR, atractlyoside.

COU-ATR, Coumarin-atractyloside, (Table 1, compound 3).

PYR-ATR, Pyrene-atractyloside, (Table 1, compound 4).

MANT-ATR, MANT-atractyloside, (Table 1, Roux et al. 1996 *Anal. Bioch.* 234:31)

---, not determined.

Atractyloside analogs (Example 6; Table 1; see also Examples 7–9) were also used in pseudo-homologous competition binding assays using *T. ni*/huANT3 mitochondria or bovine mitochondria. Mitochondria from noninfected *T. ni* cells, or *T. ni* cells infected with a baculovirus expressing huANT3 (see Example 3) were prepared as follows: *T. ni* cells were prepared by a subcontractor (PharMingen, San Diego, Calif.) as portions of about 250 mg of cells per tube. Each portion was suspended in 1 ml of MSB with protease inhibitors (leupeptin, final concentration 10 ug/ml; pepstatin, final concentration 10 ug/ml; aprotinin, final concentration, 2 ug/ml; phenylmethylsulfonyl fluoride, [PMSF], final concentration, 100 $\mu$M; all from Sigma Chemical Co., St. Louis, Mo.). The resuspended cell suspensions were frozen and thawed twice, then homogenized using a rotating teflon-coated probe and a close-fitting glass container (10 passes). The cellular homogenate was centrifuged (3,700 rpm, approximately 1,500×g) at 4° C. for 5 minutes; this supernatant from the first spin was saved. The pellet was washed with about 500 $\mu$l of MSB with protease inhibitors, centrifuged (3,800 rpm, approximately 1,600×g) at 4° C. for 5 minutes, and supernatant from this spin was combined with the supernatant from the first spin. The combined supernatant was centrifuged (14,000 rpm, approximately 20,800×g) at 4° C. for 15 minutes, and the pellet was resuspended in 300 $\mu$l of a 1:1 solution of (a) 20 mM MOPS and (b) MSB, wherein both (a) and (b) contain the previously described protease inhibitors. The resultant suspension was frozen and thawed three times.

Bovine mitochondria were prepared as follows: Essentially all of the fat and cholesterol in clogged arteries was removed from two bovine hearts which were then cut into 1-inch cubes. The cubes were ground in a meat grinder using the fine setting. Three hundred (300) gm portions of the ground heart were weighed out and, to each was added 400 ml of Isolation Buffer (IB; 250 mM sucrose, 1 mM sodium succinate, 0.2 mM K+ EDTA, 10 mM Tris-base, pH 7.8). (All buffers were filter sterilized, and column buffers were degassed, and, unless otherwise noted, all steps were carried out at 0 to 4° C. on ice or in pre-cooled rotors and centrifuges.) The preparations were mixed in a blender two times for 15 seconds on high setting and, in between and after blends, the pH was adjusted to 7.8 with 2M Tris-base. The homogenate was centrifuged for 20 minutes at 1,200×g, and the supernatant was poured through two layers of cheese cloth and adjusted to pH 7.8 with 2M Tris-base. The supernatant was then centrifuged for 30 minutes at 11,000× g. The supernatant was decanted, and the buff-colored outer pellet was dislodged with about 10 ml of IB and discarded. The brown inner pellet (heavy mitochondria) was resuspended in IB (about 10 ml per pellet). The pellets were homogenized in a glass-teflon homogenizer (2 passes at high drill speed). Samples were combined and centrifuged for 30 minutes at 1,000×g. The supernatant was decanted, and the pellets were resuspended in 60 ml of IB per 900 gm of ground heart. This centrifugation step was repeated and the pellets were finally resuspended in IB (60 ml per 900 gm of ground heart). One kilogram of beef heart typically yields about one (1) gram of mitochondria.

The mitochondrial preparations were divided into aliquots (typically, 50 $\mu$l for *T. ni* mitochondria or 20 $\mu$l for bovine mitochondria) and then either used directly in assays or flash frozen and stored at −80° C. The total protein content in the mitochondrial preparations was determined using the enhanced protocol (30 minutes at 60° C.; see http://www.ruf.rice.edu/~bioslabs/methods/protein/BCA.html) of the bicinchoninic acid (BCA) assay (available in kit form from Pierce, Rockford, Ill.).

In the "Tube Assay," mitochondria (from about 1 to 10 $\mu$g of total protein) were resuspended in 100 $\mu$l of Tris-KCl buffer with 0.1% BSA, pH 7.4. $^{125}$I-labeled compound 24 (Example 11) was added to a final concentration of 0.5 nM. When used, competitors were added at these concentration ranges: unlabeled atractyloside or compound 24, final concentration from 5 nM to 10 $\mu$M; unlabeled ADP (a lower affinity competitor) was added at a final concentration of 500 nM to 1 mM.

The reaction mixes were incubated on ice for 60 minutes and then pelleted by centrifugation (approximately 16,000× g) for 11 minutes at 4° C. Unbound $^{125}$I-compound 24 was removed by aspiration. The pellets were contact-washed with Tris-KCl buffer, pH 7.4, and recentrifuged. The resultant pellets were aspirated and the radioactivity (dpm) in each was determined by gamma counting.

Figure 11:
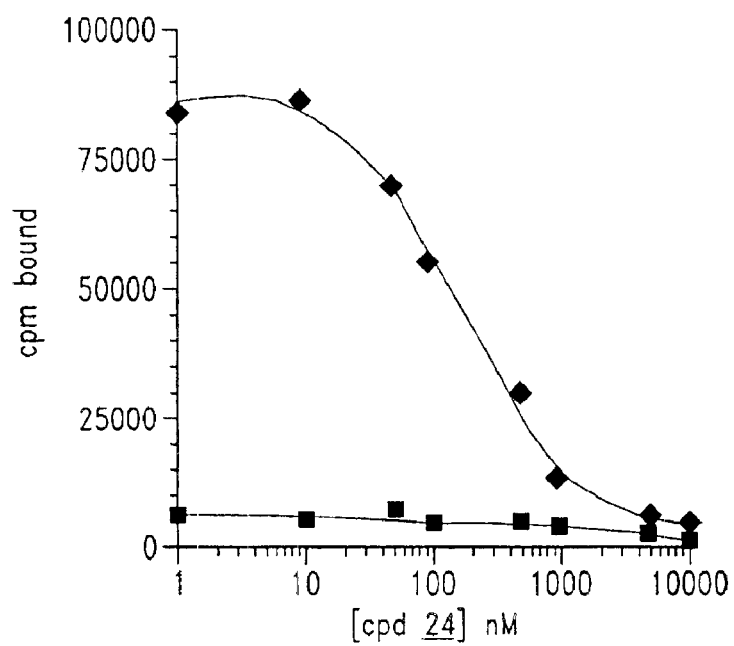
FIG. 11 shows binding of $^{125}$I-compound 24 to bovine mitochondria. Symbols: (▽), bovine mitochondria, (□), control (no mitochondria).
Figure 12:
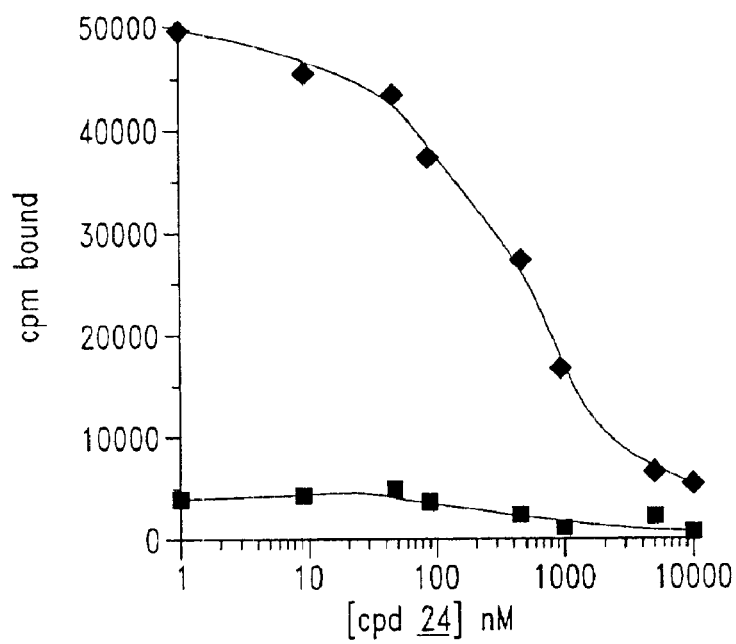
FIG. 12 shows binding of $^{125}$I-compound 24 to mitochondria comprising recombinant huANT3. Symbols: (▽), mitochondria from *T. ni* cells expressing huANT3; (□), control (no mitochondria).

Representative results are shown in FIGS. 11–18. The data presented in FIGS. 11 and 12 show that mitochondria (5 $\mu$g of protein/tube) from both beef heart (FIG. 11) and *T. ni* cells expressing huANT3 (FIG. 12) specifically bind $^{125}$I-compound 24 in a manner that is inhibited by increasing concentrations of unlabeled compound 24, but, as expected, little or no binding is seen when mitochondria are excluded from the reaction mixes.

Figure 13:
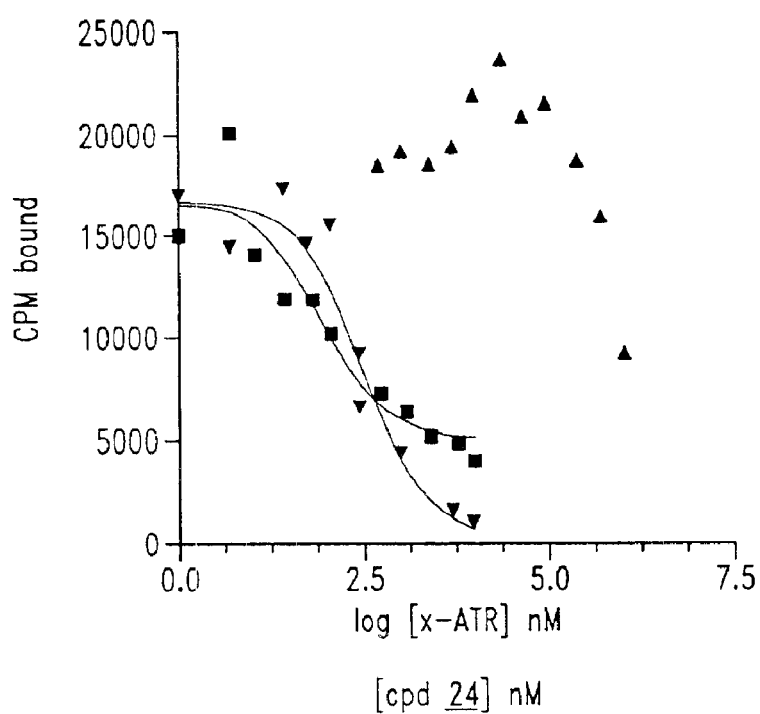
FIG. 13 shows competition of $^{125}$I-compound 24 binding to bovine mitochondria by unlabeled compound 24 (▽), ATR (□) and ADP (Δ).
Figure 14:
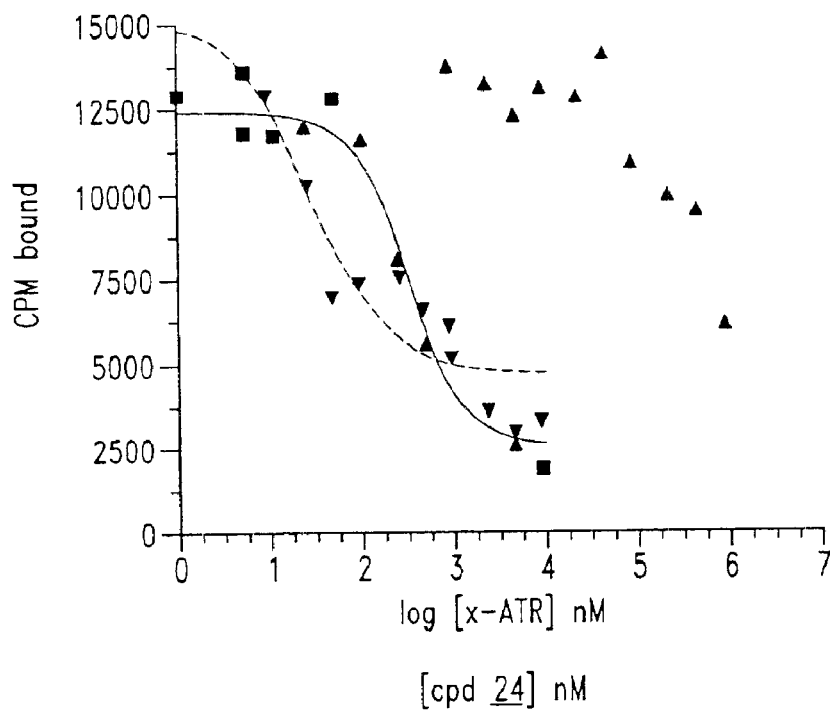
FIG. 14 shows competition of $^{125}$I-compound 24 binding to mitochondria from *T. ni* cells expressing huANT3 by unlabeled compound 24 (▽, dashed line), ATR (□, solid line) and ADP (Δ).

FIGS. 13 and 14 show competitive inhibition of $^{125}$I-compound 24 binding to mitochondria (1 $\mu$g of protein/tube) from beef heart (FIG. 13) and *T. ni* cells expressing huANT3 (FIG. 14) by compound 24 that is not detectably labeled, unlabeled atractyloside (ATR), and unlabeled adenosine diphosphate (ADP). In both instances, ATR and compound 24 yield comparable competition curves, although ATR appears to have a slightly higher affinity than compound 24. However, both ATR and compound 24 bind with much higher (about 1,000 fold) affinity than the low affinity ANT ligand ADP.

Figure 15:
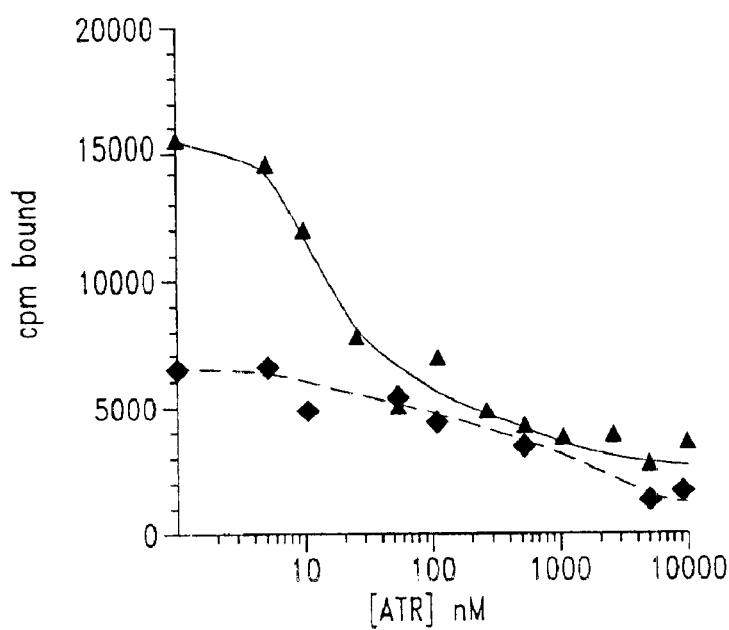
FIG. 15 shows competition of $^{125}$I-compound 24 binding by unlabeled ATR to mitochondria from *T. ni* cells expressing huANT3 (Δ) and control (nontransformed) *T. ni* cells (◇).

FIG. 15 shows the competitive inhibition, by unlabeled ATR, of binding of $^{125}$I-compound 24 to mitochondria (1 $\mu$g of protein/tube) from *T. ni* cells expressing huANT3 and control *T. ni* cells (i.e., non-infected 7: ni cells). As shown in FIG. 15, there was only slight inhibition of $^{125}$I-compound 24 binding to control (nontransformed) mitochondria by higher concentrations of ATR. In contrast, binding of $^{125}$I-compound 24 to mitochondria from *T. ni* cells expressing huANT3 was increasingly inhibited by higher concentrations of ATR.

Figure 16:
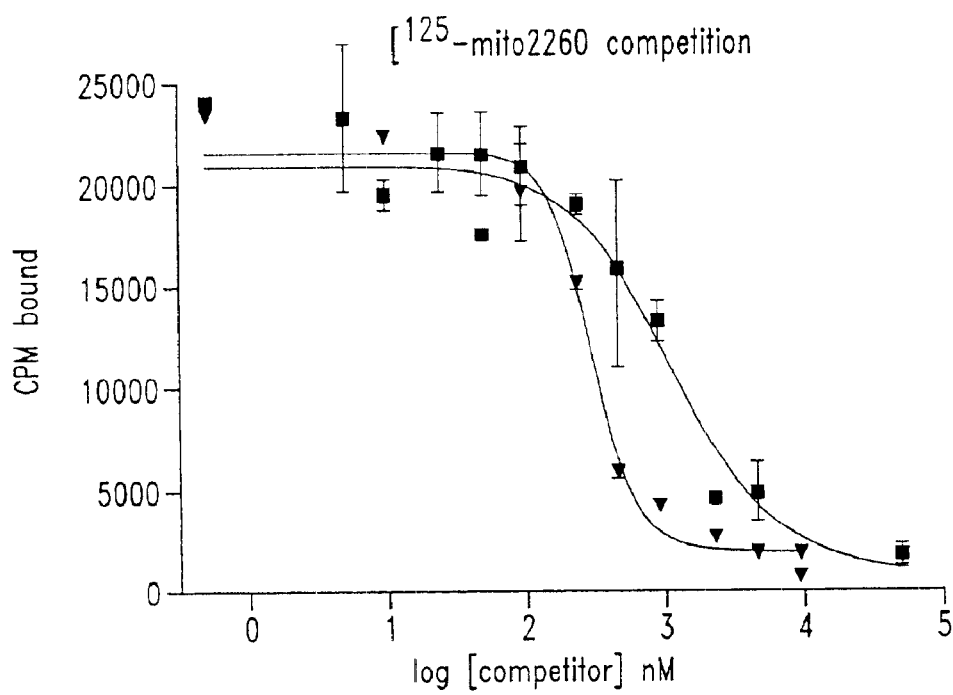
FIG. 16 shows competition of $^{125}$I-compound 24 binding to beef heart mitochondria by (□) BKA and (▽) unlabeled compound 24.
Figure 17:
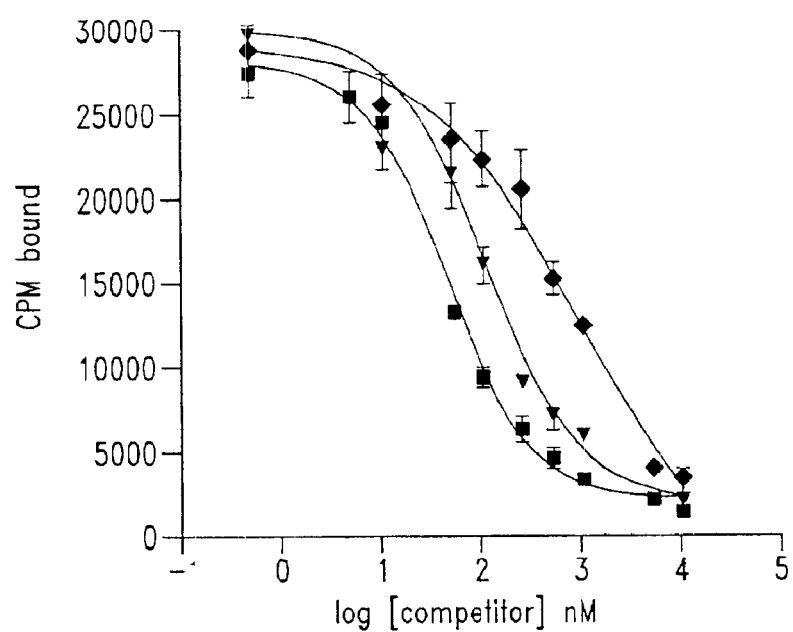
FIG. 17 shows competition of $^{125}$I-compound 24 binding to beef heart mitochondria by compound 23 (▽), compound 28 (◇) and ATR (□).

FIG. 16 shows competitive inhibition, by unlabeled compound 24 and by bongkrekic acid (BKA), of $^{125}$I-compound 24 binding to mitochondria (1 μg of protein/tube) from beef heart. BKA effectively displaced labeled compound 24, albeit with a slightly lower affinity than unlabeled compound 24. FIG. 17 shows competitive inhibition of $^{125}$I-compound 24 binding to beef heart mitochondria by either of the ATR derivatives, compound 23 (see Example 11) and compound 28 (see Example 11). As shown in FIG. 17, ATR exhibited an IC$_{50}$ of approximately 44 nM, compound 23 an IC$_{50}$ of approximately 105 nM, and compound 28 an IC$_{50}$ of approximately 695 nM.

Figure 18:
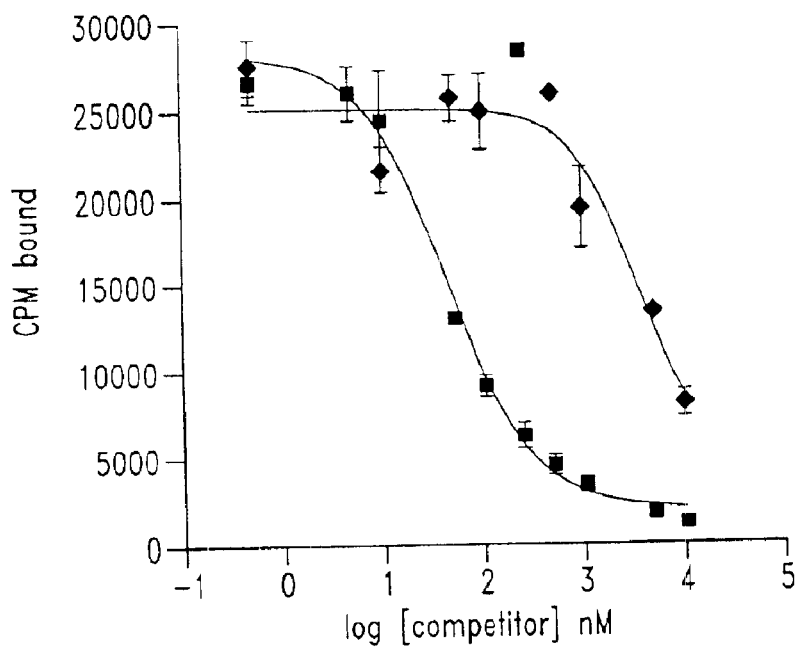
FIG. 18 shows competition of $^{125}$I-compound 24 binding to beef heart mitochondria by compound 5 (◇) and ATR (□).

In FIG. 1, data are presented depicting competitive inhibition of $^{125}$I-compound 24 binding to beef heart mitochondria by the ATR derivative compound 5 (see Example 7). As shown in FIG. 18, the IC$_{50}$ for compound 5 was approximately 3.3 μM.

Figure 19:
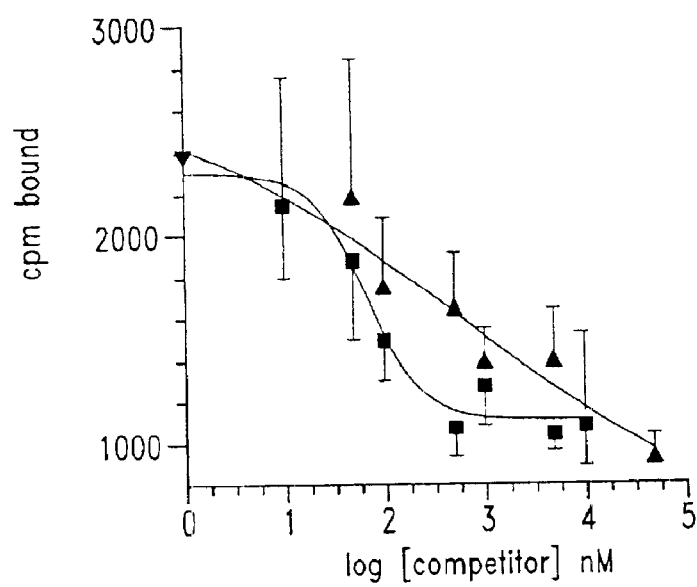
FIG. 19 shows competition of $^{125}$I-compound 24 binding to recombinant His-tagged huANT3 immobilized on Ni beads by BKA (△) and ATR (□).

Competitive binding assays were also performed using recombinant His-tagged huANT3 (see Example 3) immobilized on Ni beads (FIG. 19) instead of mitochondria. To prepare the bead-immobilized huANT3, mitochondria from *T. ni* cells infected with a baculovirus expressing huANT3 (see Example 3) were solubilized with 0.5% O-glucopyranoside in the presence of 0.5 nM $^{125}$I-compound 24, Ni-agarose beads (Qiagen, Hilden, Germany), and various concentrations of ATR or BKA as unlabeled competitors. After 1 hour at 4° C., the beads were washed and radioactivity that remained associated with the beads was counted. (Background binding of [$^{125}$I] compound 24 to Ni-agarose beads (Qiagen) in the absence of His-tagged huANT3 was approximately 700–800 cpm and was not subtracted from the radioactivity shown in FIG. 19.) The results (FIG. 19) show that both ATR and BKA effectively compete with compound 24 in a manner similar to that observed in assays using intact mitochondria (cf. FIGS. 14 and 15).

Example 14

High Throughput Screening Assay for Compounds Targeted to ANT Proteins and Polypeptides The recombinantly produced ANT proteins, ANT fusion proteins and detectably labeled ANT ligands described herein are incorporated into automated assay systems. Such automated systems are useful for high throughput screening (HTS) of candidate ANT-binding compounds or chemical libraries comprising such compounds. Such compounds may be further characterized and developed as drug candidates and drugs useful for preventing, treating or curing diseases or disorders resulting from the overexpression or dysfunction of one or more ANT proteins or from the overexpression or dysfunction of a factor that positively regulates or stimulates ANT proteins.

A preferred element of many automated assay systems is the incorporation of a target molecule (in the present instance, an ANT protein) into a 96-well plate. This format is readily adaptable for use in a variety of automated label detection systems. For HTS assays, robotic label detection systems are preferred.

As one example of an HTS comprising the elements describes herein, the GST-huANT3 fusion protein of Example 2 is contacted with REACTI-BIND™ glutathione-coated 96-well plates (Pierce). Glutathione coated strip-well plates are preferably used for assays comprising radiolabeled ANT ligands (e.g., iodinated atractyloside derivates; see Example 7), whereas black opaque glutathione coated 96-well plates are preferred for assays comprising fluorescent ANT ligands (such as are described in, e.g., Examples 6–9); both types of glutathione coated plates are commercially available (Pierce).

In a typical assay, 1 to 50 ug of GST-huANT3 protein (i.e., total solubilized protein prepared as in Example 2) is added per gluthathione-coated well to each well of a 96-well plate. Iodinated atractyloside derivate ($^{125}$I-ATR) is added to the wells (0.5 nmol/well). In a control experiment, unlabeled atractyloside (ATR; Sigma) is used as a 'mock' drug at a concentration of from about 1 to about 10,000 nM. That is, unlabeled ATR is used to displace a labeled atractyloside derivative (e.g., $^{125}$I-ATR). Unlabeled ATR thus acts as a positive control for an HTS in which various compounds are screened for their ability to displace a labeled ANT ligand.

As an example of the automated label detection systems used in the HTS assays of the Example, when the detectably labeled ANT ligand of the assay is $^{125}$I-ATR, an automatic gamma counter is used. Alternatively, $^{125}$I-ATR can be used in scintillation proximity assays (SPA). For example, a GST-huANT fusion protein is contacted with ScintiStrip 96-well plates coated with glutathione (EG&G Wallac). The polystyrene of these plates contains a scintillating agent that emits beta radiation when excited by a gamma emitter in close proximity thereto. The beta radiation is then detected by any appropriate automatic beta counter. When fluorescent ANT ligands are used in the HTS assay, an automatic fluorescence counter is used and may be, for example, a FLUOROCOUNT™ Counter (Packard Instrument Company, Meriden, Conn.).

We claim:

1. A method for identifying an agent that binds to an adenine nucleotide translocator (ANT) polypeptide, comprising:
   contacting a candidate agent with a host cell expressing a recombinant ANT polypeptide having at least 95% identity to an ANT polypeptide selected from the group consisting of human ANT1; as set forth in SEQ ID NO:31, human ANT2, as set forth in SEQ ID NO:32, and human ANT3; as set forth in SEQ ID NO:33, under conditions and for a time sufficient to permit binding of the agent to said recombinant polypeptide, wherein the host cell comprises a recombinant expression construct comprising at least one regulated promoter operably linked to a nucleic acid encoding the recombinant ANT polypeptide; and
   detecting binding of said agent to the recombinant ANT polypeptide.

2. The method of claim 1 wherein the host cell is a prokaryotic cell.

3. The method of claim 2 wherein the prokaryotic cell is an *E. coli* cell.

4. The method of claim 1 wherein the host cell is a eukaryotic cell.

5. The method of claim 4 wherein the eukaryotic cell is selected from the group consisting of a yeast cell, an insect cell and a mammalian cell.

6. The method of claim 5 wherein the insect cell is selected from the group consisting of an Sf9 cell and a *Trichoplusia ni* cell.

7. The method of any one of claims 1–6 wherein the host cell lacks at least one isoform of an endogenous adenine nucleotide translocator.

8. The method of any one of claims 1–6 wherein host cell expression of at least one gene encoding an endogenous adenine nucleotide translocator isoform is substantially impaired.

9. A method for identifying an agent that binds to an adenine nucleotide translocator (ANT) polypeptide, comprising:
   (a) culturing a host cell comprising a recombinant expression construct that comprises at least one regulated promoter operably linked to a nucleic acid encoding a recombinant ANT polypeptide selected from the group consisting of (i) a recombinant polypeptide comprising an amino acid sequence at least 95% identical to human ANT1 as set forth in SEQ ID NO:31, (ii) a recombinant polypeptide comprising the amino acid sequence of human ANT2 as set forth in SEQ ID NO:32, and (iii) a recombinant polypeptide comprising the amino acid sequence of human ANT3 as set forth in SEQ ID NO:33, to produce a biological sample that comprises said recombinant ANT polypeptide;
   (b) contacting a candidate agent with the biological sample of (a) under conditions and for a time sufficient to permit binding of the agent to said recombinant ANT polypeptide; and
   (c) detecting binding of said agent to the recombinant ANT polypeptide.

10. A method for identifying an agent that interacts with an adenine nucleotide translocator (ANT) polypeptide comprising:
  (a) culturing a host cell comprising a recombinant expression construct that comprises at least one regulated promoter operably linked to a nucleic acid encoding a recombinant ANT polypeptide having at least 95% identity to an ANT polypeptide selected from the group consisting of human ANT1 as set forth in SEQ ID NO:31, human ANT2 as set forth in SEQ ID NO:32, and human ANT3 as set forth in SEQ ID NO:33, to produce a biological sample that comprises said recombinant ANT polypeptide;
  (b) contacting the biological sample with a detectable ANT ligand in the absence and in the presence of a candidate agent; and
  (c) comparing binding of the detectable ANT ligand to the recombinant ANT polypeptide in the absence of said agent to binding of the detectable ANT ligand to the recombinant ANT polypeptide in the presence of said agent, and therefrom identifying an agent that interacts with an ANT polypeptide.

11. A method for identifying an agent that binds to an adenine nucleotide translocator (ANT) polypeptide, comprising:
  (a) contacting a candidate agent with a host cell expressing a recombinant ANT fusion protein that comprises an ANT polypeptide fused to at least one additional polypeptide sequence, wherein the fused ANT polypeptide has a sequence at least 95% identical to an ANT polypeptide selected from the group consisting of human ANT1 as set forth in SEQ ID NO:31, human ANT2 as set forth in SEQ ID NO:32, and human ANT3 as set forth in SEQ ID NO:33, under conditions and for a time sufficient to permit binding of the agent to said fused ANT polypeptide, wherein the host cell comprises a recombinant expression construct comprising at least one regulated promoter operably linked to a nucleic acid encoding the recombinant ANT fusion protein; and
  (b) detecting binding of said agent to the recombinant ANT fusion protein.

12. The method of claim 11 wherein the host cell is a prokaryotic cell.

13. The method of claim 12 wherein the prokaryotic cell is an *E. coli* cell.

14. The method of claim 11 wherein the host cell is a eukaryotic cell.

15. The method of claim 14 wherein the eukaryotic cell is selected from the group consisting of a yeast cell, an insect cell, and a mammalian cell.

16. The method of claim 15 wherein the insect cell is selected from the group consisting of an Sf9 cell and a *Trichoplusia ni* cell.

17. The method of any one of claims 12–16 wherein the host cell lacks at least one isoform of an endogenous adenine nucleotide translocator.

18. The method of any one of claims 12–16 wherein host cell expression of at least one gene encoding an endogenous adenine nucleotide translocator isoform is substantially impaired.

19. A method for identifying an agent that binds to an adenine nucleotide translocator (ANT) polypeptide, comprising:
  (a) culturing a host cell comprising at least one recombinant expression construct that comprises at least one regulated promoter operably linked to a nucleic acid encoding a recombinant ANT fusion protein to produce a biological sample that comprises said ANT fusion protein, wherein the ANT fusion protein comprises an ANT polypeptide fused to at least one additional polypeptide sequence, wherein the fused ANT polypeptide has a sequence at least 95% identical to an ANT polypeptide selected from the group consisting of human ANT1 as set forth in SEQ ID NO:31, human ANT2 as set forth in SEQ ID NO:32, and human ANT3 as set forth in SEQ ID NO:33;
  (b) contacting a candidate agent with the biological sample of (a) under conditions and for a time sufficient to permit binding of the agent to said ANT fusion protein; and
  (c) detecting binding of said agent to the ANT fusion protein.

20. A method for identifying an agent that interacts with an adenine nucleotide translocator (ANT) polypeptide comprising:
  (a) contacting, in the absence and in the presence of a candidate agent, a biological sample comprising a recombinant ANT fusion protein with a detectable ANT ligand under conditions and for a time sufficient to permit binding of the ANT ligand to the fusion protein, wherein the fusion protein comprises an ANT polypeptide fused to at least one additional polypeptide sequence, wherein said fused ANT polypeptide has a sequence at least 95% identical to an ANT polypeptide selected from the group consisting of (i) human ANT1 as set forth in SEQ ID NO:31; (ii) human ANT2 as set forth in SEQ ID NO:32; and (iii) human ANT3 as set forth in SEQ ID NO:33; and
  (b) comparing binding of the detectable ANT ligand to the ANT fusion protein in the absence of said agent to binding of the detectable ANT ligand to the ANT fusion protein in the presence of said agent, and therefrom identifying an agent that interacts with an ANT polypeptide.

21. An assay plate for high throughput screening of candidate agents that bind to at least one adenine nucleotide translocator (ANT) polypeptide, comprising:
  an assay plate having a plurality of wells, each of said wells comprising at least one immobilized recombinant ANT polypeptide selected from the group consisting of human ANT1, comprising an amino acid sequence as set forth in SEQ ID NO:31, a human ANT1 variant comprising an amino acid sequence having at least 95% identity to the amino acid sequence set forth in SEQ ID NO:31, human ANT2, comprising an amino acid sequence as set forth in SEQ ID NO:32, and human ANT3; comprising an amino acid sequence as set forth in SEQ ID NO:33.

22. An assay plate for high throughput screening of candidate agents that bind to at least one adenine nucleotide translocator (ANT) polypeptide, comprising:
  an assay plate having a plurality of wells, each of said wells comprising at least one immobilized recombinant ANT fusion protein that comprises an ANT polypeptide fused to at least one additional polypeptide sequence, wherein said ANT polypeptide comprises an amino acid sequence that is at least 95% identical to that of an ANT polypeptide selected from the group consisting of (i) human ANT1 as set forth in SEQ ID NO:31; (ii) human ANT2 as set forth in SEQ ID NO:32; and (ii) human ANT3 as set forth in SEQ ID NO:33.

* * * * *

UNITED STATES PATENT AND TRADEMARK OFFICE
CERTIFICATE OF CORRECTION

PATENT NO.         : 7,001,729 B2  
APPLICATION NO. : 09/811113  
DATED                 : February 21, 2006  
INVENTOR(S)        : Christen M. Anderson et al.

Page 1 of 1

It is certified that error appears in the above-identified patent and that said Letters Patent is hereby corrected as shown below:

Title Page, Item (75) Col. 1  
Inventors (75), "Christen M. Anderson, Encinitas, CA (US); Robert E. Davis, San Diego, CA (US); William Clevenger, Oceanside, CA (US); Sandra Eileen Wiley, San Diego, CA (US); Scott W. Miller, San Marcos, CA (US); Thomas R. Szabo, San Diego, CA (US); Soumitra S. Ghosh, San Diego, CA (US); Walter H. Moos, Oakland, CA (US); Yazhong Pei, San Diego, CA (US)" should read as -- Christen M. Anderson, Encinitas, CA (US); Robert E. Davis, San Diego, CA (US); William Clevenger, Oceanside, CA (US); Scott W. Miller, San Marcos, CA (US)--.

Signed and Sealed this

Eighth Day of August, 2006

JON W. DUDAS  
*Director of the United States Patent and Trademark Office*

UNITED STATES PATENT AND TRADEMARK OFFICE
CERTIFICATE OF CORRECTION

PATENT NO. : 7,001,729 B2  Page 1 of 1
APPLICATION NO. : 09/811131
DATED : February 21, 2006
INVENTOR(S) : Christen M. Anderson et al.

It is certified that error appears in the above-identified patent and that said Letters Patent is hereby corrected as shown below:

Title Page, Item (75) Col. 1
Inventors (75), "Christen M. Anderson, Encinitas, CA (US); Robert E. Davis, San Diego, CA (US); William Clevenger, Oceanside, CA (US); Sandra Eileen Wiley, San Diego, CA (US); Scott W. Miller, San Marcos, CA (US); Thomas R. Szabo, San Diego, CA (US); Soumitra S. Ghosh, San Diego, CA (US); Walter H. Moos, Oakland, CA (US); Yazhong Pei, San Diego, CA (US)" should read as -- Christen M. Anderson, Encinitas, CA (US); Robert E. Davis, San Diego, CA (US); William Clevenger, Oceanside, CA (US); Scott W. Miller, San Marcos, CA (US)--.

This certificate supersedes Certificate of Correction issued August 8, 2006.

Signed and Sealed this

Tenth Day of October, 2006

JON W. DUDAS
*Director of the United States Patent and Trademark Office*